(12) United States Patent
Zou et al.

(10) Patent No.: US 12,357,682 B2
(45) Date of Patent: Jul. 15, 2025

(54) DNA PLASMID-LAUNCHED LIVE-ATTANUATED VACCINES FOR PLUS-SENSE SINGEL STRANDED RNA

(71) Applicant: Board of Regents, the University of Texas System, Austin, TX (US)

(72) Inventors: Jing Zou, Galveston, TX (US); Xuping Xie, Galveston, TX (US); Pei-Yong Shi, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 472 days.

(21) Appl. No.: 17/273,258

(22) PCT Filed: Aug. 30, 2019

(86) PCT No.: PCT/US2019/049036
§ 371 (c)(1),
(2) Date: Mar. 3, 2021

(87) PCT Pub. No.: WO2020/051080
PCT Pub. Date: Mar. 12, 2020

(65) Prior Publication Data
US 2021/0338794 A1     Nov. 4, 2021

Related U.S. Application Data

(60) Provisional application No. 62/726,813, filed on Sep. 4, 2018.

(51) Int. Cl.
| A61K 39/12 | (2006.01) |
| A61P 31/14 | (2006.01) |
| A61K 39/00 | (2006.01) |

(52) U.S. Cl.
CPC .............. *A61K 39/12* (2013.01); *A61P 31/14* (2018.01); *A61K 2039/5254* (2013.01); *A61K 2039/53* (2013.01); *A61K 2039/545* (2013.01); *A61K 2039/552* (2013.01)

(58) Field of Classification Search
None
See application file for complete search history.

(56) References Cited

U.S. PATENT DOCUMENTS

2007/0036827 A1* 2/2007 Khromykh ............... C12N 7/00
                                                                435/5
2013/0243809 A1   9/2013 Liao et al.

OTHER PUBLICATIONS

Xi et al. (EBio Medicine. 2016; 12: 156-160).*
Tretyakova et al. (Vaccine. 2013; 31: 1019-1025).*
(Continued)

*Primary Examiner* — Shanon A. Foley

(57) ABSTRACT

The invention generally relates to the development of immunogenic compositions comprising a DNA copy of at least one live attenuated plus-sense single-stranded RNA virus genome, such as the genome of a live-attenuated Zika vims (ZIKV), Japanese encephalitis virus (JEV) or yellow fever vims (YFV). The immunogenic compositions can be used for treating or conferring protective immunity against diseases related to plus-sense single-stranded RNA viruses, e.g. for affording prolonged immunoprotection against such viruses and protective immunity is conferred at low diseases, e.g., as low as 300 or 500 ng after administration of a single pLAV dosage.

6 Claims, 25 Drawing Sheets

Specification includes a Sequence Listing.

(56) References Cited

OTHER PUBLICATIONS

Tratyakova et al. (Journal of Infectious Diseases. 2014; 209: 1882-1890).*

Nickols et al. (Virology. 2017; 512: 66-73).*

Nickols, B., et al., Plasmid DNA launches live-attenuated Japanese encephalitis virus and elicits virus-neutralizing antibodies in BALB/c mice. Virology, 2017. 512: p. 66-73.

Weaver, S.C., et al., Zika virus: History, emergence, biology, and prospects for control. Antiviral Res, 2016. 130: p. 69-80.

Shan, C., X. Xie, and P.Y. Shi, Zika Virus Vaccine: Progress and Challenges. Cell Host Microbe, 2018. 24(1): p. 12-17.

Kie, X., et al., Small Molecules and Antibodies for Zika Therapy. J Infect Dis, 2017. 216(suppl_10): p. S945-S950.

Abbink, P., K.E. Stephenson, and D.H. Barouch, Zika virus vaccines. Nat Rev Microbiol, 2018.

Modjarrad, K., et al., Preliminary aggregate safety and immunogenicity results from three trials of a purified inactivated Zika virus vaccine candidate: phase 1, randomised, double-blind, placebo-controlled clinical trials. Lancet, 2017.

Abbink, P., et al., Protective efficacy of multiple vaccine platforms against Zika virus challenge in rhesus monkeys. Science, 2016. 353(6304): p. 1129-32.

Pardi, N., et al., Zika virus protection by a single low-dose nucleoside-modified mRNA vaccination. Nature, 2017.

Richner, J., et al., Vaccine mediated protection against Zika virus induced congenital disease. Cell, 2017. 170: p. 273-283.

Richner, J.M., et al., Modified mRNA Vaccines Protect against Zika Virus Infection. Cell, 2017.

Dowd, K.A., et al., Rapid development of a DNA vaccine for Zika virus. Science, 2016. 354(6309): p. 237-240.

Larocca, R.A., et al., Vaccine protection against Zika virus from Brazil. Nature, 2016. 536(7617): p. 474-8.

Chattopadhyay, A., et al., A recombinant virus vaccine that protects against both Chikungunya and Zika virus infections. Vaccine, 2018. 36(27): p. 3894-3900.

Shan, C., et al., A single-dose live-attenuated vaccine prevents Zika virus pregnancy transmission and testis damage. Nat Commun, 2017. 8(1): p. 676.

Xie, X., et al., Understanding Zika Virus Stability and Developing a Chimeric Vaccine through Functional Analysis. MBio, 2017. 8(1).

Li, X.F., et al., Development of a chimeric Zika vaccine using a licensed live-attenuated flavivirus vaccine as backbone. Nat Commun, 2018. 9(1): p. 673.

Ghaffarifar, F., Plasmid DNA vaccines: where are we now? Drugs Today (Barc), 2018. 54(5):p. 315-333.

Yang, Y., et al., A cDNA Clone-Launched Platform for High-Yield Production of Inactivated Zika Vaccine. EBioMedicine, 2017. 17: p. 145-156.

Shan, C., et al., An Infectious cDNA Clone of Zika Virus to Study Viral Virulence, Mosquito Transmission, and Antiviral Inhibitors. Cell Host Microbe, 2016. 19(6): p. 891-900.

Xie, X., et al., Zika Virus Replicons for Drug Discovery. EBioMedicine, 2016. 12: p. 156-160.

Dupuy, L.C., et al., A DNA vaccine for venezuelan equine encephalitis virus delivered by intramuscular electroporation elicits high levels of neutralizing antibodies in multiple animal models and provides protective immunity to mice and nonhuman primates. Clin Vaccine Immunol, 2011. 18(5): p. 707-16.

Elong Ngono, A., et al., Mapping and Role of the CD8(+) T Cell Response During Primary Zika Virus Infection in Mice. Cell Host Microbe, 2017. 21(1): p. 35-46.

Shan, C., et al., A live-attenuated Zika virus vaccine candidate induces sterilizing immunity in mouse models. Nat Med, 2017. 23(6): p. 763-767.

Cheeseman, H.M., et al., Combined skin and muscle DNA priming provides enhanced humoral responses to an HIV-1 clade C envelope vaccine. Hum Gene Ther, 2018.

Minor, P.D., Live attenuated vaccines: Historical successes and current challenges. Virology, 2015. 479-480: p. 379-92.

Hall, R.A., et al., DNA vaccine coding for the full-length infectious Kunjin virus RNA protects mice against the New York strain of West Nile virus. Proc. Natl. Acad. Sci. USA, 2003. 100(18): p. 10460-4.

Tretyakova, I., et al., Plasmid DNA initiates replication of yellow fever vaccine in vitro and elicits virus-specific immune response in mice. Virology, 2014. 468-470: p. 28-35.

Tretyakova, I., et al., DNA vaccine initiates replication of live attenuated chikungunya virus in vitro and elicits protective immune response in mice. J Infect Dis,

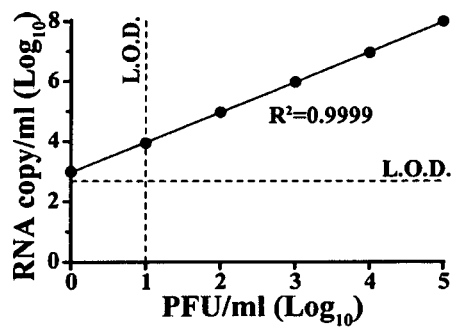
FIG. 12
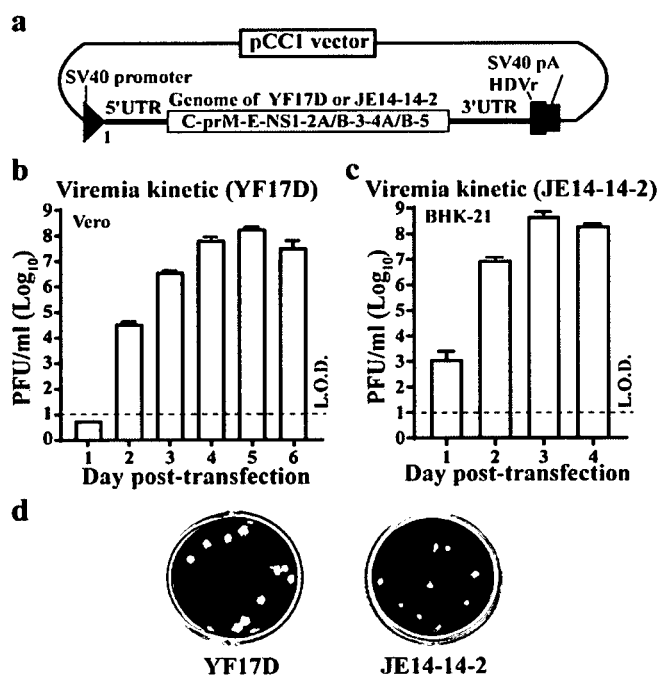
FIG. 13A-D

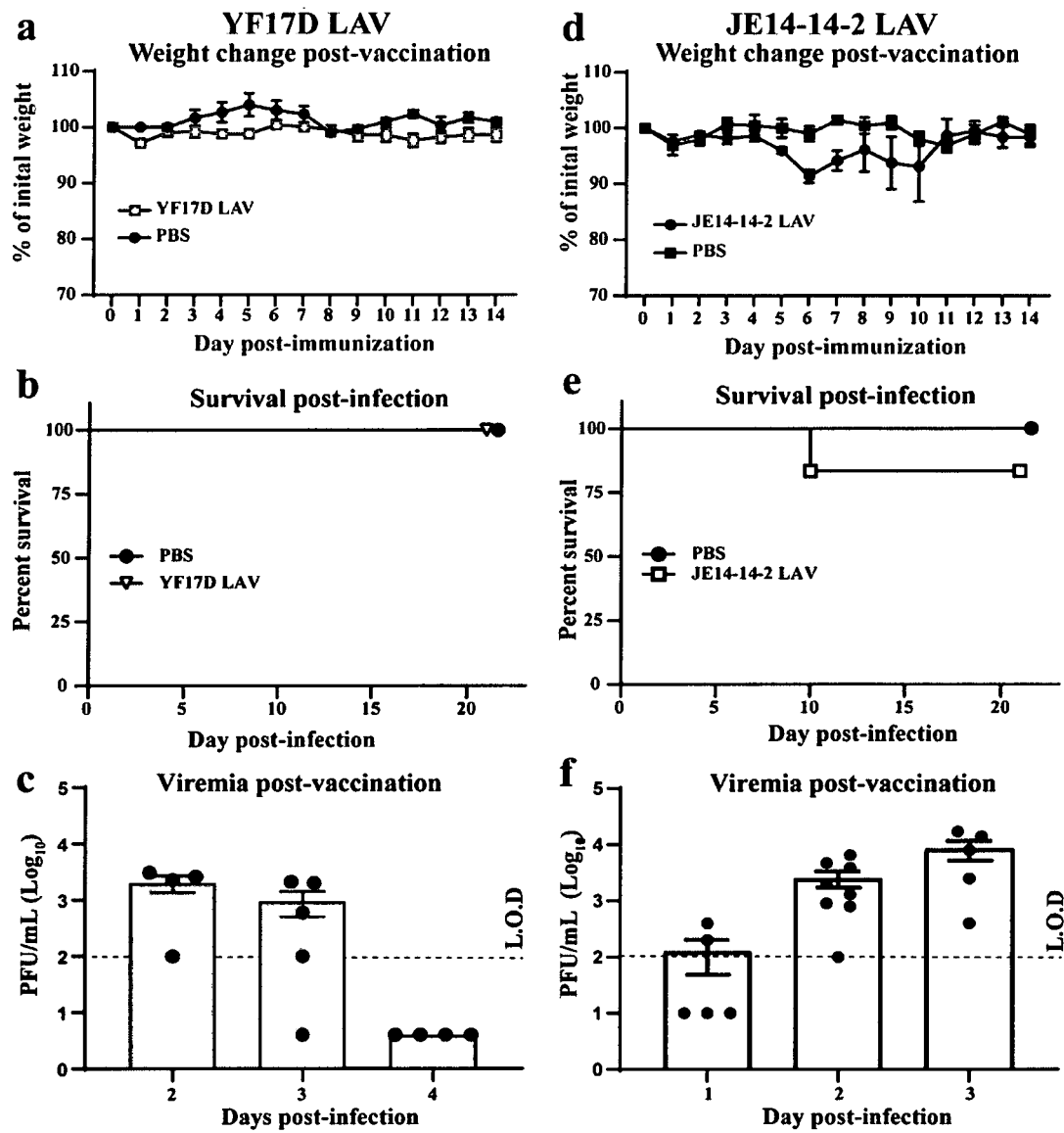
FIG. 14A-F.

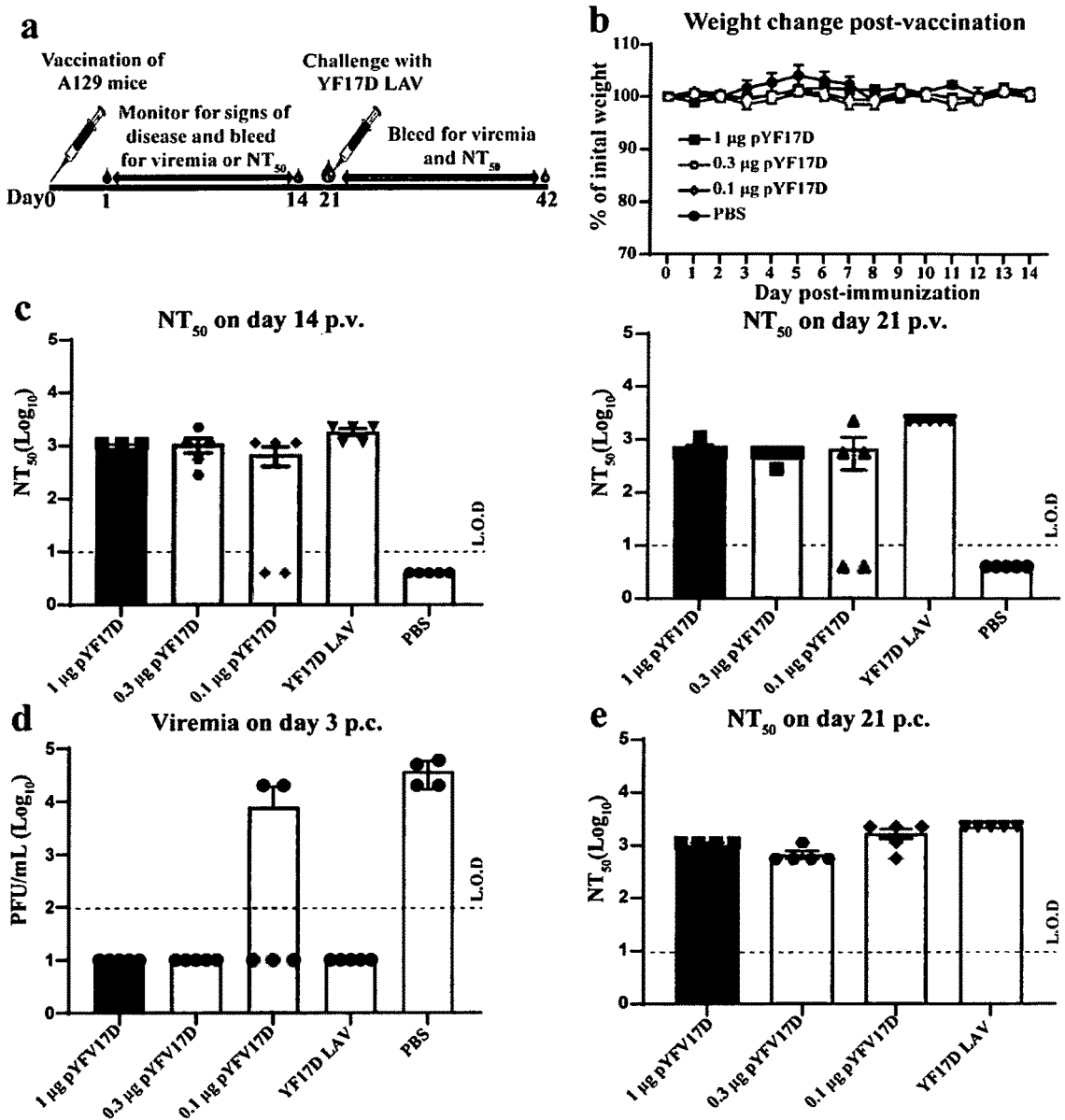
FIG. 15A-E.

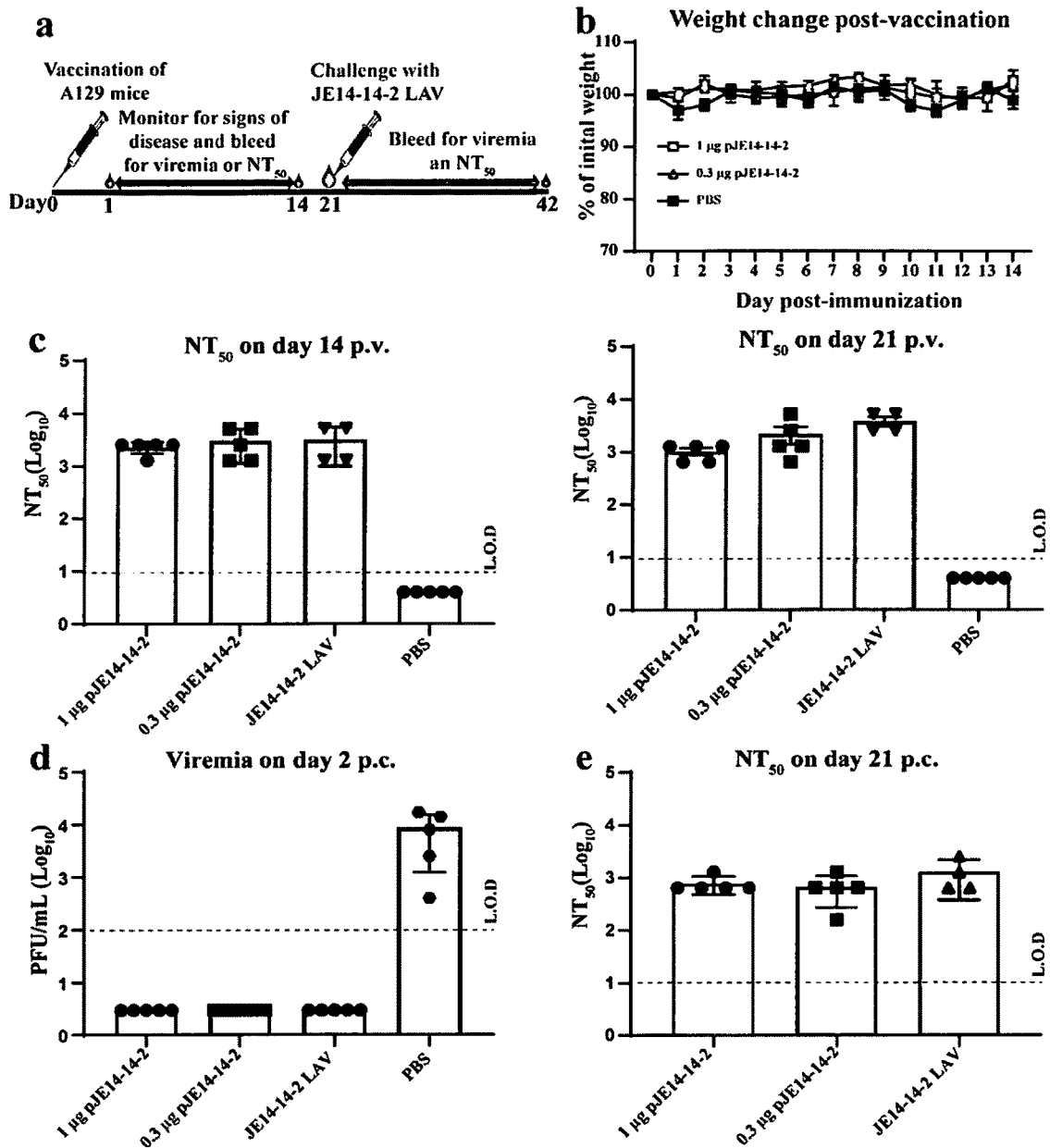
FIG. 16A-E.

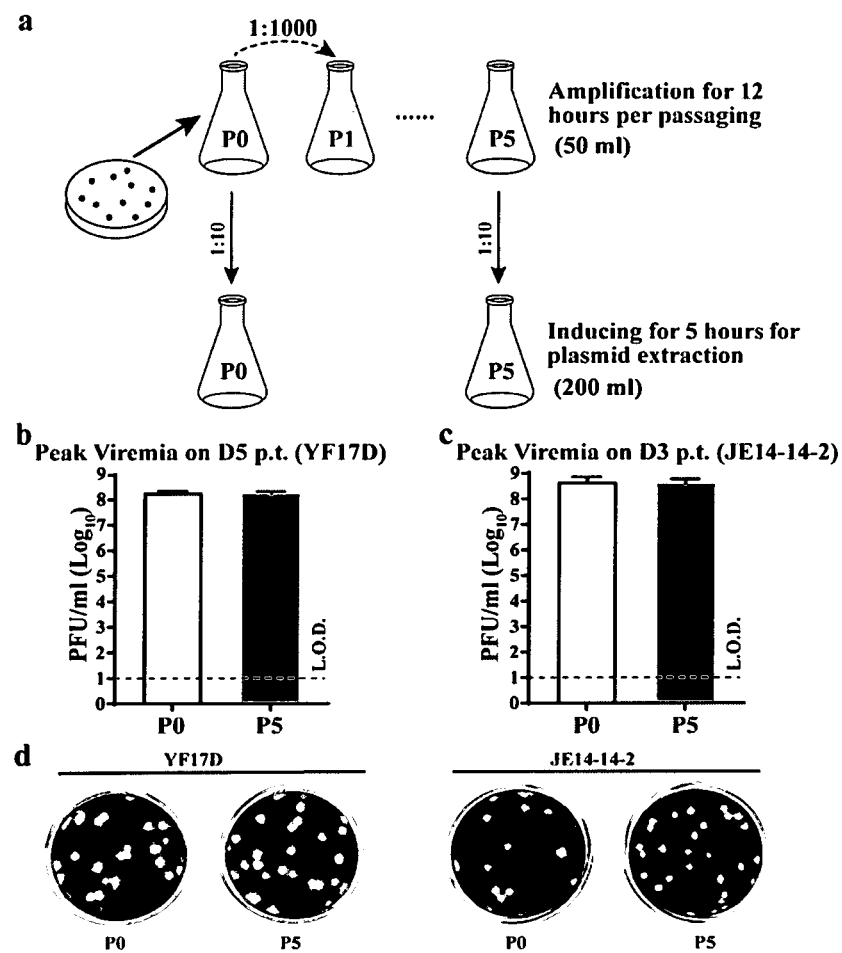
FIG. 17A-D.

FIG. 18. Genome sequence of JE14-14-2 used in Example 2 (SEQ ID NO: 1)

```
AGAAGTTTATCTGTGTGAACTTCTTGGCTTAGTATCGTAGAGAAGAATCGAGAGATTAGTGC
AGTTTAAACAGTTTTTTAGAACGGAAGATAACCATGACTAAAAAACCAGGAGGGCCCGGTA
AAAACCGGGCTATCAATATGCTGAAACGCGGCCTACCCCGCGTATTCCCACTAGTGGGAGTG
AAGAGGGTAGTAATGAGCTTGTTGGACGGCAGAGGGCCAGTACGTTTCGTGCTGGCTCTTAT
CACGTTCTTCAAGTTTACAGCATTAGCCCCGACCAAGGCGCTTTCAGGCCGATGGAAAGCAG
TGGAAAAGAGTGTGGCAATGAAACATCTTACTAGTTTCAAACGAGAACTTGGAACACTCATT
GACGCCGTGAACAAGCGGGGCAGAAAGCAAAACAAAAGAGGAGGAAATGAAGGCTCAATC
ATGTGGCTCGCGAGCTTGGCAGTTGTCATAGCTTGTGCAGGAGCCATGAAGTTGTCGAATTT
CCAGGGGAAGCTTTTGATGACCATCAACAACACGGACATTGCAGACGTTATCGTGATTCCCA
CCTCAAAAGGAGAGAACAGATGCTGGGTCCGGGCAATCGACGTCGGCTACATGTGTGAGGA
CACTATCACGTACGAATGTCCTAAGCTTACCATGGGCAATGATCCAGAGGATGTGGATTGCT
GGTGTGACAACCAAGAAGTCTACGTCCAATATGGACGGTGCACGCGGACCAGGCATTCCAA
GCGAAGCAGGAGATCCGTGTCGGTCCAAACACATGGGGAGAGTTCACTAGTGAATAAAAAA
GAGGCTTGGCTGGATTCAACGAAAGCCACACGATATCTCATGAAAACTGAGAACTGGATCA
TAAGGAATCCTGGCTATGCTTTCCTGGCGGCGGTACTTGGCTGGATGCTTGGCAGTAACAAC
GGTCAACGCGTGGTATTTACCATCCTCCTGCTGTTGGTCGCTCCGGCTTACAGTTTTAATTGT
CTGGGAATGGGCAATCGTGACTTCATAGAAGGAGCCAGTGGAGCCACTTGGGTGGACTTGG
TGCTAGAAGGAGACAGCTGCTTGACAATCATGGCAAACGACAAACCAACATTGGACGTCCG
CATGATTAGCATCGAAGCTAGCCAACTTGCTGAGGTCAGAAGTTACTGCTATCATGCTTCAG
TCACTGACATCTCGACGGTGGCTCGGTGCCCCACGACTGGAGAAGCCCACAACGAGAAGCG
AGCTGATAGTAGCTATGTGTGCAAACAAGGCTTCACTGACCGTGGGTGGGGCAACGGATGT
GGATTTTCGGGAAGGGAAGCATTGACACATGTGCAAAATTCTCCTGCACCAGTAAAGCGAT
TGGGAGAACAATCCAGCCAGAAAACATCAAATACAAAGTTGGCATTTTGTGCATGGAACC
ACCACTTCGGAAAACCATGGGAATTATTCAGCGCAAGTTGGGGCGTCCCAGGCGGCAAAGT
TTACAGTAACACCCAATGCTCCTTCGGTAGCCCTCAAACTTGGTGACTACGGAGAAGTCACA
CTGGACTGTGAGCCAAGGAGTGGACTGAACACTGAAGCGTTTTACGTCATGACCGTGGGGTC
AAAGTCATTTCTGGTCCATAGGGAGTGGTTTCATGACCTCGCTCTCCCCTGGACGTCCCCTTC
GAGCACAGCGTGGAGAAACAGAGAACTCCTCATGGAATTTGAAGGGGCGCACGCCACAAAA
CAGTCCGTTGTTGCTCTTGGGTCACAGGAAGGAGGCCTCCATCATGCGTTGGCAGGAGCCAT
CGTGGTGGAGTACTCAAGCTCAGTGAAGTTAACATCAGGCCACCTGAAATGTAGGCTGAAA
ATGGACAAACTGGCTCTGAAAGGCACAACCTATGGCATGTGTACAGAAAAATTCTCGTTCGC
GAAAAATCCGGTGGACACTGGTCACGGAACAGTTGTCATTGAACTCTCCTACTCTGGGAGTG
ATGGCCCCTGCAAAATTCCGATTGTTTCCGTTGCGAGCCTCAATGACATGACCCCCGTTGGG
CGGCTGGTGACAGTGAACCCCTTCGTCGCGACTTCCAGTGCCAACTCAAAGGTGCTGGTCGA
GATGGAACCCCCTTCGGAGACTCCTACATCGTAGTTGGAAGGGGAGACAAGCAGATCAAC
CACCATTGGCACAAAGCTGGAAGCACGCTGGGCAAGGCCTTTTCAACAACTTTGAAGGGAG
CTCAAAGACTGGCAGCGTTGGGCGACACAGCCTGGGACTTTGGCTCTATTGGAGGGGTCTTC
AACTCCATAGGAAGAGCCGTTCACCAAGTGTTTGGTGGTGCCTTCAGAACACTCTTTGGGGG
AATGTCTTGGATCACACAAGGGCTAATGGGTGCCCTACTGCTCTGGATGGGCGTCAACGCAC
GAGACCGATCAATTGCTTTGGCCTTCTTAGCCACAGGAGGTGTGCTCGTGTTCTTAGCGACC
AATGTGCATGCTGACACTGGATGTGCCATTGACATCACAAGAAAAGAGATGAGATGTGGAA
GTGGCATCTTCGTGCACAACGACGTGGAAGCCTGGGTGGATAGGTATAAATATTTGCCAGAA
ACGCCCAGATCCCTAGCGAAGATCGTCCACAAAGCGCACAAGGAAGGCGTGTGCGGAGTCA
GATCTGTCACTAGACTGGAGCACCAAATGTGGGAAGCCGTAAGGGACGAATTGAACGTCCT
```

FIG. 18. Cont.

```
GCTCAAAGAGAATGCAGTGGACCTCAGTGTGGTTGTGAACAAGCCCGTGGGAAGATATCGC
TCAGCCCCTAAACGCCTATCCATGACGCAAGAGAAGTTTGAAATGGGCTGGAAAGCATGGG
GAAAAAGCATCCTCTTTGCCCCGGAATTGGCTAACTCCACATTTGTCGTAGATGGACCTGAG
ACAAAGGAATGCCCTGATGAGCACAGAGCTTGGAACAGCATGCAAATCGAAGACTTCGGCT
TTGGCATCACATCAACCCGTGTGTGGCTGAAAATTAGAGAGGAGAGCACTGACGAGTGTGA
TGGAGCGATCATAGGCACGGCTGTCAAAGGACATGTGGCAGTCCATAGTGACTTGTCGTACT
GGATTGAGAGTCGCTACAACGACACATGGAAACTTGAGAGGGCAGTCTTTGGAGAGGTCAA
ATCTTGCACTTGGCCAGAGACACACACCCTTTGGGGAGATGATGTTGAGGAAAGTGAACTCA
TCATTCCGCACACCATAGCCGGACCAAAAAGCAAGCACAATCGGAGGGAAGGGTATAAGAC
ACAAAACCAGGGACCTTGGGATGAGAATGGCATAGTCTTGGACTTTGATTATTGCCCAGGGA
CAAAAGTCACCATTACAGAGGATTGTAGCAAGAGAGGCCCTTCGGTCAGAACCACTACTGA
CAGTGGAAAGTTGATCACTGACTGGTGCTGTCGCAGTTGCTCCCTTCCGCCCCTACGATTCCG
GACAGAAAATGGCTGCTGGTACGGAATGGAAATCAGACCTGTTATGCATGATGAAACAACA
CTCGTCAGATCACAGGTTCATGCTTTCAAAGGTGAAATGGTTGACCCTTTTCAGCTGGGCCTT
CTGGTGATGTTTCTGGCCACCCAGGAAGTCCTTCGCAAGAGGTGGACGGCCAGATTGACCAT
TCCTGCGGTTTTGGGGGTCCTACTTGTGCTGATGCTTGGGGGTATCACTTACACTGATTTGGC
GAGGTATGTGGTGCTAGTCGCTGCTGCTTTCGCAGAGGCCAACAGTGGAGGAGACGTCCTGC
ACCTTGCTTTGATTGCTGTTTTAAGATCCAACCAGCATTTTTAGTGATGAACATGCTTAGCA
CGAGATGGACGAACCAAGAAAACGTGGTTCTGGTCCTAGGGGCTGCCTTTTCCAATTGGCC
TCAGTAGATCTGCAAATAGGAGTCCACGGAATCCTGAATGCCGCCGCTATAGCATGGATGAT
TGTCCGAGCGATCACCTTCCCCACAACCTCCTCCGTCACCATGCCAGTCTTAGCGCTTCTAAC
TCCGGGGATGAGGGCTCTATACCTAGACACTTACAGAATCATCCTCCTCGTCATAGGGATTT
GCTCCCTGCTGCACGAGAGGAAAAAGACCATGGCGAAAAGAAAGGAGCTGTACTCTTGGG
CTTAGCGCTCACATCCACTGGATGGTTCTCGCCCACCACTATAGCTGCCGGACTAATGGTCT
GCAACCCAAACAAGAAGAGAGGGTGGCCAGCTACTGAGTTTTTGTCGGCAGTTGGATTGAT
GTTTGCCATCGTAGGTGGTTTGGCCGAGTTGGATATTGAATCCATGTCAATACCCTTCATGCT
GGCAGGTCTCATGGCAGTGTCCTACGTGGTGTCAGGAAAAGCAACAGATATGTGGCTTGAA
CGGGCCGCCGACATCAGCTGGGATATGGGTGCTGCAATCACAGGAAGCAGTCGGAGGCTGG
ATGTGAAACTGGATGATGACGGAGATTTTCACTTGATTGATGATCCCGGTGTTCCATGGAAG
GTCTGGGTCCTGCGCATGTCTTGCATTGGCTTAGCCGCCCTCACGCCTTGGGCCATCGTTCCC
GCCGCTTTCGGTTATTGGCTCACTTTAAAAACAACAAAAAGAGGGGGCGTGTTTTGGGACAC
GCCATCCCCAAAACCTTGCTCAAAAGGAGACACCACTACAGGAGTCTACCGAATTATGGCTA
GAGGGATTCTTGGCACTTACCAGGCCGGCGTCGGAGTCATGTACGAGAATGTTTTCCACACA
CTATGGCACACAACTAGAGGAGCAGCCATTGTGAGTGGAGAAGGAAAATTGACGCCATACT
GGGGTAGTGTGAAAGAAGACCGCATAGCTTACGGAGGCCCATGGAGGTTTGACCGAAAATG
GAATGGAACAGATGACGTGCAAGTGATCGTGGTAGAACCGGGGAAGGGCGCAGTAAACATC
CAGACAAAACCAGGAGTGTTTCGGACTCCCTTCGGGGAGGTTGGGGCTGTTAGTCTGGATTA
CCCGCGAGGAACATCCGGCTCACCCATTCTGGATTCCAATGGAGACATTATAGGCCTATACG
GCAATGGAGTTGAGCTTGGCGATGGCTCATACGTCAGCGCCATCGTGCAGGGTGACCGTCAG
GAGGAACCAGTCCCAGAAGCTTACACCCCAAACATGTTGAGAAAGAGACAGATGACTGTGC
TAGATTTGCACCCTGGTTCAGGGAAAACCAGGAAAATTCTGCCACAAATAATTAAGGACGCT
ATCCAGCAGCGCCTAAGAACAGCTGTGTTGGCACCGACGCGGGTGGTAGCAGCAGAAATGG
CAGAAGTTTTGAGAGGGCTCCCAGTACGATATCAAACTTCAGCAGTGCAGAGAGAGCACCA
AGGGAATGAAATAGTGGATGTGATGTGCCACGCCACTCTGACCCATAGACTGATGTCACCG
AACAGAGTGCCCAACTACAACCTATTTGTCATGGATGAAGCTCATTTCACCGACCCAGCCAG
```

FIG. 18. Cont.

TATAGCCGCACGAGGATACATTGCTACCAAGGTGGAATTAGGGGAGGCAGCAGCCATCTTT
ATGACAGCGACCCCGCCTGGAACCACGGATCCTTTTCCTGACTCAAATGCCCCAATCCATGA
TTTGCAAGATGAGATACCAGACAGGGCATGGAGCAGTGGATACGAATGGATCACAGAATAT
GCGGGTAAAACCGTGTGGTTTGTGGCGAGCGTAAAAATGGGGAATGAGATTGCAATGTGCC
TCCAAAGAGCGGGGAAAAAGGTCATCCAACTCAACCGCAAGTCCTATGACACAGAATACCC
AAAATGTAAGAATGGAGACTGGGATTTTGTCATTACCACCGACATCTCTGAAATGGGGGCCA
ACTTCGGTGCGAGCAGGGTCATCGACTGTAGAAAGAGCGTGAAACCCACCATCTTAGAAGA
GGGAGAAGGCAGAGTCATCCTCGGAAACCCATCTCCCATAACCAGTGCAAGCGCAGCTCAA
CGGAGGGGCAGAGTAGGCAGAAACCCCAATCAAGTTGGAGATGAATACCACTATGGGGGG
GCTACCAGTGAAGATGACAGTAACCTAGCCCATTGGACAGAGGCAAAGATCATGTTAGACA
ACATACACATGCCCAATGGACTGGTGGCCCAGCTCTATGGACCAGAGAGGGAAAAGGCTTT
CACAATGGATGGCGAATACCGTCTCAGAGGTGAAGAAAAGAAAAACTTCTTAGAGCTGCTT
AGGACGGCTGACCTCCCGGTGTGGCTGGCCTACAAGGTGGCGTCCAATGGCATTCAGTACAC
CGACAGAAAGTGGTGTTTTGATGGGCCGCGTACGAATGCCATACTGGAGGACAACACCGAG
GTAGAGATAGTCACCCGGATGGGTGAGAGGAAAATCCTCAAGCCGAGATGGCTTGATGCAA
GAGTTTATGCAGATCACCAGGCCCTCAAGTGGTTCAAAGACTTTGCAGCAGGGAAGAGATC
AGCCGTTAGCTTCATAGAGGTGCTCGGTCGCATGCCTGAGCATTTCATGGGAAAGACGCGGG
AAGCTTTAGACACCATGTACTTGGTTGCAACGGCTGAGAAAGGTGGGAAAGCACACCGAAT
GGCTCTCGAAGAGCTGCCAGATGCACTGGAAACCATCACACTTATTGTCGCCATTACTGTGA
TGACAGGAGGATTCTTCCTACTAATGATGCAGCGAAAGGGTATAGGGAAGATGGGTCTTGG
AGCTCTAGTGCTCACACTAGCTACCTTCTTCCTGTGGGCGGCAGAGGTTCCTGGAACCAAAA
TAGCAGGGACCCTGCTGATCGCCCTGCTGCTGATGGTGGTTCTCATCCCAGAACCGGAAAAA
CAGAGGTCACAGACAGATAACCAACTGGCGGTGTTTCTCATCTGTGTCTTGACCGTGGTTGG
AGTGGTGGCAGCAAACGAGTACGGGATGCTAGAAAAAACCAAAGCGGATCTCAAGAGCAT
GTTTGGCGGAAAGACGCAGGCATCAGGACTGACTGGATTGCCAAGCATGGCACTGGACCTG
CGTCCAGCCACAGCCTGGGCACTGTATGGGGGAGCACAGTCGTGCTAACCCCTCTTCTGAA
GCACCTGATCACGTCGGAATACGTCACCACATCGCTAGCTTCAATTAACTCACAAGCTGGCT
CATTATTCGTCTTGCCACGAGGCGTGCCTTTTACCGACCTAGACTTGACTGTTGGCCTCGTCT
TCCTTGGCTGTTGGGGTCAAGTCACCCTCACAACGTTTCTGACAGCCATGGTTCTGGCGACA
CTTCACTATGGGTACATGCTCCCTGGTTGGCAAGCAGAAGCACTCAGGGCTGCCCAGAGAAG
GACAGCGGCTGGAATAATGAAGAATGCCGTTGTTGACGGAATGGTCGCCACTGATGTGCCT
GAACTGGAAAGGACTACTCCTCTGATGCAAAAGAAAGTCGGACAGGTGCTCCTCATAGGGG
TAAGCGTGGCAGCGTTCCTCGTCAACCCTAATGTCACCACTGTGAGAGAAGCAGGGGTGTTG
GTGACGGCGGCTACGCTTACTTTGTGGGACAATGGAGCCAGTGCCGTTTGGAATTCCACCAC
AGCCACGGGACTCTGCCATGTCATGCGAGGTAGCTACCTGGCTGGAGGCTCCATTGCTTGGA
CTCTCATCAAGAACGCTAATAAGCCCTCCTTGAAAAGGGGAAGGCCTGGGGCAGGACGCT
AGGGGAGCAGTGGAAGGAAAAACTAAATGCCATGAGTAGAGAAGAGTTTTTTAAATACCGG
AGAGAGGCCATAATCGAGGTGGACCGCACTGAAGCACGCAGGGCCAGACGTGAAAATAAC
ATAGTGGGAGGACATCCGGTTTCGCGAGGCTCAGCAAAACTCCGTTGGCTCGTGGAGAAAG
GATTTGTCTCGCCAATAGGAAAAGTCATTGATCTAGGGTGTGGGCGTGGAGGATGGAGCTAC
TACGCAGCAACCCTGAAGAAGGTCCAGGAAGTCAGAGGATACACGAAAGGTGGGGCGGGA
CATGAAGAACCGATGCTCATGCAGAGCTACGGCTGGAACCTGGTCTCCCTGAAGAGTGGAG
TGGACGTGTTTTACAAACCTTCAGAGCCCAGTGATACCCTGTTCTGTGACATAGGGGAATCC
TCCCCAAGTCCAGAAGTAGAAGAACAACGCACACTACGCGTCCTAGAGATGACATCTGACT

FIG. 18. Cont.

```
GGTTGCACCGAGGACCTAGAGAGTTCTGCATTAAAGTTCTCTGCCCTTACATGCCCAAGGTT
ATAGAAAAAATGGAAGTTCTGCAGCGTCGCTTCGGAGGTGGGCTAGTGCGTCTCCCCTGTC
CCGAAACTCCAATCACGAGATGTATTGGGTTAGTGGAGCCGCTGGCAATGTGGTGCACGCTG
TGAACATGACCAGCCAGGTATTACTGGGGCGAATGGATCGCACAGTGTGGAGAGGGCCAAA
GTATGAGGAAGATGTCAACCTAGGGAGCGGAACAAGAGCCGTGGGAAAGGGAGAAGTCCA
TAGCAATCAGGAGAAAATCAAGAAGAGAATCCAGAAGCTTAAAGAAGAATTCGCCACAAC
GTGGCACAAAGACCCTGAGCATCCATACCGCACTTGGACATACCACGGAAGCTATGAAGTG
AAGGCTACTGGCTCAGCCAGCTCTCTCGTCAACGGAGTGGTGAAGCTCATGAGCAAACCTTG
GGACGCCATTGCCAACGTCACCACCATGGCCATGACTGACACCACCCCTTTTGGACAGCAAA
GAGTTTTCAAGGAGAAAGTTGACACGAAGGCTCCTGAGCCACCAGCTGGAGCCAAGGAAGT
GCTCAACGAGACCACCAACTGGCTGTGGGCCTACTTGTCACGGGAAAAAGACCCCGCTTGT
GCACCAAGGAAGAATTCATTAAGAAAGTTAACAGCAACGCGGCTCTTGGAGCAGTGTTCGC
TGAACAGAATCAATGGAGCACGGCGCGTGAGGCTGTGGATGACCCGCGGTTTTGGGAGATG
GTTGATGAAGAGAGGGAAAACCATCTGCGAGGAGAGTGTCACACATGTATCTACAACATGA
TGGGAAAAAGAGAAGAAGCCTGGAGAGTTTGGAAAAGCTAAAGGAAGCAGGGCCATTT
GGTTCATGTGGCTTGGAGCACGGTATCTAGAGTTTGAAGCTTTGGGGTTCCTGAATGAAGAC
CATTGGCTGAGCCGAGAGAATTCAGGAGGTGGAGTGGAAGGCTCAGGCGTCCAAAAGCTGG
GATACATCCTCCGTGACATAGCAGGAAAGCAAGGAGGGAAAATGTACGCTGATGATACCGC
CGGGTGGGACACTAGAATTACCAGAACTGATTTAGAAAATGAAGCTAAGGTACTGGAGCTC
CTAGACGGTGAACACCGCATGCTCGCCCGAGCCATAATTGAACTGACTTACAGGCACAAAG
TGGTCAAGGTCATGAGACCTGCAGCAGAAGGAAAGACCGTGATGGACGTGATATCAAGAGA
AGATCAAAGGGGGAGTGGACAGGTGGTCACTTATGCTCTTAACACTTTCACGAACATCGCTG
TCCAGCTCGTCAGGCTGATGGAGGCTGAGGGGGTCATTGGACCACAACACTTGGAACATCTA
CCTAGGAAAAACAAGATAGCTGTCAGGACCTGGCTCTTTGAGAATGGAGAGGAGAGAGTGA
CCAGGATGGCGATCAGCGGAGACGACTGTGCCGTCAAACCGCTGGACGACAGATTCGCCAC
AGCCCTCCACTTCCTCAACGCAATGTCAAAGGTCAGAAAAGACATCCAGGAATGGAAGCCT
TCGCATGGCTGGCACGATTGGCAGCAAGTTCCCTTCTGTTCTAACCATTTTCAGGAGATTGTG
ATGAAAGATGGAAGGAGTATAGTTGTCCCGTGCAGAGGACAGGATGAGCTGATAGGCAGGG
CTCGCATCTCTCCAGGAGCTGGATGGAATGTGAAGGACACAGCTTGCCTGGCCAAAGCATAT
GCACAGATGTGGCTACTCCTATACTTCCATCGCAGGGACTTGCGTCTCATGGCAAATGCGAT
TTGCTCAGCAGTGCCAGTAGATTGGGTGCCCACAGGCAGGACATCCTGGTCAATACACTCGA
AAGGAGAGTGGATGACCACGGAAGACATGCTGCAGGTCTGGAACAGAGTTTGGATTGAAGA
AAATGAATGGATGATGGACAAGACTCCAATCACAAGCTGGACAGACGTTCCGTATGTGGGA
AAGCGCGAGGACATCTGGTGTGGCAGCCTCATCGGAACGCGATCCAGAGCAACCTGGGCTG
AGAACATCTATGCGGCGATAAACCAGGTTAGAGCTGTCATTGGGAAAGAAAATTATGTTGA
CTACATGACCTCACTCAGGAGATACGAAGACGTCTTGATCCAGGAAGACAGGGTCATCTAGT
GTGATTTAAGGTAGAAAAGTAGACTATGTAAACAATGTAAATGAGAAAATGCATGCATATG
GAGTCAGGCCAGCAAAAGCTGCCACCGGATACTGGGTAGACGGTGCTGCCTGCGTCTCAGT
CCCAGGAGGACTGGGTTAACAAATCTGACAACAGAAAGTGAGAAAGCCCTCAGAACCGTCT
CGGAAGTAGGTCCCTGCTCACTGGAAGTTGAAAGACCAACGTCAGGCCACAAATTTGTGCC
ACTCCGCTAGGGAGTGCGGCCTGCGCAGCCCAGGAGGACTGGGTTACCAAAGCCGTTGAG
GCCCCCACGGCCCAAGCCTCGTCTAGGATGCAATAGACGAGGTGTAAGGACTAGAGGTTAG
AGGAGACCCCGTGGAAACAACAACATGCGGCCCAAGCCCCTCGAAGCTGTAGAGGAGGTG
GAAGGACTAGAGGTTAGAGGAGACCCCGCATTTGCATCAAACAGCATATTGACACCTGGGA
```

FIG. 18. Cont.

ATAGACTGGGAGATCTTCTGCTCTATCTCAACATCAGCTACTAGGCACAGAGCGCCGAAGTA
TGTAGCTGGTGGTGAGGAAGAACACAGGATCT

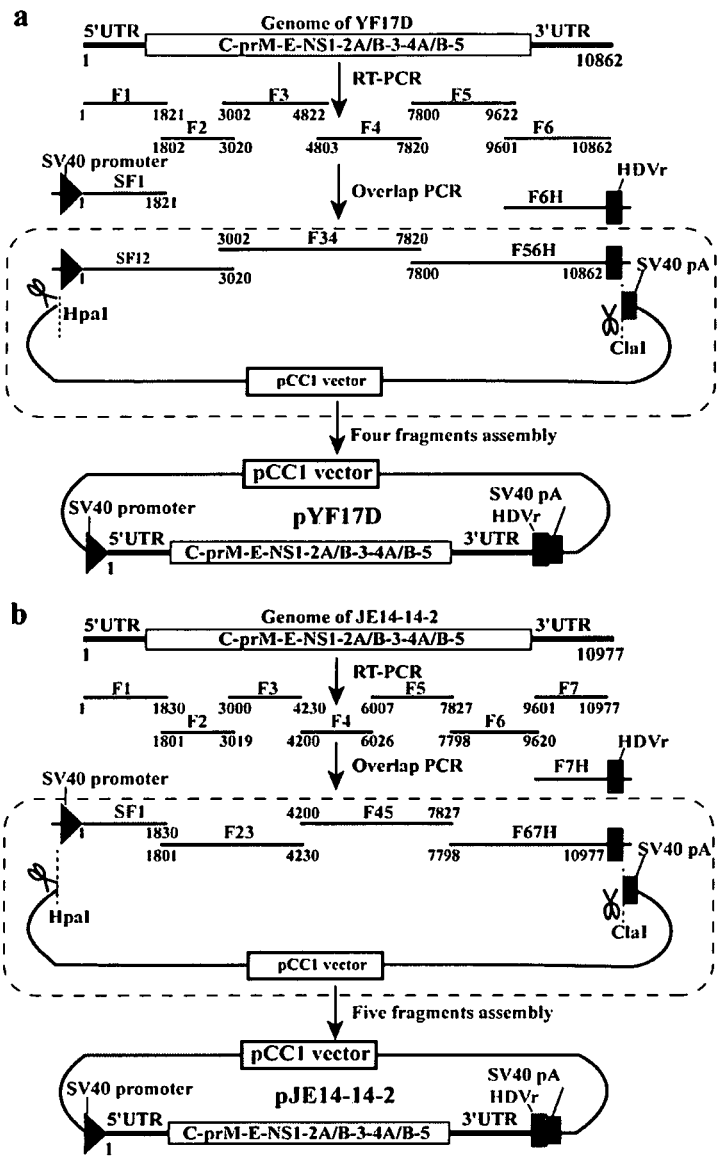
FIG 19A-B

FIG 20A-B a

Infect Vero cells with JE14-14-2 P0 (MOI=0.1) in a T-25 flask
↓
Add 50 μl supernatant for next round of infection
P1 --> P5 (3~5 days per passage based on CPE)
↓
Collect P5 virus for plaque assay and RT-PCR &
Full-genome sequencing b

P0   P1   P2   P3   P4   P5 c

CATCGAATAC          GGCACAGTTT
K136E (AAA-GAA)     K166Q (AAG-CAG)

DNA PLASMID-LAUNCHED LIVE-ATTANUATED VACCINES FOR PLUS-SENSE SINGEL STRANDED RNA

FIELD OF THE INVENTION

The invention generally relates to the development of a DNA-launched live-attenuated vaccine (LAV) for plus-sense single stranded RNA viruses and compositions comprising the vaccine. The vaccines may be used in humans and animals for treating or providing immunoprotection against plus-sense single stranded RNA viruses such as ZIKA virus (ZIKV), yellow fever virus and Japanese encephalitis.

BACKGROUND OF THE INVENTION

The genus Flavivirus of the family Flaviviridae comprises over 70 viruses, many of which are arthropod-borne and significant viral pathogens, including dengue (DENV), yellow fever (YFV), Japanese encephalitis (JEV), West Nile (WNV), Zika (ZIKV), St. Louis encephalitis (SLEV), and tick-borne encephalitis (TBEV) viruses. The four serotypes of DENV alone affect over 3 billion people living in the tropics and subtropics, leading to 390 million human infections each year [48]. YFV poses risks to 900 million people living in 44 endemic countries of Latin America and Africa and kills around 60,000 people annually [49]. JEV is the most common cause of encephalitis in Asia, resulting in approximately 68,000 clinical cases and 13,600 to 20,400 deaths each year [50]. ZIKV emerged recently and infected over 700,000 humans, causing devastating congenital Zika syndromes (CZS) in the fetuses born to infected pregnant women [51].

Besides mosquito vector control, vaccine and antiviral are two important means to control and treat flavivirus infections. Despite major effort has been made to develop antivirals, there is currently no specific flavivirus therapeutics [52]. Clinically approved vaccines are available for flaviviruses, including YFV (live-attenuated vaccine), JEV (both inactivated and live-attenuated vaccines), TBEV (inactivated vaccine), and DENV (chimeric live-attenuated vaccine) [53]. Flaviviruses have a positive-sense, single-stranded RNA genome of about 11,000 nucleotides. The viral genome consists of a 5' untranslated region (UTR), a single open-reading frame, and a 3' UTR. The long open-reading frame encodes three structural (capsid [C], precursor membrane [prM], and envelope [E]) and seven non-structural (NS1, NS2A, NS2B, NS3, NS4A, NS4B, and NS5) proteins. Together with the genomic RNA, the structural proteins form viral particles. The nonstructural proteins participate in viral replication, virion assembly, and evasion of host immune response [54]. Reverse genetic systems have been well developed for different flaviviruses to study viral replication, pathogenesis, vaccine, and antiviral development [55-61].

Vaccines have saved millions of lives through controlling and preventing infectious diseases. Compared with the inactivated and subunit vaccines, live-attenuated vaccines (LAVs) have the advantage of rapid immune response, potentially single dose, and durable protection. Successful LAVs for viral pathogens include smallpox, polio, measles, mumps, rubella, rotavirus, chickenpox, yellow fever, Japanese encephalitis 14-14-2, and influenza nasal spray vaccines. The LAVs are usually manufactured in cells, eggs, or animals and transported to clinics through a "cold chain." The LAV production in cells or eggs requires dedicated manufacture facility and has the risk of adventitious agent contamination. The requirement of "cold chain" for transportation and storage of LAVs could account for 80% of the vaccine cost in warm climates [62]. Thus, new platforms that can overcome these limitations will significantly reduce the cost and increase the accessibility of LAVs. RNA platform has recently emerged as a promising means to launch non-replicative RNA or self-amplifying viral RNA (i.e., LAV or replicon) [63]. Once the LAV or replicon RNA is delivered into cells, it translates and replicates, leading to efficient expression of antigens. Recent studies showed that 10-100 ng of alphavirus LAV RNA or replicon-based RNA (expressing ZIKV prM-E genes) elicited 100% seroconversion and protection against Venezuelan equine encephalitis virus (VEEV) and Zika virus (ZIKV) [64, 65]. Besides the self-amplifying viral RNA, non-amplifying mRNA platform could also be used to launch subunit vaccines, as evidenced by the recent ZIKV prM-E subunit vaccines [66-68].

The Flavivirus genome is about 11,000 nucleotides in length and contains a 5' untranslated region (UTR), a long open-reading frame, and a 3' UTR. The single open-reading frame encodes three structural (capsid [C], precursor membrane [prM] and envelope [E]) and seven non-structural (NS1, NS2A, NS2B, NS3, NS4A, NS4B and NS5) proteins. The structural proteins, together with the genomic RNA, form viral particles. The nonstructural proteins participate in viral replication, virion assembly, and evasion of the host innate immune response [1]. The flaviviral 3' UTR ranges in length from about 400 to 600 nucleotides, and is highly structured with regions conserved between species.

ZIKV was first identified from a sentinel rhesus macaque in the Zika Forest of Uganda in 1947 [2]. Before 2007, ZIKV had silently circulated between primates and mosquitoes in the forests in Africa and Southeast Asia without causing detectable outbreaks or severe human diseases. Symptomatic ZIKV infection produces mild manifestations, such as fever, headaches, lethargy, conjunctivitis, rash, arthralgia, and myalgia [3]. However, from 2007 to 2016, ZIKV emerged explosively to cause a series of epidemics in Africa, Micronesia, the South Pacific, and the Americas, leading to more than 700,000 documented autochthonous human infections [4, 5]. Importantly, during the recent epidemics, ZIKV caused the newly described devastating congenital Zika syndromes (CZS), including microcephaly, craniofacial disproportion, spasticity, ocular abnormalities, and miscarriage [6]. CZS was found in 6-11% of the fetuses from ZIKV-infected pregnant women [7]. In adults, Zika infection can cause Guillain-Barré syndrome (GBS; an autoimmune disease that leads to muscle weakness and paralysis) at an incidence of 1 in 4,000-to-5,000 infected adults [8]. From February to November of 2016, the World Health Organization (WHO) declared ZIKV-related CZS as a Public Health Emergency of International Concern [4].

In response to the ZIKV epidemics, intensive efforts have been made to develop countermeasures, including vaccines and antivirals, with vaccines showing great promise [9-11]. Three types of vaccines are being pursued: (i) Inactivated vaccine. Two doses of a formalin-inactivated ZIKV vaccine elicited protective levels of neutralizing antibodies in phase I clinical trials [12, 13]. (ii) Subunit vaccine. Subunit vaccines express the viral prM-E proteins from DNA, mRNA, or viral vectors (including measles virus, vesicular stomatitis virus, adenovirus, and modified vaccinia virus) [14-19]. Three-dose immunizations of DNA subunit vaccines induced protective humoral and cellular immune responses in phase I clinical trials [20, 21]. (iii) Live-attenuated vaccine (LAV). Both attenuation of wild-type (WT) ZIKV and chimeric flavivirus approaches have been pursued to develop LAVs. For the former, LAV candidates containing a 3'UTR deletion showed excellent safety and potency in mouse and non-human primate (NHP) models [22, 23]. For the latter approach, chimeric DENV-2 and JEV SA14-14-2 with swapped ZIKV prM-E genes were reported to protect mice and/or NHPs from ZIKV infection after a single-dose vaccination [24, 25].

Different vaccine platforms have distinct features. Compared with LAVs, DNA vaccines are chemically stable and do not require a cold chain. However, traditional DNA vaccines expressing viral antigens usually require multiple doses, and the immune responses observed in animal models have generally not been reproduced in humans [26]. In contrast, LAVs usually have the advantages of single dose, quick immunity, and durable protection. However, the manufacture and transport of LAVs require cell culture (or eggs) and a cold chain. The cold chain alone can account for 80% of the vaccine cost in warm climates where emerging viruses are typically endemic [27]. Thus, a DNA-launched LAV has the potential to combine the strengths and to eliminate the weaknesses of both vaccine platforms. These improvements are of practical importance and could transform future vaccine development.

Vaccines, especially live-attenuated vaccines (LAV), are the most effective way to control and prevent infectious diseases. LAVs have the advantages of single dose, rapid immune onset, and long-lasting protection. DNA vaccine has the advantages of chemical stability, ease of production, and no "cold chain" requirement during storage and transportation. Combining the strengths of LAV and DNA vaccine could transform the practice of conventional LAV by eliminating vaccine production on cell culture (or eggs) or "cold chain" requirement.

Herein we disclose application of the plasmid DNA-launched LAV (pLAV) platform to two clinically approved flavivirus LAVs: YF17D and JE14-14-2. For both LAVs, a single-dose immunization as low as 300 ng of pLAV conferred 100% seroconversion and full protection against viral challenge in mouse models. Although the animals did not develop detectable viremia, disease, or weight loss, they developed robust neutralizing antibody titers, which did not increase after viral challenge. The results indicate that the pLAV platform may be used as a universal technology to deliver LAVs for plus-strand RNA viruses.

The present invention addresses the need for providing methods for producing live attenuated vaccines of improved stability and immunogenicity against positive-strand RNA viruses with global public health impact such as flaviviruses. To achieve this goal, we have developed a single-dose DNA-launched LAV that induces immunity which prevents ZIKV vertical transmission and testis damage in mice.

BRIEF SUMMARY OF THE INVENTION

The invention relates to an immunogenic composition comprising a cDNA copy of the genome of a live-attenuated plus-sense single-stranded RNA virus wherein such viral genome optionally comprises at least one mutation which attenuates or reduces the virulency of said single-stranded RNA virus in a susceptible host e.g., wherein said mutations include substitution, deletion and addition mutations which elicit the production of neutralizing antibodies in a susceptible host and/or elicit a protective T cell immune response in a susceptible host.

The invention relates to an immunogenic composition as above-described wherein the live-attenuated plus-sense single-stranded RNA virus is a live-attenuated flavivirus, e.g., wherein the live-attenuated plus-sense single-stranded RNA virus is a live-attenuated ZIKA virus (ZIKV), dengue virus (DENV), yellow fever virus (YFV), West Nile virus (WNV), Japanese encephalitis virus (JEV), or tick-borne encephalitis virus (TBEV) or comprises a live-attenuated plus-sense single-stranded RNA virus is a live-attenuated ZIKA virus (ZIKV) and/or wherein the live-attenuated plus-sense single-stranded RNA virus is a live-attenuated yellow fever virus (YFV) and/or wherein the live-attenuated plus-sense single-stranded RNA virus is a live-attenuated Japanese encephalitis virus (JEV).

The invention further relates to the immunogenic composition of any one of the foregoing, wherein the genome of the live-attenuated plus-sense single-stranded RNA virus comprises a deletion in the 3' untranslated region (3'UTR) of the genome which attenuates or reduces the virulency of said single-stranded RNA virus in a susceptible host, e.g., wherein the genome of the live-attenuated plus-sense single-stranded RNA virus comprises a deletion in the 3' untranslated region (3'UTR) of the genome which attenuates or reduces the virulency of said single-stranded RNA virus in a susceptible host and/or comprising a 3'UTR deletion ranges in size from about 5 to 40 nucleotides and/or comprising a 3'UTR deletion which comprises a 10-nucleotide deletion, a 20-nucleotide deletion, or a 30-nucleotide deletion ±1, 2, 3, 4, 5, 6, 7, 8, 9 or 10 nucleotides or a 20-nucleotide deletion and/or wherein the virus is ZIKV and the 3'UTR deletion is a deletion of the nucleotides at positions 10640 to 10659 of the full-length genomic sequence.

The invention further relates to the immunogenic composition of any one of the foregoing, wherein the genome of the live-attenuated plus-sense single-stranded RNA virus in the plasmid comprises the genome of an attenuated JEV strain, e.g., JE14-14-2 having the sequence in FIG. 18 (SEQ ID NO: 1) or comprises the genome of an attenuated YFV strain, e.g., YF17D and optionally expresses the LAV under the control of a eukaryotic or viral promotor.

The invention further relates to the immunogenic composition of any one of the foregoing, which comprises at least one pharmaceutically acceptable carrier or excipient and/or adjuvant, e.g., one suitable for parenteral or enteral administration and/or via injection such as intramuscular, intravenous, subcutaneous and/or optionally further including a subsequent electroporation.

The invention further relates to a method of eliciting an immune response in a susceptible subject by administering a prophylactically or therapeutically effective amount of an immunogenic composition according to any one of the foregoing.

The invention further relates to a method of eliciting an immune response in a susceptible subject by administering a prophylactically or therapeutically effective amount of an immunogenic composition according to any one of the foregoing which (i) induces a CD8+ T cell response, an antibody response, and/or a cellular immune response against the plus-sense single stranded RNA virus; (ii) produces a neutralizing antibody titer equivalent to that of wildtype plus-sense single stranded RNA virus infection; and/or (iv) prevents viremia in a susceptible subject after subsequent challenge with a wildtype plus-sense single stranded RNA virus strain.

The invention further relates to a method of eliciting an immune response in a susceptible subject by administering a prophylactically or therapeutically effective amount of an immunogenic composition according to any one of the foregoing, which (i) induces a CD8+ T cell response, an antibody response, and/or a cellular immune response against ZIKV; (ii) produces a neutralizing antibody titer equivalent to that of wildtype ZIKV infection; (iii) is used to prevent congenital ZIKV syndrome and/or microcephaly; and/or (iv) prevents viremia in said subject after subsequent challenge with a wildtype ZIKV strain.

The invention further relates to a method of eliciting an immune response in a susceptible subject by administering a prophylactically or therapeutically effective amount of an immunogenic composition according to any one of the foregoing, which (i) induces a CD8+ T cell response, an antibody response, and/or a cellular immune response against JEV; (ii) produces a neutralizing antibody titer equivalent to that of wildtype JEV infection; (iii) is used to prevent JEV mediated encephalitis or weight loss; and/or (iv) prevents viremia in said subject after subsequent challenge with a wildtype JEV strain or JE14-14-2.

The invention further relates to a method of eliciting an immune response in a susceptible subject by administering a prophylactically or therapeutically effective amount of an immunogenic composition according to any one of the foregoing which (i) induces a CD8+ T cell response, an antibody response, and/or a cellular immune response against YFV; (ii) produces a neutralizing antibody titer equivalent to that of wildtype YFV infection; (iii) is used to prevent YFV mediated fever or weight loss; and/or (iv) prevents viremia in said subject after subsequent challenge with a wildtype YFV strain or YFV17D.

The invention further relates to a method of eliciting an immune response in a susceptible subject by administering a prophylactically or therapeutically effective amount of an immunogenic composition according to any one of the foregoing wherein the susceptible subject is a human and/or a pregnant female.

The invention further relates to a method of eliciting an immune response in a susceptible subject by administering a prophylactically or therapeutically effective amount of an immunogenic composition according to any one of the foregoing, wherein the susceptible subject has never been exposed to the virus.

The invention further relates to a method of eliciting an immune response in a susceptible subject by administering a prophylactically or therapeutically effective amount of an immunogenic composition according to any one of the foregoing, wherein the susceptible subject has been previously exposed to the virus.

The invention further relates to a method of eliciting an immune response in a susceptible subject by administering a prophylactically or therapeutically effective amount of an immunogenic composition according to any one of the foregoing, wherein the administered immunogenic composition comprises cDNA copies of the genome of different live-attenuated plus-sense single-stranded RNA viruses wherein each of said different viral genomes optionally comprises at least one mutation which attenuates or reduces the virulency of said single-stranded RNA virus in a susceptible host, e.g., wherein the genomes of said different live-attenuated plus-sense single-stranded RNA viruses in the administered immunogenic composition are derived from different flaviviruses and/or different strains of a specific flavivirus, e.g., ZIKV, YFV, or JEV.

The invention further relates to methods of providing prolonged immunity against a flavivirus comprising administering a single or multiple doses of a plasmid comprising a cDNA encoding live attenuated strain of said flavivirus.

The invention further relates to methods of providing prolonged immunity against YFV, JEV or ZIKV comprising administering a single or multiple doses of a plasmid comprising a cDNA encoding a live attenuated strain of ZIKV, YFV, or JEV, e.g., wherein the attenuated virus is YFV and the plasmid comprises a cDNA encoding YF17D (accession number JN628279.1) which optionally comprises at least one mutation and/or the viral cDNA in the plasmid comprises JE14-14-2, optionally which comprises at least one mutation optionally a K136E or K166Q mutation.

The invention further relates to methods of providing prolonged immunity against YFV, JEV or ZIKV comprising administering a single or multiple doses of a plasmid comprising a cDNA encoding a live attenuated strain of a flavivirus, e.g., ZIKV, YFV, or JEV, wherein the virus cDNA is expressed under the control of a eukaryotic or viral promoter, e.g., the SV40 promoter and/or comprises a hepatitis delta virus ribozyme (HDVr) and a polyadenylation signal engineered at the 3' end of the viral cDNA and/or the plasmid comprising the virus cDNA is one that provides for low copy number and optionally copy number control, e.g., pCC1.

The invention further relates to methods of providing prolonged immunity against YFV, JEV or ZIKV comprising administering a single or multiple doses of a plasmid comprising a cDNA encoding a live attenuated strain of ZIKV, YFV, or JEV, wherein the plasmid comprising the cDNA encoding the attenuated viral DNA flavivirus is administered by injection, e.g., intramuscularly and optionally further including an electroporation step after injection.

The invention further relates to methods of providing prolonged immunity against YFV, JEV or ZIKV comprising administering a single or multiple doses of a plasmid comprising a cDNA encoding a live attenuated strain of ZIKV, YFV, or JEV, wherein the virus immunizing dose is as low as 300 ng or 500 ng of pLAV.

In some embodiments, the at least one mutation which attenuates or reduces the virulency of said single-stranded RNA virus in a susceptible host includes one or more substitution, deletion and addition mutations.

In certain aspects, the immunogenic composition elicits the production of neutralizing antibodies in a susceptible host.

In certain embodiments, the immunogenic composition elicits a protective T cell immune response in a susceptible host.

In certain embodiments, the immunogenic composition elicits the production of neutralizing antibodies and a protective T cell immune response in a susceptible host.

In other embodiments, the live-attenuated plus-sense single-stranded RNA virus is a live-attenuated flavivirus.

In certain aspects the live-attenuated plus-sense single-stranded RNA virus is a live-attenuated ZIKA virus (ZIKV), dengue virus (DENV), yellow fever virus (YFV), West Nile virus (WNV), Japanese encephalitis virus (JEV), or tick-borne encephalitis virus (TBEV).

In yet another embodiment the live-attenuated plus-sense single-stranded RNA virus is a live-attenuated yellow fever virus, e.g., derived from clinical strain YF17D or a variant thereof.

In yet another embodiment the live-attenuated plus-sense single-stranded RNA virus is a live-attenuated Japanese encephalitis virus, e.g., clinical strain JE14-14-2 or a variant thereof.

In yet another embodiment the live-attenuated plus-sense single-stranded RNA virus is a live-attenuated ZIKA virus (ZIKV).

In some embodiments the genome of the live-attenuated plus-sense single-stranded RNA virus comprises a deletion in the 3' untranslated region (3'UTR) of the genome which attenuates or reduces the virulency of said single-stranded RNA virus in a susceptible host.

In certain aspects the 3'UTR deletion ranges in size from about 5 to 40 nucleotides.

In other embodiments the 3'UTR deletion comprises a 10-nucleotide deletion, a 20-nucleotide deletion, or a 30-nucleotide deletion ±1, 2, 3, 4, 5, 6, 7, 8, 9 or 10 nucleotides.

In yet another embodiment the 3'UTR deletion is a 20-nucleotide deletion.

In yet another embodiment the 3'UTR deletion is a 20-nucleotide deletion deletion of the nucleotides at positions 10640 to 10659 of the full-length genomic sequence.

In some embodiments the cDNA copy is comprised in a DNA plasmid.

Optionally, the DNA plasmid is an expression vector comprising a eukaryotic or viral promoter.

In certain aspects the immunogenic composition comprises at least one pharmaceutically acceptable carrier or excipient and/or adjuvant.

In some embodiments the immunogenic composition is suitable for parenteral or enteral administration.

In some embodiments, the administered immunogenic composition comprises cDNA copies of the genome of different live-attenuated plus-sense single-stranded RNA viruses wherein each of said different viral genomes optionally comprises at least one mutation which attenuates or reduces the virulency of said single-stranded RNA virus in a susceptible host.

In certain aspects, the genomes of the different live-attenuated plus-sense single-stranded RNA viruses in the administered immunogenic composition are derived from different flaviviruses and/or different strains of a specific flavivirus, e.g., ZIKV, Japanese encephalitis virus and/or yellow fever virus.

BRIEF DESCRIPTION OF THE DRAWINGS

FIG. 12 contains a comparison of the relative sensitivity of plaque and RT-PCR assays. Different amounts of WT ZIKV were measured by plaque and RT-PCR assays. The plot shows the relative correlation and sensitivity of the two assays. Coefficient of determination ($R^2$) was determined using linear regression analysis. The limits of detection of plaque and RT-PCR assays are 10 PFU/ml and 500 RNA copy/ml, respectively.

FIG. 13A-D contains experimental results characterizing pYF17D and pJE14-14-2 in cell culture. (A) Plasmid scheme of pYF17D and pJE14-14-2. Vector plasmid pCC1™ was engineered with an SV40 promoter, YF17D or JE14-14-2 cDNA, hepatitis delta virus ribozyme (HDVr), and SV40 polyadenylation (pA) signal sequence. (B-C) LAV production in cell culture. Vero and BHK-21 cells were transfected with pYF17D and pJE14-14-2 DNA (4 µg), respectively. Culture supernatants were quantified for LAVs by plaque assay. Dotted lines indicate the limit of detection (L.O.D.). (D) Plaque morphologies of YF17D and JE14-14-2 LAVs.

FIG. 14A-F contains experimental results characterizing JE14-14-2 and YF17D LAVs in A129 mice. Nine-week-old A129 mice were subcutaneously infected with $10^4$ PFU of JE14-14-2 or 105 PFU of YF17D LAV. The infected mice were monitored for weight loss (A, D), mortality (B, E), and viremia (C, F). Viremia was quantified by plaque assay on BHK-21 cells.

FIG. 15A-E contains experimental results relating to the vaccination and efficacy of pYF17D in A129 mice. (A) Experimental design. Nine-week-old A129 mice were intramuscularly vaccinated with 1, 0.3, or 0.1 µg of pYF17D using DNA delivery device TriGrid™. YF17D LAV and PBS were included as controls. (B) Weight changes of vaccinated mice. (C) Neutralizing antibody titers at days 14 and 21 post-vaccination. Neutralizing titers (NT50) were determined by sera dilutions that reduced 50% of the signal from nano luciferase YFV-17D reporter virus. (D) Viremia protection after challenge. On day 21 post-vaccination (p.v.), the mice were challenged with 107 PFU of YF17D virus. Peak viremia on day 2 post-challenge was quantified by plaque assay on BHK-21 cells. (E) Post-challenge neutralizing antibody titers. On day 21 post-challenge (p.c.), mice were bled and measured for neutralizing titers using a nano luciferase YF17D reporter virus.

FIG. 16A-E contains experimental results relating to the vaccination and efficacy of pJE14-14-2 in A129 mice. (A) Experimental design. Nine-week-old A129 mice were intramuscularly vaccinated with 1, 0.3, or 0.1 µg of pJE14-14-2 using TriGrid™. JE14-14-2 LAV and PBS were included as controls. (B) Weight changes of the vaccinated mice. (C) Neutralizing antibody titers at days 14 and 21 post-vaccination. NT50 values were determined using a nano luciferase JE14-14-2 reporter virus. (D) Viremia protection after challenge. On day 21 post-vaccination, the mice were challenged with $10^4$ PFU of JE14-14-2 virus. Peak viremia on day 3 post-challenge was quantified by plaque assay on BHK-21 cells. (E) Post-challenge neutralizing antibody titers. On day 21 post-challenge, mice were bled and measured for neutralizing titers using a nano luciferase JE14-14-2 reporter virus.

FIG. 17A-D contains experimental results characterizing the stability of pYF17D and pJE14-14-2 in. (A) Passaging scheme of E. coli containing pYF17D or pJE14-14-2. E. coli colony containing pYF17D or pJE14-14-2 was inoculated into a 250-ml flask containing 50 ml LB medium with 12.5 µg/ml chloramphenicol, cultured at a 37° C. for 12 h, and continuously cultured from P1 to P5 with 1000-fold dilution. For plasmid extraction, the E. coli culture from each passage was 10-fold diluted into fresh LB medium containing 12.5 µg/ml chloramphenicol and 1×CopyControl Induction Solution. After 5 h incubation at 37° C., the culture was harvested for plasmid extraction. The resulting DNA plasmid was subjected to functional analysis. (B) Functional characterization of P0 to P5 pYF17D. P0 to P5 pYF17D DNA (4 µg) was transfected into Vero cells and quantified for infectious virus production by plaque assay. The dotted line indicates the limit of detection (L.O.D.). (C) Functional characterization of P0 to P5 pJE14-14-2. The experimental procedure is the same as described in (b). (D) Plaque morphologies of P0 to P5 YF17D and JE14-14-2 viruses.

FIG. 18 contains the genome sequence of JE14-14-2 used in Example 2.

FIG. 19A-B contains the construction schemes used to synthesize pYF17D (a) and pJE14-14-2 (b). (A) Six cDNA fragments from F1 to F6 were synthesized from genomic RNA using RT-PCR to cover the complete YF17D genome. The position of each fragment was numbered based on the sequence of YF17D virus. Overlap PCR was performed to add the sequences of SV40 promoter and HDVr to the N-terminus of 5'UTR and the C-terminus of 3'UTR, respectively. Vector plasmid pCC1 with SV40 polyA sequence was derived from digesting pZIKV-3'UTR-Δ20 [75] with HpaI and ClaI enzymes. Three overlap PCR products (SF12, F34, and F56H), together with pCC1 vector, were assembled to form the pYF17D using NEBuilder® HiFi DNA Assembly Master Mix. (B) Seven cDNA fragments from F1 to F7 were synthesized from genomic RNA using RT-PCR to cover the complete JE14-14-2 genome. The nucleotide positions of each fragment were numbered based on the sequence of JE14-14-2 virus. Four overlap PCR products (SF1, F23, F45, and F67H), together with pCC1 vector, were assembled to form the pJE14-14-2 using NEBuilder® HiFi DNA Assembly Master Mix.

FIG. 20A-B contains experimental results characterizing pJE14-14-2 on Vero cells. (A) Production of JE14-14-2 LAV after transfecting Vero cells with 4 µg of pJE14-14-2 DNA. Culture supernatants were quantified for JE14-14-2 LAV by plaque assay on BHK-21 cells. The dotted line indicates the limit of detection (L.O.D.). (B) Plaque morphology of JE14-14-2 virus recovered from Vero cells.

FIG. 21A-E contains experimental results relating to heterogeneous JE14-14-2 variants derived from Vero cells. (A) Passage scheme of JE14-14-2 LAV on Vero cells. JE14-14-2 LAV was produced from pJE14-14-2-transfected Vero cells (named as P0). The P0 virus was continuously passaged on Vero cells for 5 rounds. The P5 virus was subjected to full-genome sequencing. Two independent passaging and sequencing were performed. (B) Plaque morphologies of P0 to P5 JE14-14-2 on BHK-21 cells. (C) Sequence chromatograms of the mutated E regions. The codons for K136E and K166Q are underlined. (D) Plaque morphologies of recombinant K136E and K166I JE14-14-2. Mutation K136E or K166Q was individually introduced into the WT pJE14-14-2. The mutant pJE14-14-2 was transfected into Vero cells to produce recombinant viruses. The plaque assays were performed on BHK-21 cells. (E) Residues K136 and K166 on the crystal structure of JEV E protein (PDB coed 3P54). Residue K138, which was previously reported to be critical for neurovirulence [85], is also highlighted.

FIG. 22A-C contains experimental results showing the neurovirulence of JE14-14-2 K136E and K166Q mutants. Groups of seven-day-old outbred CD-1 pups (n=9-11) were injected intracranially with 10, $10^2$, or $10^3$ PFU of WT JE14-14-2 (A), K136E (B), and K166Q viruses (C). The infected mice were monitored daily for signs of morbidity and mortality. The survival curves are presented.

DETAILED DESCRIPTION OF THE INVENTION

Figure 1:
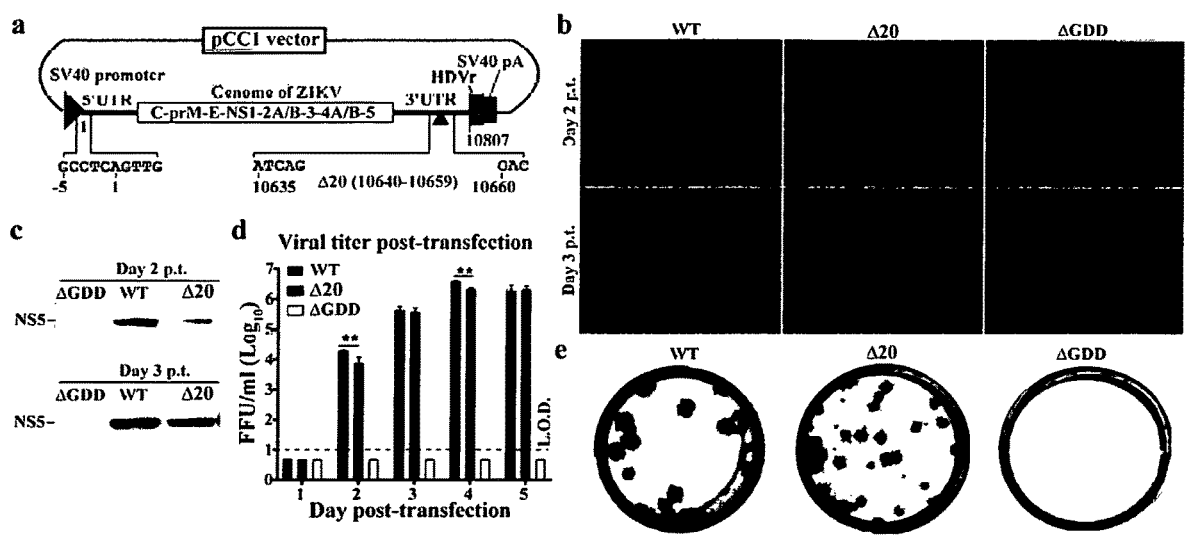
FIG. 1A-E contains a characterization of pZIKV-3'UTR-Δ20 in cell culture. (A) Diagram of plasmid pZIKV-3'UTR-Δ20. The plasmid pCC1™ vector was used to engineer a gene cassette containing a promoter from simian virus 40 (SV40), ZIKV-3'UTR-Δ20 cDNA, hepatitis delta virus ribozyme (HDVr) sequence, and SV40 polyadenylation (pA) signal element. Junction sequences are depicted between the SV40 promoter and the 5'UTR of viral genome. The 20-nucleotide deletion at the 3'UTR of ZIKV genome is indicated by a dotted line and nucleotide positions (GenBank accession No. KU955593). (B) Immunofluorescent assay (IFA). Vero cells were transfected with pZIKV-WT, pZIKV-3'UTR-Δ20 (Δ20), or pZIKV-ΔGDD (ΔGDD). At the indicated time post-transfection (p.t.), the cells were stained with 4G2 antibody to detect viral E protein expression (green). Nuclei were counterstained with DAPI (blue). (C) Western blot. The transfected Vero cells were examined for viral NS5 protein expression using Western blot. (D) Virus production post-transfection. Supernatants from the transfected Vero cells were quantified for infectious ZIKV using a focus-forming assay. The dotted line indicates the limit of detection (L.O.D.) of 10 FFU/ml. Multiple t-test was performed to analyze the statistical significances. (E) Focus-forming morphologies of WT ZIKV and ZIKV-3'UTR-Δ20 virus. No infectious virus was detected from the pZIKV-ΔGDD-transfected cells.

The present invention in general relates to the construction and characterization of a novel DNA plasmid-launched live-attenuated vaccine for plus-sense single-stranded RNA viruses having advantageous properties and the manufacture and use thereof, especially use in providing immunity against plus-sense single-stranded RNA viruses such as flaviviruses e.g. ZIKV.

As disclosed infra we applied the plasmid DNA-launched LAV (pLAV) platform to two clinically approved flavivirus LAVs: YF17D and JE14-14-2. For both LAVs, a single-dose immunization as low as 300 ng of pLAV conferred 100% seroconversion and full protection against viral challenge in mouse models. Although the animals did not develop detectable viremia, disease, or weight loss, they developed robust neutralizing antibody titers, which did not increase after viral challenge. The results indicate that the pLAV platform may be used as a universal technology to deliver LAVs for plus-strand RNA viruses.

Plasmid DNA platform represents an attractive means to launch LAVs (pLAVs) for positive-strand RNA viruses [69]. Compared with the RNA platform, DNA platform has the advantages of chemical stability, easy production, long shelf life, and no "cold chain" requirement during manufacture, transportation, and storage. However, pLAV must enter cell membrane and nucleus membrane before it can be transcribed by eukaryotic DNA-dependent RNA polymerase; compared with the RNA platform, the extra delivery barrier of nucleus membrane may contribute to a higher dose requirement for the DNA platform. The progress on DNA delivery device has enabled many DNA subunit vaccines to clinical trials. Besides expressing subunit or therapeutic proteins, DNA plasmid has been reported to launch LAVs for Kunjin virus [70], YFV 17D [71], JEV SA14-14-2 [72], chikungunya virus (CHIKV) 181/clone25 strain [73], and VEEV TC-83 strain [74]. We recently showed that a single dose of 500 ng of a ZIKV pLAV conferred 100% seroconversion and protection in both pregnant and non-pregnant mice. Unlike previous pLAV studies, all immunized mice developed sterilizing antibody titers (i.e., no increase of neutralizing titer after challenge with wild-type [WT] ZIKV) [75], highlighting the potent immunogenicity of the pLAV approach.

In this study, we expanded the DNA platform to two clinically approved flavivirus LAVs, YF17D and JE14-14-2, both of which have been safely used in more than 400 million humans [76,77]. As evidenced by the supply shortage of YF17D in 2016 when responding to the YFV outbreaks in Angola and Democratic Republic of Congo [78], conversion of the conventional LAVs to the DNA platform will enable rapid scale-up capability.

Although pLAVs were previously reported for these two vaccines [71, 72], several key immunological parameters remain to be defined. What is the minimal DNA dose required to achieve 100% seroconversion? Do the vaccinated animals achieve sterilizing neutralizing antibody titers? How do T cell respond to the pLAVs in addition to antibody immunity? Could the immunized mice be protected against challenge? What is the kinetics of LAV production at the pLAV injection site? These parameters are essential for further development of the pYF17D and pJE14-14-2 as well as for the application of the pLAV platform to new pathogens.

However, before further describing the invention in detail the following definitions are provided.

Definitions

An "adjuvant" refers to a substance that enhances an immune response, e.g., an antibody or cell-mediated immune response against a specific agent, e.g., an antigen, or an infectious agent.

An "attenuated" or "live-attenuated" virus strain refers to a mutated, modified, variant and/or recombinant virus having reduced or no virulence or pathogenicity or propensity to cause a disease or infection normally associated with the wildtype or unmodified, non-mutated virus. In general, an "attenuated" or "live-attenuated" virus has been modified to decrease or eliminate its pathogenicity, while maintaining its viability for replication within a target host and while remaining sufficiently immunogenic to prevent or inhibit wild-type viral infection and/or pathogenicity. An "attenuated" or "live-attenuated" vaccine (LAV) is a vaccine comprising an attenuated virus.

Complementary DNA ("cDNA") is DNA that is complementary to a given RNA which serves as a template for synthesis of the cDNA in a reaction that is catalyzed by reverse transcriptase. cDNA is synthesized from a single stranded RNA and may be artificially produced or naturally produced by retroviruses.

A viral "cDNA clone", "cDNA copy" or "DNA copy" is a double-stranded DNA copy of all or a portion of a viral genome, such as the RNA genome of an attenuated ZIKV. A cDNA clone is generally carried in a plasmid vector.

A "DNA plasmid-launched live-attenuated vaccine" or "DNA-launched live-attenuated vaccine" is a DNA vaccine that comprises a cDNA copy of a live-attenuated viral genome, such as the genome of a live-attenuated plus-sense single stranded RNA virus (e.g. ZIKV, yellow fever virus or Japanese encephalitis, et al.). A DNA-launched live-attenuated vaccine generally includes a eukaryotic promotor, and transcribes the full-length genomic RNA of the live-attenuated virus. The full-length viral RNA then initiates replication of live-attenuated virus in the tissues of the vaccine recipient which results in efficient immunization. The DNA-launched live-attenuated vaccine can also be used to prepare live-attenuated virus in vitro.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter. The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

In general, "identity" or "sequence identity" refers to an exact nucleotide-to-nucleotide or amino acid-to-amino acid correspondence of two polynucleotides or polypeptide sequences, respectively. Percent identity can be determined by a direct comparison of the sequence information between two molecules (the reference sequence and a sequence with unknown % identity to the reference sequence) by aligning the sequences, introducing gaps if necessary to achieve the maximum percent identity, counting the exact number of matches between the two aligned sequences, dividing by the length of the reference sequence, and multiplying the result by 100. The determination of percent identity between any two sequences can be accomplished using a mathematical algorithm. Alignment for purposes of determining percent sequence identity can be achieved in various ways that are within the skill in the art, for instance, using publicly available computer software such as BLAST, BLAST-2, BLASTN, BLASTP, ALIGN, ALIGN-2 or Megalign (DNASTAR) software. Appropriate parameters for measuring alignment, including any algorithms needed to achieve maximal alignment over the full-length of the sequences being compared can be determined by known methods. Depending on the application, the "percent identity" can exist over a region of the sequences being compared, or, alternatively, exist over the full length of the two sequences to be compared. A skilled artisan would understand that for purposes of determining sequence identity when comparing a DNA to an RNA sequence, a thymidine nucleotide is equivalent to a uracil nucleotide.

An "immunogenic composition" herein refers to a composition containing a DNA-launched live attenuated vaccine according to the invention which elicits an immune response in a susceptible host, e.g., an antibody, Th1 or cellular (e.g., T cell-mediated) immune response.

An "isolated" biological component (such as an isolated virus, bacterium or nucleic acid) refers to a component that has been substantially separated or purified away from its environment or other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "nucleic acid" and "polynucleotide" refer to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism. The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

A "pharmaceutically acceptable carrier" or "excipient" refers to compounds or materials conventionally used in immunogenic or vaccine compositions during formulation and/or to permit storage.

A "plus-sense" or "positive sense" single stranded RNA virus is a virus that uses positive sense, single-stranded RNA as its genetic material. Single stranded RNA viruses are classified as positive or negative depending on the sense or polarity of the RNA. The positive-sense viral RNA genome can also serve as messenger RNA and can be translated into protein in the host cell. Positive-sense RNA viruses account for a large fraction of known viruses, including many pathogens such as the ZIKV, chikungunya virus (CHIKV), Venezuelan equine encephalitis virus (VEEV), Japanese encephalitis virus (JEV), Yellow fever virus (YFV), hepatitis C virus, West Nile virus (WNV), dengue virus, and SARS and MERS coronaviruses, as well as less clinically serious pathogens such as the rhinoviruses that cause the common cold.

"Prophylactically effective amount" of a vaccine according to the invention refers to an amount sufficient to prevent or reduce the incidence of infection in a susceptible host, optionally as low as 300 or 500 ng of virus.

The term "recombinant" as used herein to describe a nucleic acid molecule means a polynucleotide of genomic, cDNA, viral, semisynthetic, or synthetic origin which does not occur in nature or by virtue of its origin or manipulation is associated with or linked to another polynucleotide in an arrangement not found in nature. The term "recombinant" as used with respect to a protein or polypeptide means a polypeptide produced by expression of a recombinant polynucleotide.

A "susceptible host" herein refers to a host or animal that may be infected by ZIKV or other pathogenic plus-sense single stranded RNA virus(es). Such hosts include humans or animals, e.g., a human, nonhuman primate, ape, monkey, horse, cow, carabao, goat, sheep, duck, bat, or other suitable non-human host.

"Therapeutically effective amount" of a vaccine according to the invention refers to an amount sufficient to treat infection or disease associated therewith a plus-sense single stranded RNA virus such as ZIKV in a susceptible host.

A "vaccine" composition herein refers to a composition containing a DNA-launched live-attenuated vaccine according to the invention which elicits a therapeutic or prophylactic immune response against a plus-sense single-stranded RNA virus such as ZIKV, YFV or JEV.

The terms "variant" and "mutant" refer to biologically active derivatives of the reference molecule that retain or enhance the desired activity, such as the ability to induce an immune response while reducing or eliminating virulence and pathogenicity as discussed herein.

The terms "variant" and "mutant" in reference to a polynucleotide or polypeptide refers to a polynucleotide or polypeptide that differs from the corresponding wildtype polynucleotide sequence and structure by one or more nucleic acid additions, substitutions and/or deletions, or differs from the corresponding wildtype polypeptide sequence and structure by one or more amino acid additions, substitutions and/or deletions, so long as the modifications do not destroy the desired biological activity (e.g. the ability to replicate). In general, the sequences of such variants and mutants of the invention will have a high degree of sequence identity to the reference or corresponding wildtype sequence, e.g., a nucleic acid or amino acid sequence identity of at least 40, 50, 60, 70, 80 or 85%, more particularly at least 86, 87, 88, 89, 90, 91, 92, 93, 94, 95, 96, 97, 98 or 99%, when the two sequences are aligned. For example, the nucleic acid sequence of the ZIKV cDNA copy that is a variant of the FSS13025 strain will generally have at least 40, 50, 60, 70, 80 or 85%, more particularly at least 86, 87, 88, 89, 90, 91, 92, 93, 94, 95, 96, 97, 98 or 99% sequence identity to the nucleic acid sequence of the wildtype FSS13025. Alternatively, the nucleic acid sequence of the YFV cDNA copy that is a variant of the YF17D strain will generally have at least 40, 50, 60, 70, 80 or 85%, more particularly at least 86, 87, 88, 89, 90, 91, 92, 93, 94, 95, 96, 97, 98 or 99% sequence identity to the nucleic acid sequence of the wildtype YF17D strain. Still alternatively, the nucleic acid sequence of the JEV cDNA copy that is a variant of the JE14-14-2 strain will generally have at least 40, 50, 60, 70, 80 or 85%, more particularly at least 86, 87, 88, 89, 90, 91, 92, 93, 94, 95, 96, 97, 98 or 99% sequence identity to the nucleic acid sequence of the wildtype JE14-14-2 strain. Often, the "variant" or "mutant" polypeptide sequence will include the same number of amino acids as the wildtype polypeptide but will include particular substitutions, as explained herein.

It will be appreciated by those of ordinary skill in the art that, as a result of the degeneracy of the genetic code, there are many nucleotide sequences that encode a particular polypeptide of interest as described herein. Some of these polynucleotides bear minimal homology to the nucleotide sequence of any native gene. Nonetheless, "variant" or "mutant" polynucleotides that vary due to differences in codon usage are specifically contemplated by the present invention.

The "variant" or "mutant" polypeptide sequence can include amino acid substitutions that are conservative in nature, i.e., those substitutions that take place within a family of amino acids that are related in their side chains. Specifically, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine, threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. Further one of skill in the art may readily determine regions of the molecule of interest that can tolerate change by reference to Hopp/ Woods and Kyte-Doolittle plots, well known in the art.

"ZIKV infection" or "infection elicited by ZIKV" herein refers to the infection of a susceptible host with ZIKV and diseases associated therewith, including congenital ZIKV syndrome and Guillan-Barré syndrome (GBS).

"YFV infection" or "infection elicited by YFV" herein refers to the infection of a susceptible host with YFV and diseases and symptoms associated therewith such as fever or weight loss.

JEV infection" or "infection elicited by JEV" herein refers to the infection of a susceptible host with JEV and diseases and symptoms associated therewith such as encephalitis, fever or weight loss.

As has been mentioned above the present invention provides novel DNA-launched live-attenuated vaccines for pathogenic plus-sense single stranded RNA viruses. In certain embodiments the invention relates to the construction and characterization of a vaccine comprising a DNA copy of the genome of a plus-sense single stranded RNA virus that has been modified to reduce or eliminate virulence while maintaining viability and immunogenicity (i.e. a live-attenuated virus). In certain embodiments the DNA-launched live-attenuated vaccines can be used for treating diseases related to ZIKV, YFV or JEV or providing immunoprotection against infections elicited by ZIKV, YFV or JEV, including congenital ZIKV syndrome, microcephaly, yellow fever, encephalitis, Guillan-Barré syndrome (GBS) et al. The vaccine may also prevent viremia in pregnant women and travelers to epidemic/endemic regions, avert congenital ZIKV syndrome, yellow fever or encephalitis and/or may also be useful to suppress epidemic transmission.

The genome of the live-attenuated plus-sense single stranded RNA virus, and the DNA copy thereof comprised in the DNA vaccine, includes mutations that result in the attenuation. These mutations in particular may include mutations in the 3'UTR of the viral genome. In some preferred embodiments the vaccine comprises a DNA copy of a deletion variant of ZIKV, YFV or JEV wherein a portion of the 3'UTL is deleted. In particular the deletion variant of ZIKV, YFV or JEV may comprise a 20-nucleotide deletion of the 3'UTL nucleotides, e.g., at positions 10640 to 10659 of the full-length ZIKA genome. Additional suitable live-attenuated ZIKV variants comprising 3'UTL deletions are described in WO2018/152158, the entire contents of which are incorporated by reference herein.

The live-attenuated vaccines may be derived from different plus-sense single-stranded RNA viral strains other than those embodied herein. In preferred embodiments the virus is a live-attenuated flavivirus. Flaviviruses include ZIKA virus (ZIKV), dengue virus (DENV), yellow fever virus (YFV), West Nile virus (WNV), Japanese encephalitis virus (JEV), or tick-borne encephalitis virus (TBEV).

In particular suitable viruses include any strains which are known and available in the art. Generally, the viral genomes and cDNA clones thereof will comprise the entire viral genome (modified to include the attenuating mutations). In some embodiments, the genomic sequences will have at least 40, 50, 60, 70, 80 or 85%, more particularly at least 86, 87, 88, 89, 90, 91, 92, 93, 94, 95, 96, 97, 98 or 99%, sequence identity to a wildtype genomic sequence of the corresponding virus.

In certain preferred embodiments the DNA-launched vaccines may be derived from any ZIKV, YFV or JEV and thus may comprise DNA copies of the genomes of attenuated variants of any strain of ZIKV, YFV or JEV. For example, the source of the ZIKV DNA copy can be an attenuated variant of any one of the following strains: MR766-NIID, P6-740, ArD7117, IbH_30656, ArB1362, ARB13565, ARB7701, ARB15076, ArD_41519, ArD128000, ArD158084, ArD157995, FSM, FSS13025, PHL/2012/ CPC-0740-Asian, H/PF/2013, PLCal_ZV, Haiti/1225/2014, SV0127_14_Asian, Natal_RGN_Asian, Brazil_ZKV2015_Asian, ZikaSPH2015, BeH815744, BeH819015, BeH819966, BeH823339, BeH828305, SSABR1-Asian, FLR, 103344, 8375, PRVABC59, Z1106033, MRS_OPY_Martinique, VE_Ganxian_Asian, GD01_Asian, GDZ16001, ZJO3, Rio-U1 or Rio-S1 ZIKV strains (see Wang L, et al. Cell Host Microbe. 2016 May 11; 19(5):561-5). In certain embodiments, the strain is a North American strain or a South American strain. Preferred ZIKV strains used to produce the DNA-launched live-attenuated vaccine according to the invention are FSS13025 or PRV-ABC59. An exemplary attenuated JEV strain comprises JE14-14-2 (see FIG. 18) and an exemplary attenuated YFV strain comprises YF17D.

The present invention includes expression vectors that comprise the cDNA copy of a live-attenuated virus genome of the invention. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for RNA transcription and protein expression. Other suitable vectors would be apparent to persons skilled in the art.

Preferably, a cDNA copy of a live-attenuated virus genome for use in the invention in a vector is operably linked to control sequence(s) which can provide for transcription of the RNA virus and expression of the coding sequence by the vaccine recipient. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

Promoters and other expression regulation signals may be selected to be compatible with the recipient for which expression is designed. For example, mammalian promoters include the metallothionein promoter, which can be induced in response to heavy metals such as cadmium, and the pactin promoter. Viral promoters such as the SV40 large T antigen promoter, human cytomegalovirus (CMV) immediate early (1E) promoter, rous sarcoma virus LTR promoter, adenovirus promoter), or a HPV promoter, particularly the HPV upstream regulatory region (URR) may also be used. All these promoters are readily available in the art.

In some embodiments, the cDNA copy of the live-attenuated plus-sense single stranded RNA virus (e.g. ZIKV, YFV or JEV) is contained in a plasmid, which optionally comprises a promoter, a ribosome sequence and/or a polyadenylation (pA) signal sequence. For example, the promoter may comprise a mammalian promoter. The promoter can be at the 5' end of the cDNA clone, and is optionally a simian virus 40 (SV40) or a cytomegalovirus (CMV) promoter. The ribozyme sequence can be at the 3' end of the cDNA clone, and is optionally a hepatitis delta virus ribozyme (HDVr) sequence. The pA signal sequence can be at the 3' end of the ribosome sequence, and is optionally a SV40 pA signal element. In some embodiments, the plasmid is an expression vector, optionally a mammalian expression vector.

The DNA-launched live-attenuated vaccines of the invention may be further modified, engineered, optimized, or appended in order to provide or select for further attenuation, immunogenicity, increased yield and/or other various features. In particular, the DNA copies of live attenuated ZIKV, YFV or JEV strains or other plus-sense single stranded RNA virus strains of the invention may comprise mutations to the viral genome. A mutation can be, but is not limited to, a deletion of non-coding or coding nucleotides, a deletion of one or more amino acids, an addition of one or more amino acids, a substitution (conserved or non-conserved) of one or more amino acids or a combination thereof. The DNA copy of the virus can be mutated, e.g., using deletions to the 3'UTR, such that the infectivity and/or pathogenicity, of the virus is reduced. In certain embodiments, the infectivity of the virus, e.g., ZIKV, is reduced by a factor of at least 5, 10, 50, 100, 500, 10, $5 \times 10^3$, $10^4$, $5 \times 10^4$, $10^5$, $5 \times 10^5$, or at least $10^6$.

Additionally, the DNA copy of the virus genome can be mutated, e.g., having deletions to the 3'UTR and/or using point mutations, such that the rate of replication of the resulting recombinant virus is reduced or increased. The rate of replication can be determined by any standard technique known to the skilled artisan. The rate of replication is represented by the growth rate of the virus and can be determined by plotting the viral titer over the time post infection. The viral titer can be measured by any technique known to the skilled artisan. In certain embodiments, a suspension containing the virus is incubated with cells that are susceptible to infection by the virus including, but not limited to, Vero cells, LLC-MK-2 cells, Hep-2 cells, LF 1043 (HEL) cells, MRC-5 cells, WI-38 cells, tMK cells, 293 T cells, QT 6 cells, QT 35 cells, or chicken embryo fibroblasts (CEF). Subsequent to the incubation of the virus with the cells, the number of infected cells is determined. In certain specific embodiments, the virus comprises a reporter gene. Thus, the number of cells expressing the reporter gene is representative of the number of infected cells. In a specific embodiment, the virus comprises a heterologous nucleotide sequence encoding mCherry, and the number of cells expressing mCherry, i.e., the number of cells infected with the virus, is determined using FACS.

The assays described herein may be used to assay viral titre over time to determine the growth characteristics of the virus. In a specific embodiment, the viral titre is determined by obtaining a sample from the infected cells or the infected subject, preparing a serial dilution of the sample and infecting a monolayer of cells that are susceptible to infection with the virus at a dilution of the virus that allows for the emergence of single plaques. The plaques can then be counted and the viral titre express as plaque forming units per milliliter of sample. In a specific embodiment of the invention, the growth rate of a virus of the invention in a subject is estimated by the titer of antibodies against the virus in the subject. Without being bound by theory, the antibody titer in the subject reflects not only the viral titer in the subject but also the antigenicity. If the antigenicity of the virus is constant, the increase of the antibody titer in the subject can be used to determine the growth curve of the virus in the subject. In a preferred embodiment, the growth rate of the virus in animals or humans is best tested by sampling biological fluids of a host at multiple time points post-infection and measuring viral titer.

The expression of heterologous gene sequence in a cell culture system or in a subject can be determined by any technique known to the skilled artisan. In certain embodiments, the expression of the heterologous gene is measured by quantifying the level of the transcript. The level of the transcript can be measured by Northern blot analysis or by RT-PCR using probes or primers, respectively that are specific for the transcript. The transcript can be distinguished from the genome of the virus because the virus is in the antisense orientation whereas the transcript is in the sense orientation. In certain embodiments, the expression of the heterologous gene is measured by quantifying the level of the protein product of the heterologous gene. The level of the protein can be measured by Western blot analysis using antibodies that are specific to the protein.

The DNA copy of the live attenuated plus-sense single stranded RNA virus of the present invention, vectors encoding the same, and cells comprising the same may be further modified, engineered, optimized, or appended in order to provide or select for various features in addition to attenuation. In particular the attenuated virus may also contain other mutations including, but not limited to, replacing a gene of the human virus with the analogous gene of a virus of a different species, of a different subgroup, or of a different variant.

In some embodiments, one or more missense mutations, additions, substitutions, or deletions can be introduced into the C, prM, E, NS1, NS2A, NS2B, NS3, NS4A, NS4B, or NS5 proteins of the recombinant virus. For example, a deletion mutation in any of the C, prM, E, NS1, NS2A, NS2B, NS3, NS4A, NS4B, or NS5 proteins may be introduced. In other embodiments, a missense mutation may be introduced which results in a cold-sensitive mutation or a heat-sensitive mutation. In some embodiments, major phosphorylation sites of viral protein may be removed. In other embodiments, deletions are introduced into the DNA copy of the genome of the recombinant virus. In more specific embodiments, a deletion can be introduced into the C, prM, E, NS1, NS2A, NS2B, NS3, NS4A, NS4B, or NS5 proteins of the recombinant virus.

In certain embodiments, the intergenic region of the DNA copy of the recombinant virus is altered. In one embodiment, the length of the intergenic region is altered. In another embodiment, the intergenic regions may be shuffled from the 5' to 3' end of the viral genome. In other embodiments, the genome position of a gene or genes of the recombinant virus can be changed.

In certain embodiments, attenuation of the virus is further enhanced by replacing a gene of the wild type virus with a gene of a virus of a different species, of a different subgroup, or of a different variant.

The attenuated phenotypes of a recombinant virus transcribed from the vaccine of the invention can be tested by any method known to the artisan. A candidate virus can, for example, be tested for its ability to infect a host or for the rate of replication in a cell culture system. In certain embodiments, growth curves at different temperatures are used to test the attenuated phenotype of the virus. For example, an attenuated virus can grow at 35° C., but not at 39° C. or 40° C. In certain embodiments, different cell lines can be used to evaluate the attenuated phenotype of the virus. For example, an attenuated virus may only be able to grow in monkey cell lines but not the human cell lines, or the achievable virus titers in different cell lines are different for the attenuated virus. In certain embodiments, viral replication in the respiratory tract of a small animal model, including but not limited to, hamsters, cotton rats, mice and guinea pigs, is used to evaluate the attenuated phenotypes of the virus. In other embodiments, the immune response induced by the virus, including but not limited to, the antibody titers (e.g., assayed by plaque reduction neutralization assay or ELISA) is used to evaluate the attenuated phenotypes of the virus. In certain embodiments, the ability of the recombinant virus to elicit pathological symptoms in an animal model can be tested. A reduced ability of the virus to elicit pathological symptoms in an animal model system is indicative of its attenuated phenotype. In a specific embodiment, the candidate viruses are tested in a monkey model for nasal infection, indicated by mucous production.

Various assays can be used to test the safety of a vaccine. For example, sucrose gradients and neutralization assays can be used to test the safety. A sucrose gradient assay can be used to determine whether a heterologous protein is inserted in a virion. If the heterologous protein is inserted in the virion, the virion should be tested for its ability to cause symptoms even if the parental strain does not cause symptoms. Without being bound by theory, if the heterologous protein is incorporated in the virion, the virus may have acquired new, possibly pathological, properties.

Vaccines produced according to the invention will be used to confer prophylactic or therapeutic protection in susceptible hosts against viral infection, e.g. to treat or prevent ZIKV, YFV or JEV infection and/or to prevent congenital ZIKV syndrome or GBS or to prevent yellow fever infection or Japanese encephalitis viral infection. The vaccines of the invention may be formulated using known techniques for formulating DNA vaccines or immunogenic compositions of DNA vaccines.

Administration

The vaccines of the present invention can be administered to a recipient by any available technique. For example, the vaccines may be introduced by needle injection, preferably intradermally, subcutaneously or intramuscularly. Alternatively, the vaccines may be delivered directly across the skin using a nucleic acid delivery device such as particle-mediated DNA delivery (PMDD).

Suitable techniques for introducing DNA vaccines into a recipient include topical application with an appropriate vehicle. The vaccines may be administered topically to the skin, or to mucosal surfaces for example by intranasal, oral, intravaginal or intrarectal administration. The vaccine may be present together with a pharmaceutically acceptable excipient, such as phosphate buffered saline (PBS). DNA uptake may be further facilitated by addition of facilitating agents such as bupivacaine to the composition. Other methods of administering DNA directly to a recipient include ultrasound, electrical stimulation, electroporation and microseeding.

Uptake of DNA vaccines may be enhanced by several known transfection techniques, for example those including the use of transfection agents such as cationic agents, for example, calcium phosphate and DEAE-Dextran and lipofectants, for example, lipofectam and transfectam.

The vaccines of the invention are typically formulated in a pharmaceutical composition suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The terms "oral", "enteral", "enterally", "orally", "non-parenteral", "non-parenterally", and the like, refer to administration of a compound or composition to an individual by a route or mode along the alimentary canal. Examples of "oral" routes of administration of a vaccine composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories for the lower intestinal tract of the alimentary canal.

Preferably, the formulated vaccine-containing composition is suitable for intranasal, injection, topical or oral administration, for example as a dried stabilized powder for reconstitution in a suitable buffer prior to administration or in an aerosol composition. In a preferred embodiment, the composition is injected or intranasally administered.

Pharmaceutical compositions and formulations for topical administration may include transdermal patches, ointments, lotions, creams, gels, drops, suppositories, sprays, liquids, semi-solids, monophasic compositions, multiphasic compositions (e.g., oil-in-water, water-in-oil), foams microsponges, liposomes, nanoemulsions, aerosol foams, polymers, fullerenes, and powders (see, e.g., Reference 35, Taglietti et al. (2008) Skin Ther. Lett. 13:6-8). Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal, or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, aerosols, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin, cationic glycerol derivatives, and polycationic molecules, such as polylysine, also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

The compositions of the present invention may include excipients known in the art. Examples of excipients used for vaccine formulation such as adjuvants, stabilizers, preservatives, and trace products derived from vaccine manufacturing processes include but are not limited to: Aluminum Hydroxide, Amino Acids, Benzethonium Chloride, Formaldehyde or Formalin, Inorganic Salts and Sugars, Vitamins, Asparagine, Citric Acid, Lactose, Glycerin, Iron Ammonium Citrate, Magnesium Sulfate, Potassium Phosphate, Aluminum Phosphate, Ammonium Sulfate, Casamino Acid, Dimethyl-betacyclodextrin, 2-Phenoxyethanol, Bovine Extract, Polysorbate 80, Aluminum Potassium Sulfate, Gelatin, Sodium Phosphate, Thimerosal, Sucrose, Bovine Protein, Lactalbumin Hydrolysate, Formaldehyde or Formalin, Monkey Kidney Tissue, Neomycin, Polymyxin B, Yeast Protein, Aluminum Hydroxyphosphate Sulfate, Dextrose, Mineral Salts, Sodium Borate, Soy Peptone, MRC-5 Cellular Protein, Neomycin Sulfate, Phosphate Buffers, Polysorbate, Bovine Albumin or Serum, DNA, Potassium Aluminum Sulfate, Amorphous Aluminum Hydroxyphosphate Sulfate, Carbohydrates, L-histidine, Beta-Propiolactone, Calcium Chloride, Neomycin, Ovalbumin, Potassium Chloride, Potassium Phosphate, Sodium Phosphate, Sodium Taurodeoxychoalate, Egg Protein, Gentamicin, Hydrocortisone, Octoxynol-10, .α-Tocopheryl Hydrogen Succinate, Sodium Deoxycholate, Sodium Phosphate, Beta-Propiolactone, Polyoxyethylene 910, Nonyl Phenol (Triton N-101, Octoxynol 9), Octoxinol-9 (Triton X-100), Chick Kidney Cells, Egg Protein, Gentamicin Sulfate, Monosodium Glutamate, Sucrose Phosphate Glutamate Buffer Calf Serum Protein, Streptomycin, Mouse Serum Protein, Chick Embryo Fibroblasts, Human Albumin, Sorbitol, Sodium Phosphate Dibasic, Sodium Bicarbonate, Sorbitol, Sucrose, Potassium Phosphate Monobasic, Potassium Chloride, Potassium Phosphate Dibasic, Phenol, Phenol Red (Phenolsulfonphthalein), Amphotericin B, Chicken Protein, Chlortetracycline, Ethylenediamine-Tetraacetic Acid Sodium (EDTA), Potassium Glutamate, Cell Culture Media, Sodium Citrate, Sodium Phosphate Monobasic Monohydrate, Sodium Hydroxide, Calcium Carbonate, D-glucose, Dextran, Ferric (III) Nitrate, L-cystine, L-tyrosine, Magnesium Sulfate, Sodium Hydrogenocarbonate, Sodium Pyruvate, Xanthan, Peptone, Disodium Phosphate, Monosodium Phosphate, Polydimethylsilozone, Hexadecyltrimethylammonium Bromide Ascorbic Acid, Casein, Galactose, Magnesium Stearate, Mannitol, Hydrolyzed Porcine Gelatin, Freund's emulsified oil adjuvants (complete and incomplete), Arlacel A, Mineral oil, Emulsified peanut oil adjuvant (adjuvant 65), Corynebacterium granulosum-derived P40 component, Lipopolysaccharide, Mycobacterium and its components, Cholera toxin, Liposomes, Immunostimulating complexes (ISCOMs), Squalene, and Sodium Chloride.

The vaccine or immunogenic composition may be used in the vaccination of a mammalian recipient or host, particularly a human, nonhuman primate, ape, monkey, horse, cow, carabao, goat, duck, bat, or other suitable non-human host. In some instances, the subject may be immunocompromised or may have another condition, e.g., may be pregnant.

The following examples are offered to illustrate, but not to limit, the claimed invention.

Example 1

Background: Vaccines are the most effective means to fight and eradicate infectious diseases. Live-attenuated vaccines (LAV) usually have the advantages of single dose, rapid onset of immunity, and durable protection. DNA vaccines have the advantages of chemical stability, ease of production, and no cold chain requirement. The ability to combine the strengths of LAV and DNA vaccines may transform future vaccine development by eliminating cold chain and cell culture with the potential for adventitious agents.

As is described in detail below a DNA-launched LAV was developed for Zika virus (ZIKV), a pathogen that recently caused a global public health emergency. A cDNA copy of a ZIKV LAV genome was engineered into a DNA plasmid. The DNA-LAV plasmid was delivered into mice using a clinically proven device TriGrid™ to launch the replication of LAV.

As further described in detail below it was demonstrated that a single-dose immunization comprising as low as 0.5 µg of said DNA-LAV plasmid conferred 100% seroconversion in A129 mice. All seroconverted mice developed sterilizing immunity, as indicated by no detectable infectious viruses and no increase of neutralizing antibody titers after ZIKV challenge. The immunization also elicited robust T cell responses. In pregnant mice, the DNA-LAV vaccination fully protected against ZIKV-induced disease and maternal-to-fetal transmission. High levels of neutralizing activities were detected in fetal serum, indicating maternal-to-fetal humoral transfer. In male mice, a single-dose vaccination completely prevented testis infection, injury, and oligospermia.

In particular using Zika virus (ZIKV) as a model, we developed a DNA-launched live-attenuated vaccine (LAV) that combines the advantages of DNA vaccines (chemical stability, no cold chain, easy production, and low cost) and LAVs (single dose, quick immunity and durable protection). Remarkably, a single-dose vaccination as low as 0.5 µg of the DNA-LAV plasmid elicited 100% protective immunity within 14-21 days in A129 mice. The vaccination completely prevented ZIKV infection, in utero transmission during pregnancy, and male reproductive tract infections. Besides antibody response, the immunized mice also developed robust T cell responses. Compared with previous DNA-launched LAV studies, this study showed the lowest minimal plasmid dose (0.5 µg) required for 100% protection and, for the first time, that a DNA-launched LAV can elicit sterilizing immunity as well as robust T cell responses. The DNA-launched approach could serve as a universal platform to deliver LAVs for other positive-sense, single-stranded RNA viruses.

These findings, and in particular the remarkable potency of this exemplary ZIKV DNA-LAV plasmid immunogen, suggest that such ZIKV DNA-LAV plasmid may be used to produce immunogenic compositions or vaccines which confer protective immunity against ZIKA. Moreover, these findings further suggest that the DNA-LAV approach may serve as a universal vaccine platform for other plus-sense RNA viruses, e.g., other flaviviruses. This is highly significant as enhancing vaccine performance with improved simplicity and immunity is critical, particularly when responding to epidemic emergencies. The ability to combine the advantages of different vaccine platforms could transform future vaccine development.

Materials and Methods

Cells and Antibodies. The African green monkey kidney epithelial (Vero) cell and human embryonic kidney cell (293T) were purchased from the American Type Culture Collection (ATCC, Bethesda, MD) and maintained in a high-glucose Dulbecco's modified Eagle's medium (DMEM) supplemented with 10% fetal bovine serum (FBS) (HyClone Laboratories, South Logan, UT) and 1% penicillin/streptomycin (P/S). Cells were cultured at 37° C. with 5% $CO_2$. Culture medium and antibiotics were purchased from ThermoFisher Scientific (Waltham, MA).

The following antibodies were used in this study: a mouse monoclonal antibody (mAb) 4G2 cross-reactive with flavivirus E protein (ATCC), a mouse polyclone antibody against ZIKV NS5 (in-house generated using the recombinant ZIKV NS5 protein purified from E. coli.), ZIKV-specific HMAF (hyper-immune ascitic fluid; obtained from the World Reference Center of Emerging Viruses and Arboviruses [WRCEVA] at the University of Texas Medical Branch), goat anti-mouse IgG conjugated with horseradish peroxidase (HRP; KPL, Gaithersburg, MD), and goat anti-mouse IgG conjugated with Alexa Fluor 568 (ThermoFisher Scientific).

Plasmid Construction. The plasmid pFLZIKV-PRV (derived from a single-copy vector pCC1™ [Epicentre, Madison, WI]) [28] was used as a starting vector to construct the DNA-launched plasmids in this study. Firstly, the cDNA sequence of ZIKV strain Cambodian FSS13025 (GenBank accession No. KU955593) and the hepatitis delta virus ribozyme (HDVr) was digested from an infectious clone pFLZIKV [29], and cloned into the pFLZIKV-PRV using restriction enzymes NotI and ClaI, resulting in the plasmid pCC1-T7-ZIKV. Next, the simian virus 40 (SV40) or cytomegalovirus (CMV) promoter sequences were amplified by standard PCR from the pcDNA3.1(+) (ThermoFisher Scientific) and fused with the 5'UTR sequence of ZIKV, respectively. The resulting DNA fragments were cloned into the pCC1-T7-ZIKV plasmid using restriction enzymes HpaI and NheI, resulting in subclones pCC1-SV40-ZIKVa and pCC1-CMV-ZIKVa. Lastly, the SV40 or bovine growth hormone (BGH) polyadenylation (pA) signal sequences were amplified from the pcDNA3.1 vector and cloned into the pCC1-SV40-ZIKVa and pCC1-CMV-ZIKVa through restriction enzymes ClaI and SrfI, respectively, resulting in plasmids pSV40-ZIKV (short as WT or SV40-WT) and pCMV-ZIKV (short as CMV-WT). The flavivirus-conserved polymerase motif GDD mutation (corresponding to residues Gly664, Asp665, and Asp666 in ZIKV NS5 were mutated to Ala) [30] and the 3'UTR 20 nucleotide deletion ($\Delta 20$) [22] was introduced by overlap PCR and cloned into the plasmid pCC1-SV40-ZIKV through restriction enzymes EcoRI and ClaI, resulting in plasmids pFLZIKV-$\Delta$GDD (short as $\Delta$GDD) and pFLZIKV-3'UTR-$\Delta 20$ (short as $\Delta 20$). Plasmids were propagated in the TransforMax EPI300 Chemically Competent *E. coli* (Epicentre, Madison, WI). This pCC1™ vector-derived plasmid could be induced to generate 10-20 copies/cell using L-arabinose in the *E. coli* strain EPI300. All restriction enzymes were purchased from New England BioLabs (Ipswitch, MA). All plasmids were validated through restriction enzyme digestion and Sanger DNA sequencing. All primers were synthesized from Integrated DNA Technologies (Skokie, Illinois) and available upon request.

DNA transfection. $5\times10^5$ Vero cells or $7\times10^5$ 293T cells per well were seeded into a 6-well plate. The next day, cells were transfected with 4 µg plasmids by X-tremeGENE 9 DNA transfection reagent (Roche) in 3 ml 2% FBS DMEM medium. From day 1 to 5 post-transfection, 200 µl of culture fluids were collected daily, centrifuged at 415×g for 5 min to remove cell debris and stored at −80° C. Viral titers were determined by plaque assay.

Plaque assay. $1.5\times10^5$ Vero cells per well were seeded into a 24-well plate. The next day, 100 µl of undiluted virus sample or series of 10-fold diluted virus samples were added to individual well of cell monolayer. After 1 h of incubation at 37° C. with 5% $CO_2$, the inoculum in each well was replaced with 0.6 ml of overlay medium (DMEM medium supplemented with 2% FBS and 0.8% methylcellulose [Sigma]). After incubation at 37° C. with 5% $CO_2$ for 4 days, cells were fixed in 3.7% formalin solution and stained with 1% crystal violet. For ZIKV $\Delta 20$ mutant viruses, viral titers were determined by focus-forming assay as described previously [22].

Immunofluorescence assay (IFA). $8\times10^4$ Vero Cells were seeded into each well of an 8-well Lab-Tek II chamber slide (Thermo Fisher Scientific). The next day, cells were transfected with 0.5 µg of DNA per well. At selected time points, cells were fixed with chilled methanol at −20° C. for 30 min. After 1 h incubation in blocking buffer (PBS supplemented with 1% FBS and 0.05% Tween-20), cells were incubated with the primary antibody 4G2 for 1 h. After three PBS washes, cells were incubated with goat anti-mouse IgG conjugated with Alexa Fluor 568 (1:1000 diluted in blocking buffer) for 1 h. Finally, after three PBS washes, cells were mounted in a Vectashield mounting medium with DAPI (Vector Laboratories). Fluorescence images were acquired under Eclipse Ti2 inverted fluorescence microscope (Nikon Instruments Inc.).

SDS-PAGE and Western Blot. Cells from the 6-well plates were washed once with PBS and lysed at 4° C. for 1 h in 200 µl RIPA lysis buffer (ThermoFisher Scientific) supplemented with 1× complete protease inhibitor cocktail (Roche). Lysates were centrifuged at 20,000×g and 4° C. for 30 min to remove cell debris. Supernatants were collected and mixed with 4×LDS sample buffer (ThermoFisher Scientific). After denaturing at 70° C. for 15 min, 10 µl samples were loaded onto to a 12% Mini-Protean TGX Stain-Free Precast gel (Bio-Rad Laboratories). After separation by electrophoresis, proteins were transferred onto a polyvinylidene difluoride (PVDF) membrane using a Trans-Blot Turbo Transfer System (Bio-Rad Laboratories). The blot was firstly incubated at room temperature for 1 h in a blocking buffer containing TBST (10 mM Tris-HCl [pH 8.0], 150 mM NaCl, and 0.1% Tween 20) and 5% skim milk, followed by 1 h of incubation with primary antibody (1:1, 000 dilution in blocking buffer). After three TBST-buffer washes, the blot was incubated with the goat anti-mouse IgG conjugated to HRP (1:10,000 dilution in blocking buffer). After another three TBST-buffer washes, the blot was incubated with SuperSignal™ West Femto Maximum Sensitivity Substrate (Thermo Fisher Scientific). Chemiluminescence signals were detected in ChemiDoc System (Bio-Rad).

RT-PCR and Sequencing. Viral RNAs in culture fluids (140 µl) or mouse serum were used for viral RNA extraction by QIAamp viral RNA mini kit (Qiagen). RT-PCR assays were performed using SuperScript III One-Step RT-PCR System with Platinum Taq DNA Polymerase kit (Life technologies) following the manufacturer's protocols. Six cDNA fragments covering the entire genome of ZIKV were amplified by RT-PCR, purified and subjected to Sanger sequencing at GENEWIZ (South Plainfield, NJ).

ZIKV/mCherry Neutralization Assay. Titers of neutralizing antibody in mouse serum were determined by using a ZIKV/mCherry infection assay as described previously [22, 23]. Briefly, sera were 2-fold serially diluted (starting at 1:25 dilution) in culture medium (containing 2% FBS) and then incubated with equal volume of ZIKV/mCherry reporter viruses at 37° C. for 1 h. Afterwards, antibody-virus complexes were added to Vero cell monolayers in a 96-well plate. At 48 h post-infection, mCherry fluorescence-positive cells were quantified by Cytation 5 Cell Imaging Multi-Mode Reader (Biotek). Fluorescence-positive cells from serum-treated wells were normalized to those of non-treatment controls (set as 100%). The effective dilution of sera to reduce the percentage of mCherry-positive cells by 50% ($NT_{50}$) was calculated using nonlinear regression analysis in GraphPad Prism 7 software (La Jolla, CA).

Mouse Experiment. All animal studies were performed as approved by the University of Texas Medical Branch (UTMB) Institutional Animal Care and Use Committee (IACUC). All efforts were made to minimize animal suffering. Plasmid DNA was diluted to indicated concentration in calcium/magnesium-free phosphate-buffered saline (DPBS, ThermoFisher Scientific) and administrated into A129 mice by intramuscular (IM) injection or by IM injection together with electroporation (IM&EP) using the TriGrid™ Delivery System (Ichor Medical Systems, San Diego, CA) as described previously [31]. The A129 mouse is a model susceptible to ZIKV infection [32]. For consistent dosing by TriGrid™ device, six-week-old mice A129 mice with weight above 15 g were chosen for this study. Briefly, after anesthetized with isoflurane gas, mice were injected into one tibialis anterior muscle with 20 μl of DNA solution using a 3/10 ml U-100 insulin syringe (Becton-Dickinson, Franklin Lakes, NJ) inserted into the center of a TriGrid electrode array with 2.5 mm electrode spacing. Mock-infected mice were given DPBS by the same route. Injection of DNA was followed immediately by electrical stimulation at an amplitude of 250 V/cm, and the total duration was 40 ms over a 400-ms interval. The control intramuscular injection was performed as described above without the application of electrical stimulation.

After immunization, mice were monitored for weight loss and signs of disease daily. At selected time points, mice were bled via the retro-orbital sinus (RO) and viremia was determined by plaque assay. Neutralizing antibodies in sera were measured using ZIKV/mCherry infection assay. Mice were challenged on day 29 post-immunization with parental ZIKV strain PRVABC59 ($10^6$ PFU) via the subcutaneous route. On day 2 post challenge, mice were bled and viremia was determined by plaque assay. Sperm counting was performed according to the protocol as described previously [23]. Mice were euthanized and necropsied at indicated time points. Epididymis and testes were harvested immediately. Motile and non-motile sperms were counted manually on a hemocytometer by microscopy. Total sperm counts equal to the sum of motile and non-motile sperms.

For the mouse pregnancy study, the same IM&EP procedures were applied to administer the DNA solution into six-week old female mice. On day 29 post-immunization, mice were bled for measuring $NT_{50}$. Mice were mated starting on day 30 post-immunization. Mouse embryonic development started (E0.5) once mouse vaginal plugs were observed. At E10.5, mice were challenged with parental ZIKV strain PRVABC59 ($10^6$ PFU) via the subcutaneous route. At E12.5, mice were bled to measure viremia. At E18.5, all dams were euthanized and maternal tissues (brain, spleen and placenta) and fetuses were harvested. Fetal weight was measured immediately. After decapitation, fetal heads and blood were collected. Mouse tissues were homogenized in 500 μl of DMEM medium using TissueLyser II (Qiagen) for 5 min at 30 Hz. After centrifugation at 15,000× rpm for 10 min, supernatants were harvested. Plaque assays were performed on Vero cells to determine virus loads in maternal brain, spleen and placenta, and fetal head. Neutralizing antibodies in fetal serum were measured using ZIKV/mCherry neutralization assay as described above.

Intracellular cytokine staining (ICS). Approximately 2.5×$10^6$ splenocytes were stimulated with 1×$10^6$ IFU of live ZIKV (strain FSS13025) for 24 h or 10 μg/ml E peptide (Sequence 294-302 in ZIKV polyprotein) [33] for 5 h. Live ZIKV was used as a stimulant for measuring both $CD4^+$ and $CD8^+$ T cell response [34]. The E peptide was used as stimulant for measuring $CD8^+$ T cell response [33]. During the final 5 h of stimulation, BD GolgiPlug (BD Bioscience) was added to block protein transport. Cells were stained with antibodies against surface markers CD3 (APC-conjugated) and CD4 (FITC-conjugated) or CD8 (FITC-conjugated). Afterwards, cells were fixed in 2% paraformaldehyde and permeabilized with 0.5% saponin. Cells were then incubated with PE-conjugated anti-IFN-γ and PE-Cy7-conjugated anti-TNF-α antibodies or control PE-conjugated rat IgG1. Samples were processed with a BD Accuri™ C6 Flow Cytometer instrument. Dead cells were excluded on the basis of forward and side light scatter. Data were analyzed with a CFlow Plus Flow Cytometer (BD Biosciences).

Bio-Plex immunoassay. Approximately 3×$10^5$ splenocytes per well were plated in a 96-well plate and stimulated with 2×$10^4$ FFU of ZIKV (strain FSS13025) for 2 days, respectively. Culture supernatants were harvested and frozen at −80° C. Cytokines IL-2, IFN-Υ and TNF-α in the culture supernatants were measured using a Bio-Plex Pro Mouse Cytokine Assay (Bio-Rad, Hercules, CA) according to the manufacturer's instructions.

Data process and analysis. Images were processed in software ImageJ (NIH). Data were analyzed in GraphPad Prism 7.0 software (La Jolla, CA). Results were presented as the mean±standard deviation unless indicated separately. Comparisons of groups were performed using multiple t-test, unpaired nonparametric Mann-Whitney unpaired test or one-way ANOVA test. *$p<0.05$, significant; $p<0.01$, very significant; *$p<0.001$, highly significant; ****$p<0.0001$, extremely significant; n.s., not significant. Figures were assembled using Adobe illustrator.

Results

Construction and characterization of plasmid DNA-LAV in cell culture. We converted ZIKV-3'UTR-Δ20 (a LAV candidate containing a 20-nucleotide deletion within the 3'UTR of the ZIKV genome) into a plasmid DNA-launched LAV. ZIKV-3'UTR-Δ20 has an excellent safety and efficacy profile: a single-dose vaccination of $10^3$ FFU confers sterilizing immunity in NHPs [23]. To convert it to a plasmid-launched LAV, we selected the pCC1™ vector to clone the cDNA of ZIKV-3'UTR-Δ20 because its copy number can be conditionally controlled in E. coli: (i) A single copy per cell to maximize the plasmid stability during cloning and (ii) 10-20 copies per cell to maximize plasmid yield during production [35].

A eukaryotic promoter was engineered at the 5' end of ZIKV-3'UTR-Δ20 cDNA to launch the transcription of viral RNA through cellular RNA polymerase II (FIG. 1A). A hepatitis delta virus ribozyme (HDVr) sequence and a polyA-signal sequence were engineered at the 3' end of ZIKV-3'UTR-Δ20 cDNA for generation of the authentic 3' end of the viral RNA and for transcription termination (FIG. 1A). The resulting plasmid is named as pZIKV-3'UTR-Δ20. As controls, we also cloned the cDNA of wild-type (WT) ZIKV and a viral polymerase-defective mutant (containing an active site GDD-*AAA mutation, defined as ΔGDD) into the pCC1™ plasmid, resulting in pZIKV-WT and pZIKV-ΔGDD, respectively.

Figure 7:
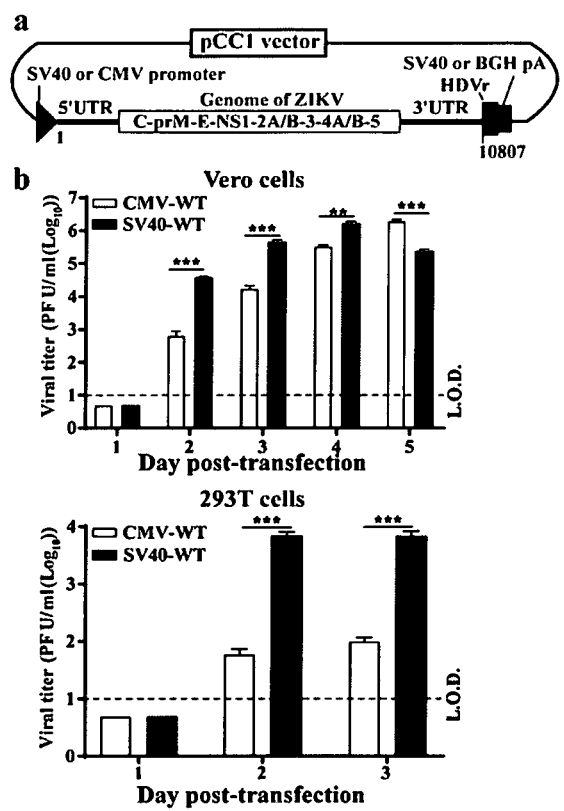
FIG. 7A-B shows a comparison of SV40 and CMV promoters in pZIKV-WT to launch WT ZIKV replication in cell culture. (A) Diagram of pZIKV-WT plasmid. Plasmid pCC1™ vector was used to engineer a gene cassette containing a promoter from simian virus 40 (SV40) or from cytomegalovirus (CMV), WT ZIKV cDNA, hepatitis delta virus ribozyme (HDVr) sequence, and SV40 polyadenylation (pA) signal element. (B) Virus replication post-transfection. Plasmids pZIKV-WT containing SV40 promoter or CMV promoter (4 µg) were transfected into Vero (Top panel) or 293T (bottom panel) cells. Culture supernatants were collected daily and viral titers were determined by plaque assay. It should be noted that ZIKV FSS13025 strain does not replicate efficiently in 293T cells. The limited of detection (L.O.D.) of plaque assay is 10 PFU/ml, as indicated by the dotted line. Multiple t-test was performed to analyze the statistical significances.

We initially determined which eukaryotic promoter would potentially launch the LAV viral replication in cells. Using pZIKV-WT, we compared the efficiencies of two commonly used eukaryotic promoters (SV40 and CMV) to launch ZIKV (FIG. 7A). After transfecting pZIKV-WT DNA into Vero and 293T cells, we observed that the SV40 promoter launched ZIKV more rapidly than the CMV promoter in both cell lines from days 2 to 3 (FIG. 7B). This result prompted us to engineer the SV40 promoter to pZIKV-3'UTR-Δ20 (FIG. 1A). Once the SV40-driven pZIKV-3'UTR-Δ20 was constructed, we characterized its ability to launch replication of the LAV virus in cell culture. Upon transfection into Vero cells, pZIKV-3'UTR-Δ20 generated viral E protein-positive cells (FIG. 1B), viral NS5 protein (FIG. 1C), and high titers of LAV virus (peak viral titer of 2×$10^6$ PFU/ml; FIG. 1D). Compared with pZIKV-WT, pZIKV-3'UTR-Δ20 produced fewer E-positive cells (FIG. 1B) and less NS5 protein (FIG. 1C) in transfected cells. The recovered ZIKV-3'UTR-Δ20 virus exhibited smaller focus morphology than the WT ZIKV (FIG. 1E). As a negative control, cells transfected with the replication-defective pZIKV-ΔGDD did not generate any detectable viral proteins or virus (FIG. 1B-E). These results demonstrate that pZIKV-3'UTR-Δ20 DNA is able to efficiently launch LAV virus in cell culture.

Figure 2:
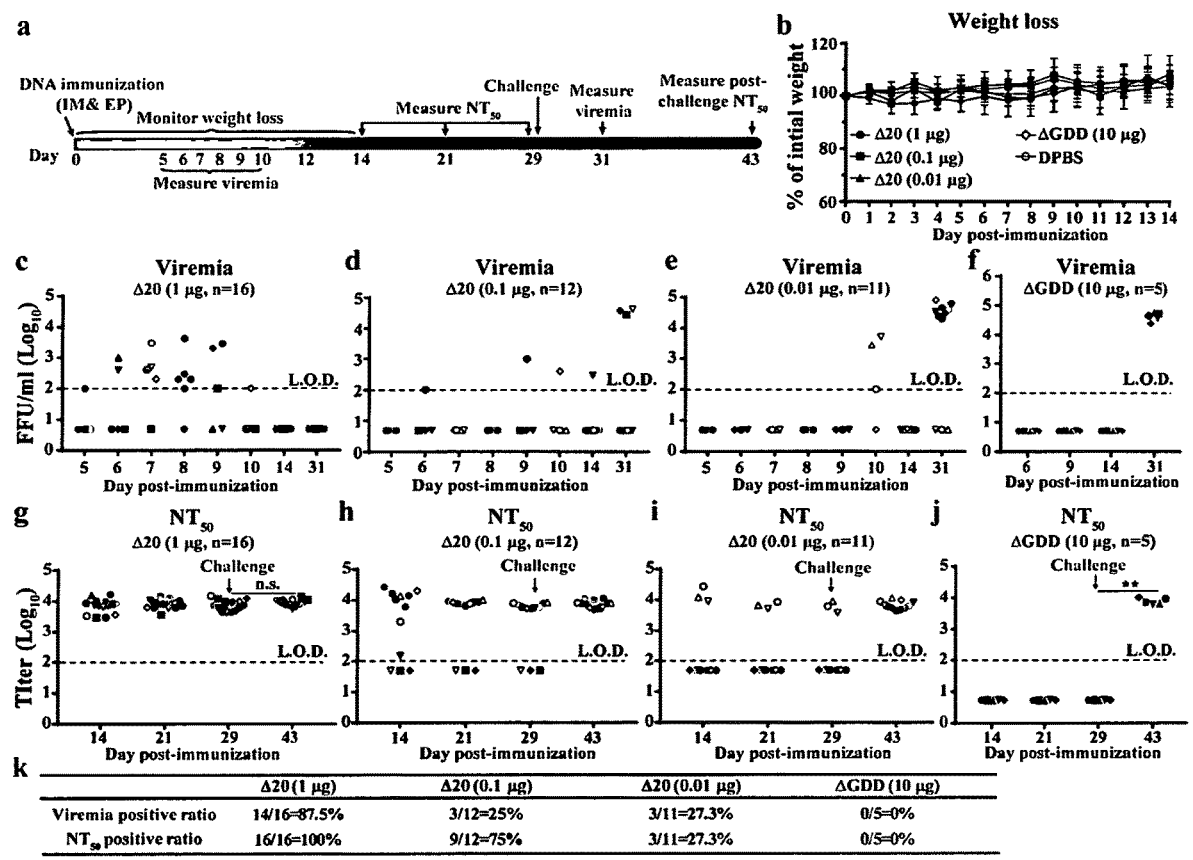
FIG. 2A-K shows that immunization of pZIKV-3'UTR-Δ20 protects the A129 mouse from ZIKV challenge. (A) Experimental design. Various doses of pZIKV-3'UTR-Δ20 (1, 0.1, 0.01 μg), pZIKV-ΔGDD (10 μg), or DPBS (sham) were inoculated to six-week-old A129 mice via intramuscular (IM) injection and electroporation (EP) using TriGrid™. Following immunization, mice were monitored for weight loss over 14 days. Since our IACUC protocol only allows four blood draws per mouse over 28 days post-transfection (or infection), blood draws were staggered for different mouse sub-cohorts to cover the sampling period of days 5-10 post-immunization. Mice were bled at indicated time for measuring neutralizing antibody titers ($NT_{50}$) using a mCherry-ZIKV neutralization assay. On day 29 post-immunization, the mice were challenged with $10^6$ PFU of ZIKV strain PRVABC59 via the subcutaneous route (indicated by a red arrow). At indicated time, the mice were bled for measuring viremia using a focus-forming assay. (B) Mouse weight post-immunization. (C-F) Viremia for the mouse groups immunized with 1 μg pZIKV-3'UTR-Δ20 (c), 0.1 μg pZIKV-3'UTR-Δ20 (D), 0.01 μg pZIKV-3'UTR-Δ20 (E), or 10 μg pZIKV-AGDD (F). (G-J) Neutralizing antibody titers ($NT_{50}$) from the mouse groups immunized with 1 μg pZIKV-3'UTR-Δ20 (G), 0.1 μg pZIKV-3'UTR-Δ20 (H), 0.01 μg pZIKV-3'UTR-Δ20 (I), or 10 μg pZIKV-ΔGDD (J). Group sizes (n number) are indicated. Individual mice are indicated by different colors and symbols. Paired t-test was performed to indicate no significant difference (n.s.) between the pre-challenge (day 29) and post-challenge (day 43) neutralizing antibody titers in (G). (K) Summary of viremia-positive and neutralizing antibody-positive ratios for all mouse groups. Limits of detections (L.O.D., dotted lines) of focus-forming assay and neutralization assay ($NT_{50}$) were 100 FFU/ml and 100 dilution, respectively.

Immunogenicity and efficacy in A129 mice. We next evaluated the immunogenicity and efficacy of the pZIKV-3'UTR-Δ20 DNA in A129 mice [32], which are deficient in interferon-α/β receptors. We chose the TriGrid™ to deliver the plasmid to mice because (i) this device combines intramuscular injection with electroporation and (ii) it has already been successfully used in clinical trials [36]. FIG. 2A outlines the experimental design. A single dose of 0.01, 0.1, or 1 μg of pZIKV-3'UTR-Δ20 DNA- was administered to the tibialis anterior muscle of six-week-old A129 mice. As controls, mice were administered replication-defective pZIKV-ΔGDD (10 μg), which was expected to yield translation of transcribed ZIKV RNA but not subsequent viral replication, or DPBS. After immunization, all mice remained healthy with no detectable pathologic changes at the site of injection or adverse effects including no weight loss (FIG. 2B). Viremia of <$10^4$ PFU/ml was detected in each of the three pZIKV-3'UTR-Δ20-dosed groups (FIG. 2C-F), although the 1-μg dosed group exhibited a higher viremia-positive rate (88%) than the 0.1-μg (25%) and 0.01-μg (27%) groups (FIG. 1K). Sequencing of the viral RNA from mouse sera collected during viremia showed the engineered 20-nucleotide deletion at the 3'UTR without other mutations. Seroconversion rates of 100%, 75%, and 27% were observed from the 1-μg, 0.1-μg, and 0.01-μg pZIKV-3'UTR-Δ20 groups, respectively (FIG. 1K). For each seroconverted mouse, pZIKV-3'UTR-Δ20 DNA rapidly elicited high neutralizing antibody titers of almost $10^4$ within 14-21 days post-immunization (FIG. 2G-I). Upon challenge with $10^6$ PFU of a WT ZIKV strain PRVABC59 from the Puerto Rico epidemic, on day 29 post-immunization, all seroconverted mice were fully protected against infection (FIG. 2C-E), whereas the seronegative mice generated viremia on day 2 post-challenge. Notably, the challenge did not boost the neutralizing antibody titers of seroconverted mice, as indicated by no statistical difference between the neutralizing antibody titers on days 29 and 43 (FIG. 2G-I). As a negative control, immunization with 10 μg of pZIKV-ΔGDD DNA conferred no viremia post-immunization (FIG. 2F), no neutralizing antibodies before challenge (FIG. 2J), and no protection against challenge (FIG. 2F). Taken together, the results indicate that a single dose of pZIKV-3'UTR-Δ20 is able to rapidly elicit sterilizing immunity (defined as no detectable infectious viruses and no increase of neutralizing antibody titers after challenge) that confers complete protection against ZIKV infection.

Figure 8:
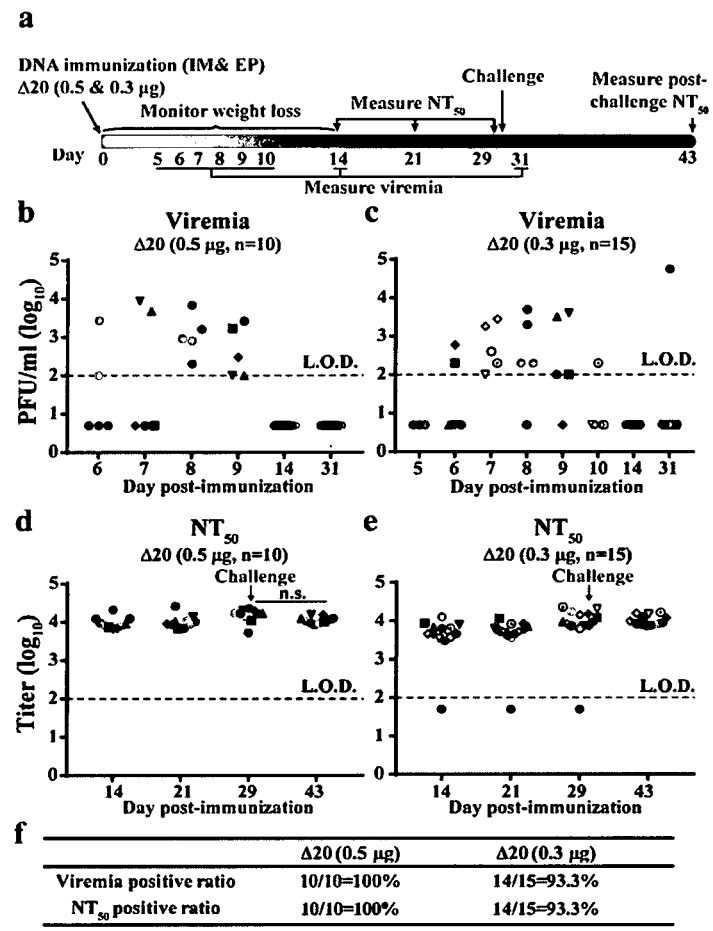
FIG. 8A-F shows the minimal dose of pZIKV-3'UTR-A20 required for seroconversion and protection. (A) Experimental design. Six-week-old A129 mice were immunized with 0.5 or 0.3 µg of pZIKV-3'UTR-Δ20 using TriGrid™. At the indicated time points, the mice were bled for measuring viremia and neutralizing antibody titers. (B) Viremia from the 0.5 µg pZIKV-3'UTR-Δ20 group. (C) Viremia from the 0.3 µg pZIKV-3'UTR-Δ20 group. (D) Neutralizing antibody titers from the 0.5 µg pZIKV-3'UTR-Δ20 group. Paired t-test was performed to indicate no significant difference (n.s.) between the pre-challenge (day 29) and post-challenge (day 43) neutralizing antibody titers. (E) Neutralizing antibody titers from the 0.3 µg pZIKV-3'UTR-Δ20 group. Individual mice are indicated by different colors and symbols. (F) Summary of viremia positive and seropositive ratios.

Minimal dose for 100% seroconversion and protective immunity. To determine the minimal dose required for 100% seroconversion, we immunized A129 mice with 0.3 or 0.5 μg of pZIKV-3'UTR-Δ20 (FIG. 8A). All 10 mice from the 0.5-μg group and 14 out of 15 mice from the 0.3-μg group developed viremia during days 6-10 post-immunization (FIG. 8B,C,F), and elicited high titers of neutralizing antibodies (about $10^4$) from day 14 to 29 post-immunization (FIG. 8D-F). Consistently, all seroconverted mice were fully protected against infection (FIG. 8B&C), whereas the seronegative mouse from the low-dose (0.3 μg) group generated viremia on day 2 post-challenge (data not shown). The challenge did not boost neutralizing antibody titers in any seroconverted mice (compare the neutralizing antibody titers on days 29 and 43 in FIG. 8D&E). The results demonstrate that immunization of 0.5 μg pZIKV-3'UTR-Δ20 DNA is sufficient to confer 100% seroconversion and protective immunity.

Figure 9:
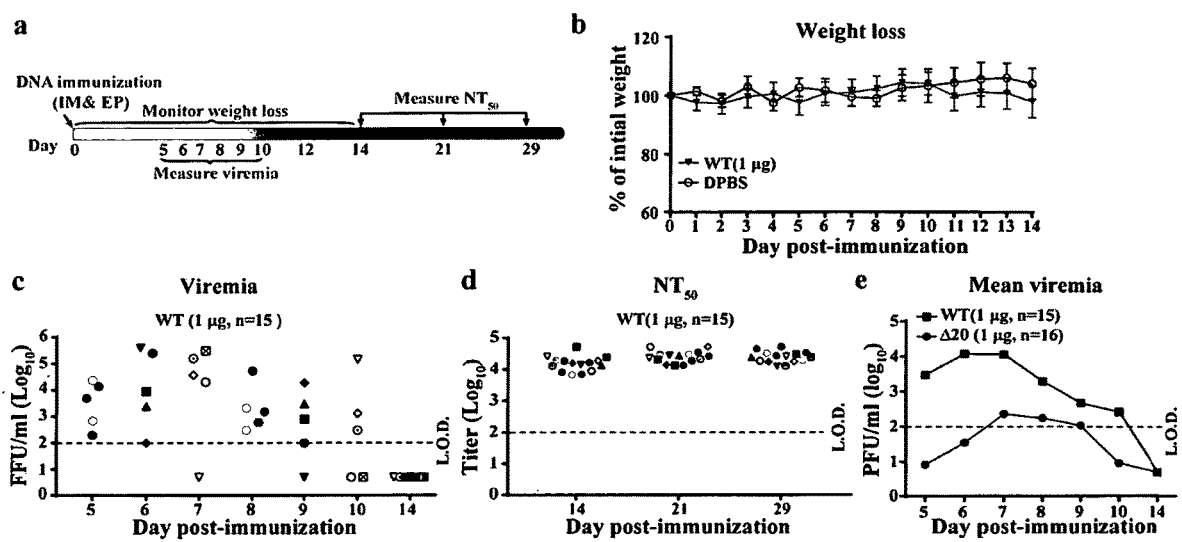
FIG. 9A-E contains a characterization of pZIKV-WT in the A129 mice. (A) Experimental design. Six-week-old A129 mice were immunized with pZIKV-WT (1 µg) or DPBS (sham) using TriGrid™. Following immunization, the mice were monitored for weight loss over 14 days (B). At the indicated time points, the mice were bled for measuring viremia (C) and neutralizing antibody titers (D). Individual mice are indicated by different colors and symbols. (E) Comparison of the mean viremia between the pZIKV-WT- and pZIKV-3'UTR-Δ20 immunized mice. The mean viremia curve for the pZIKV-WT-immunized mice was derived from (C) of this figure. The mean viremia curve for the pZIKV-3'UTR-Δ20-immunized mice was derived from FIG. 2C.

Attenuation of pZIKV-3'UTR-Δ20 in the A129 mice. To validate whether the DNA-launched LAV is attenuated in vivo, we compared the viremia and neutralizing antibody development between the pZIKV-3'UTR-Δ20 and pZIKV-WT in A129 mice (FIG. 9A). After immunizing mice with 1 μg of plasmid DNA, neither pZIKV-3'Δ20 (FIG. 2B) nor pZIKV-WT caused weight loss, disease, or death (FIG. 9B). This is not surprising because ZIKV-inflicted morbidity and mortality are age-dependent in A129 mice [32]. We were not able to use younger mice because their tibialis anterior muscles are too small for consistent dosing by the TriGrid™. Each pZIKV-WT-immunized mouse developed robust viremia (FIG. 9C) and high neutralizing antibody titers (FIG. 9D). The average viremia titers in the pZIKV-WT-immunized group were significantly higher than those in the pZIKV-3'UTR-420-immunized group (FIG. 9E). The results indicate that the pZIKV-3'UTR-Δ20 launched lower viremia than pZIKV-WT in vivo.

Figure 10:
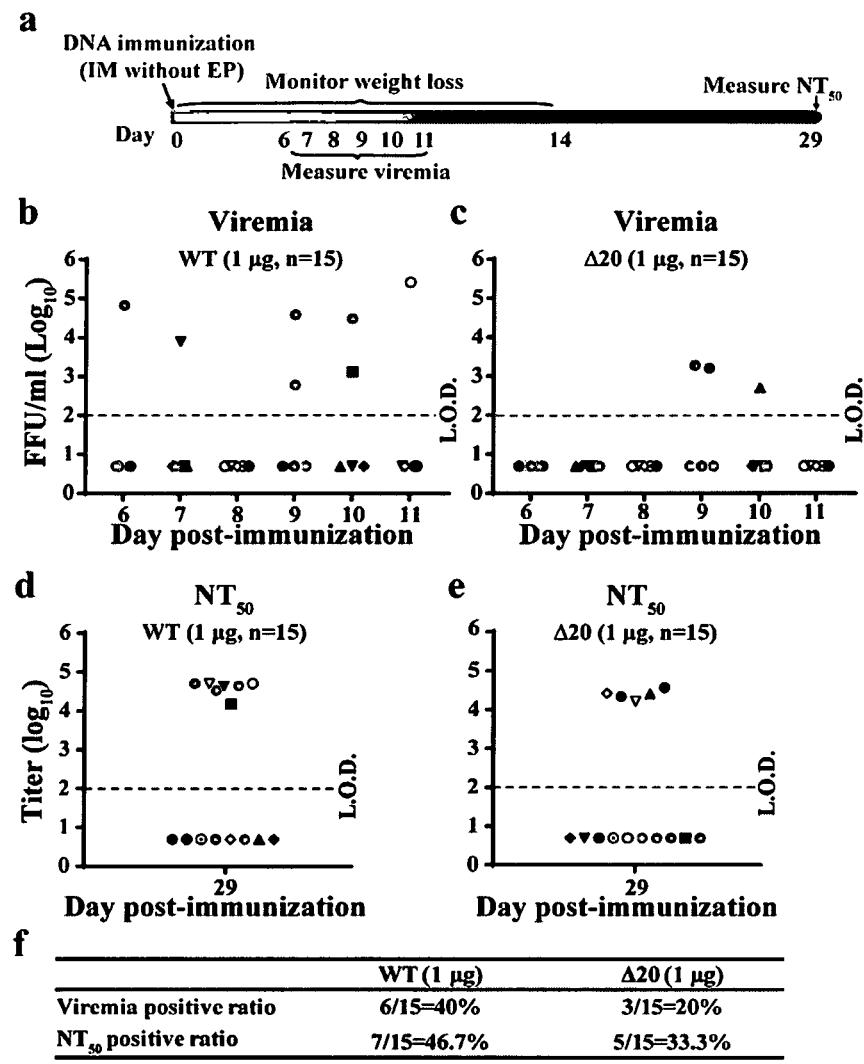
FIG. 10A-F illustrates Efficiency of DNA delivery into the A129 mice by intramuscular (IM) needle injection without electroporation. (A) Experimental design.; Six-week-old A129 mice were immunized with pZIKV-3'UTR-Δ20 (1 µg), pZIKV-WT (1 µg), or DPBS (sham) by IM. Following immunization, the mice were monitored for weight loss over 14 days. The mice were bled on day 6-11 for measuring viremia and on day 29 for determining neutralizing antibody titers. (B) Viremia in the pZIKV-WT-immunized mice. (C) Viremia in the pZIKV-3'UTR-Δ20-immunized mice. (D) Neutralizing antibody titers from the pZIKV-WT-immunized mice on day 29 post-immunization. (E) Neutralizing antibody titers from the pZIKV-3'UTR-Δ20-immunized mice on day 29 post-immunization. Individual mice are indicated by different colors and symbols. (F) Summary of viremia positive and seropositive positive ratios.

TriGrid™ for efficient DNA delivery. To demonstrate the use of TriGrid™ for efficient DNA delivery, we examined the immunization efficiency using the traditional intramuscular needle injection without electroporation. A129 mice were intramuscularly needle injected with 1 μg of pZIKV-WT and pZIKV-3'UTR-Δ20, then analyzed for viremia and neutralizing antibodies (FIG. 10A). After needle injection, 40% (n=6/15) of the pZIKV-WT-immunized animals showed viremia (FIG. 10Bb&F) and 47% (n=7/15) seroconverted (FIG. 10D&F), whereas 20% (n=3/15) of the pZIKV-3'UTR-Δ20-immunized mice showed viremia (FIG. 10C&F) and 33% (n=5/15) seroconverted (FIG. 10E&F). Correlation analysis showed that all mice with detectable viremia after immunization were seroconverted (data not shown). These results demonstrate that, compared with TriGrid™, needle injection alone is much less efficient in DNA delivery, as reflected by viral replication and immunogenicity. Thus, all subsequent mouse experiments were performed using the TriGrid™ device.

Figure 3:
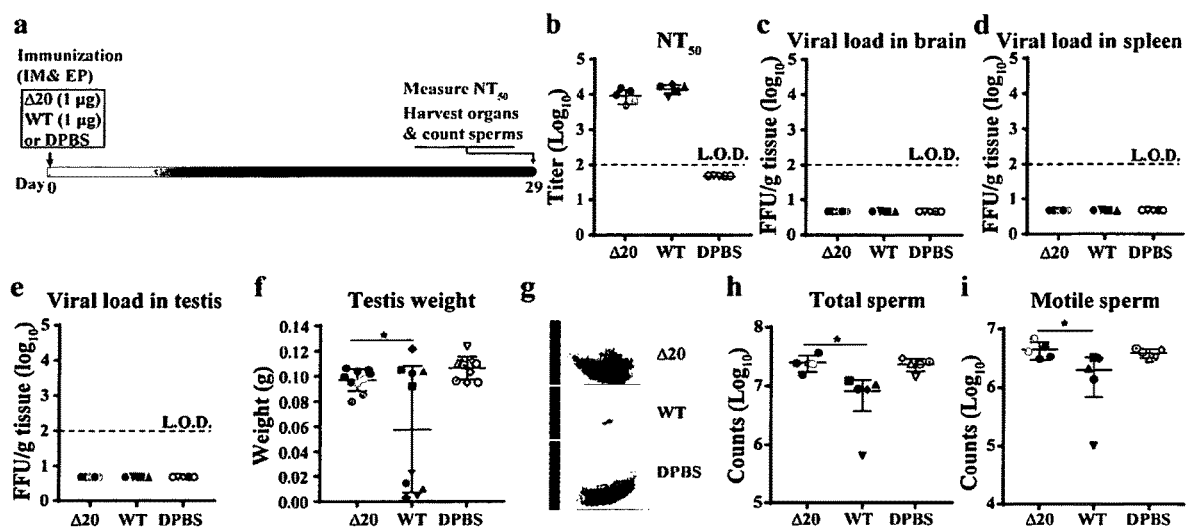
FIG. 3A-I shows the safety of pZIKV-3'UTR-Δ20 in male mice. (A) Experimental design. Six-week-old male A129 mice were immunized with pZIKV-3'UTR-Δ20 (1 μg), pZIKV-WT (1 μg), or DPBS (sham) via intramuscular (IM) injection and electroporation (EP) using TriGrid™. On day 29 post-immunization, mice were sacrificed for analysis. Neutralizing antibody titers were measured on day 29 post-immunization using an mCherry ZIKV neutralization assay (B). Viral loads in mouse brain (C), spleen (D), and testis (E) were determined by a focus-forming assay. The L.O.D.s for organ viral load and $NT_{50}$ were 100 FFU/g of tissue and 100 dilution, respectively. (F) Testis weight. (G) Representative images of testes from each group. The epididymis was harvested for counting total sperm (H) and motile sperm (I). Individual mice are indicated by different colors and symbols. The means and standard deviations are shown. A one-way analysis of variance (ANOVA) test was performed to determine the statistically significant differences among groups.

Protection from ZIKV-induced damages to testes. Since ZIKV infection can persist in the male reproductive tract and lead to sexual transmission [37-39], we examined the ability of pZIKV-3'UTR-Δ20 to prevent testis infection and injury in A129 mice. First, we tested the safety of pZIKV-3'UTR-Δ20 in males (FIG. 3). Six-week-old male mice were immunized with 1 μg of pZIKV-3'UTR-Δ20, 1 μg of pZIKV-WT, or DPBS. On day 29 post-immunization, pZIKV-3'UTR-Δ20 and pZIKV-WT elicited comparable levels of neutralizing antibody titers (FIG. 3B). No infectious virus was detected in brains (FIG. 3C), spleens (FIG. 3D), or testes (FIG. 3E) of pZIKV-3'UTR-Δ20-, pZIKV-WT- or DPBS-immunized mice. Notably, one testis from each of the pZIKV-WT-immunized animals suffered significant weight loss compared with the other testis (FIG. 3F&G). In addition, the pZIKV-WT-immunized animals showed significantly lower total sperm counts (FIG. 3H) and motile sperm counts (FIG. 3I). In contrast, mice immunized with pZIKV-3'UTR-Δ20 or DPBS did not exhibit any weight loss or oligospermia (FIG. 3F-I). We currently don't know what contributed to the uneven weight loss of testis pair from the pZIKV-WT-immunized animals. Nevertheless, the results suggest that pZIKV-3'UTR-Δ20 immunization does not cause persistent infection or oligospermia.

Figure 4:
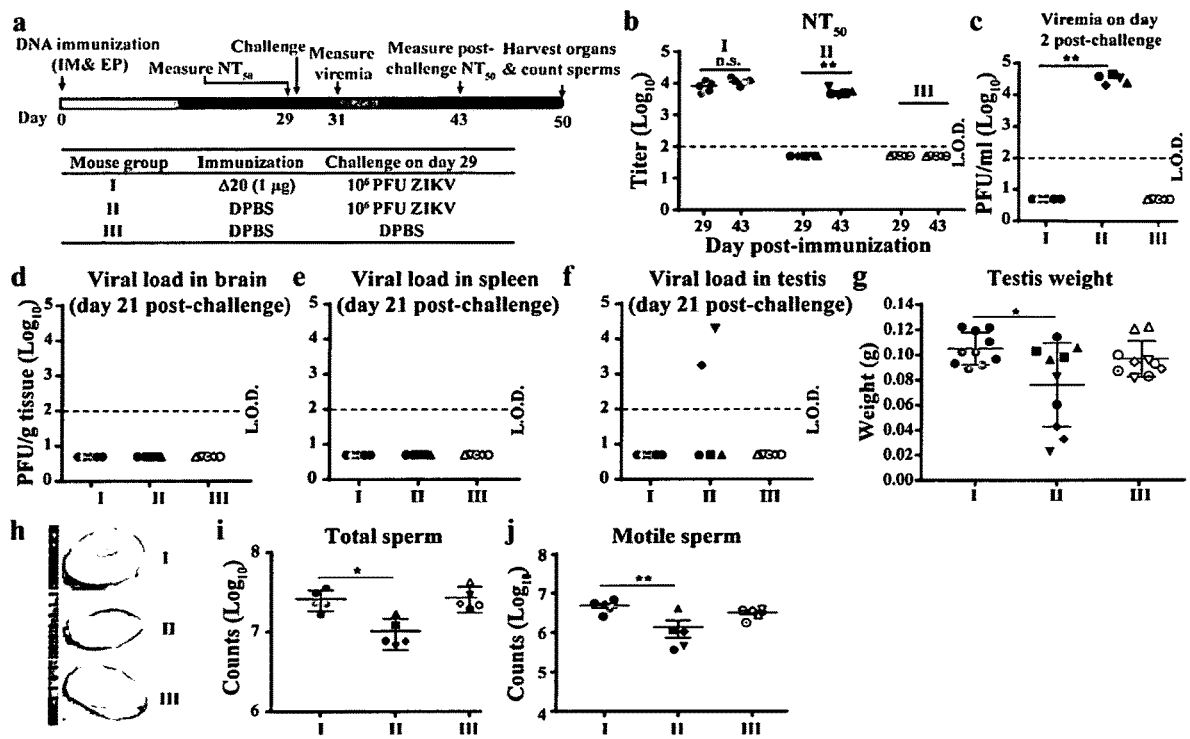
FIG. 4A-J shows immunization with pZIKV-3'UTR-Δ20 protects male mice from ZIKV-induced damages to testis. (A) Experimental design. The bottom panel shows three mouse groups (I, II, and III) with different immunizing agents and challenge conditions. Six-week-old male A129 mice were vaccinated with pZIKV-3'UTR-Δ20 (1 μg) or DPBS (sham) using TriGrid™. On day 29 post-immunization, the mice were challenged with $10^6$ PFU of epidemic ZIKV strain PRVABC59 or DPBS controls. (B) Neutralizing antibody titers on day 29 before challenge and on day 14 post-challenge (equivalent to day 43 post-immunization). Paired t-test was performed to indicate no significant difference (n.s.) between the pre-challenge (day 29) and post-challenge (day 43) neutralizing antibody titers. (C) Viremia on day 2 post-challenge (equivalent to day 31 post-immunization). On day 21 post-challenge, the mice were sacrificed to determine viral loads in brain (D), spleen (E), and testis (F) using a focus-forming assay. (g) Testis weight on day 21 post-challenge. (H) Representative images of testes from each group collected on day 21 post-challenge. The epididymis was harvested for total sperm counts (I) and motile sperm counts (j). Individual mice are indicated by different colors and symbols. A one-way ANOVA test was performed to determine statistically significant differences among groups.

Next, we tested the efficacy of pZIKV-3'UTR-Δ20 in preventing testis infection and damage (FIG. 4A). Six-week-old A129 male mice were immunized with 1 μg of pZIKV-3'UTR-Δ20 or DPBS. By day 29 post-immunization, pZIKV-3'UTR-Δ20 elicited robust neutralizing antibody titers of $10^4$ (FIG. 4B). On the same day, mice were challenged with $10^6$ PFU of ZIKV PRVABC59 by the subcutaneous route. On day 2 post-challenge, no viremia was detected in the pZIKV-3'UTR-Δ20-immunized mice, whereas mean viremia of $3\times10^4$ PFU/ml was detected in the DPBS-immunized group (FIG. 4C). In agreement with the results presented in FIG. 2G, the challenge did not significantly boost neutralizing antibody titers measured on day 14 post-challenge (FIG. 4B). On day 21 post-challenge, we analyzed organ viral loads and testis damage. For the pZIKV-3'UTR-Δ20-immunized group, no virus was detected in brains (FIG. 4D), spleens (FIG. 4E), or testes (FIG. 4F); no weigh loss of testes (FIG. 4G&H) or decrease in total and motile sperm counts (FIG. 4I&J) were observed. In contrast, after challenge, 40% (n=2/5) of the control PBS-immunized mice had virus in the testes (FIG. 4F), smaller testes (FIG. 4G&H), and oligospermia (FIG. 4I&J). Collectively, the data indicate that pZIKV-3'UTR-Δ20 immunization prevents testis infection and oligospermia.

Figure 5:
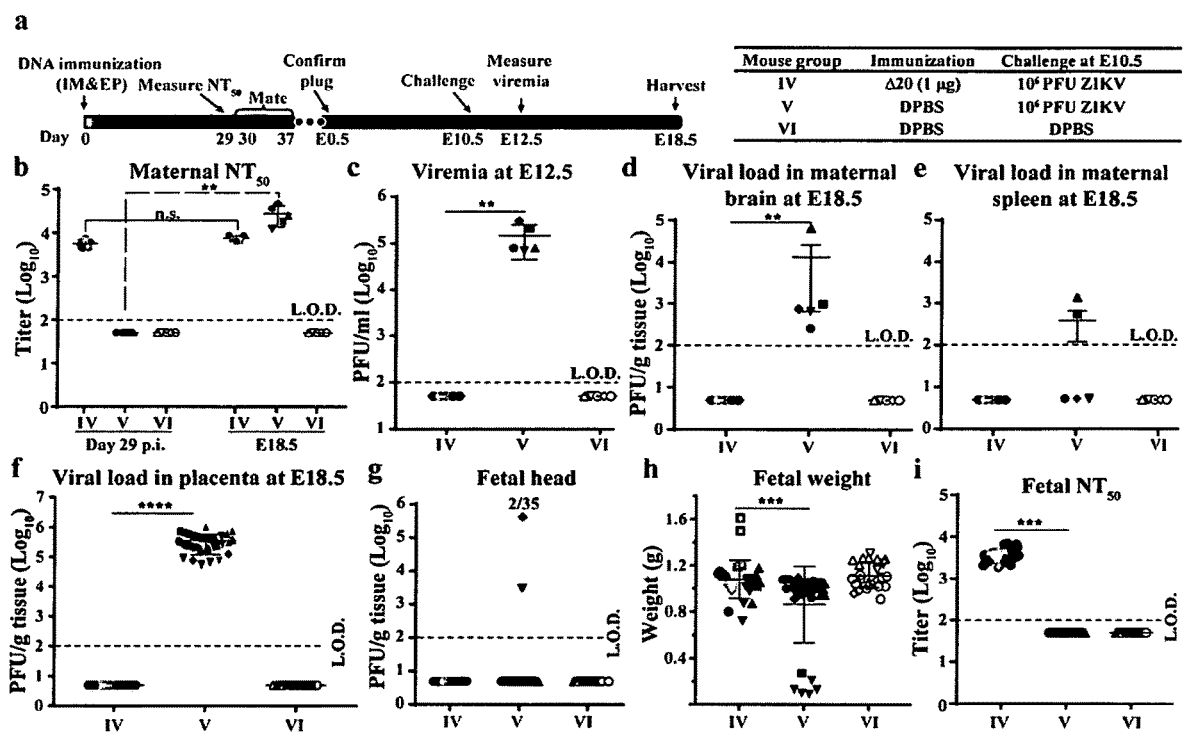
FIG. 5A-I illustrates prevention of vertical transmission from pregnant mice. (A) Experimental design. The right panel shows three mouse groups (IV, V, and VI) with different immunizing agents and challenge conditions. Six-week-old female A129 mice were immunized with pZIKV-3'UTR-Δ20 (1 µg) or DPBS (sham) using TriGrid™. At E10.5, mice were challenged with $10^6$ PFU of ZIKV strain PRVABC59 or DPBS controls via the subcutaneous route. At E18.5, the mice were sacrificed for measuring viral loads in maternal and fetal organs. (B) Maternal $NT_{50}$ values on day 29 post-immunization and at E18.5. For mouse group IV, paired t-test was performed to indicate no significant difference (n.s.) between the pre-challenge (day 29) and post-challenge (E18.5) neutralizing antibody titers. (C) Viremia on day two post-challenge. (D) Maternal brain viral loads. (E) Maternal spleen viral loads. (F) Placenta viral loads. (G) Fetal head viral loads. (H) Fetal weights. (I) Neutralizing antibodies in fetal blood. Individual dams are indicated by different colors and symbols. Fetuses and their parental mice are matched with the same colors and symbols. The L.O.D.s for viremia, organ virus load, and neutralizing antibody titer are 100 PFU/ml, 100 PFU/g, and 100 dilutions, respectively. A one-way ANOVA test was performed to determine statistically significant differences among groups.

Prevention of vertical transmission in pregnant mice. To test the ability of pZIKV-3'UTR-Δ20 to prevent in utero transmission, we immunized six-week-old A129 female mice with 1 µg of pZIKV-3'UTR-Δ20 or DPBS (FIG. 5A). The immunized mice developed high neutralizing antibody titers of $5.6\times10^3$ on day 29 post-immunization (FIG. 5B). Female mice were then mated with males on days 30-37 post-immunization, and examined for pregnancy [indicated by vaginal plugs observed after mating and defining embryotic day 0.5 (E0.5)]. At E10.5, the pregnant mice were challenged with $10^6$ PFU of ZIKV PRVABC59 by the subcutaneous route. No viremia was detected in the pZIKV-3'UTR-Δ20-immunized mice on day 2 post-challenge, whereas viremia of $1.7\times10^6$ PFU/ml was observed in the control DPBS-immunized group (FIG. 5C). At E18.5, the pregnant mice were measured for viral loads in maternal and fetal organs. For the pZIKV-3'UTR-Δ20-immunized group, no infectious virus was detected in maternal brains (FIG. 5D), spleens (FIG. 5E), placentas (FIG. 5F), or in fetal heads (FIG. 5G). Normal fetal weights were observed in the pZIKV-3'UTR-Δ20-immunized mice (FIG. 5H). In contrast, in the DPBS-immunized and challenged group, infectious virus was found in 100% (n=5/5) of maternal brains (FIG. 5D), 40% (n=2/5) of maternal spleens (FIG. 5E), 100% (n=35/35) of placentas (FIG. 5F), and 6% (n=2/35) of fetal heads (FIG. 5G). In addition, significant fetal weight loss was observed in the DPBS-immunized and challenged group.

Next, we asked whether maternal antibodies could be transferred to fetuses after immunization. Indeed, high neutralizing antibody titers of $3.8\times10^3$ were detected from the fetal serum (FIG. 5I). Taken together, the results demonstrate that a single-dose immunization of pZIKV-3'UTR-Δ20 protects maternal organs from infection and prevents maternal-to-fetal transmission.

Figure 6:
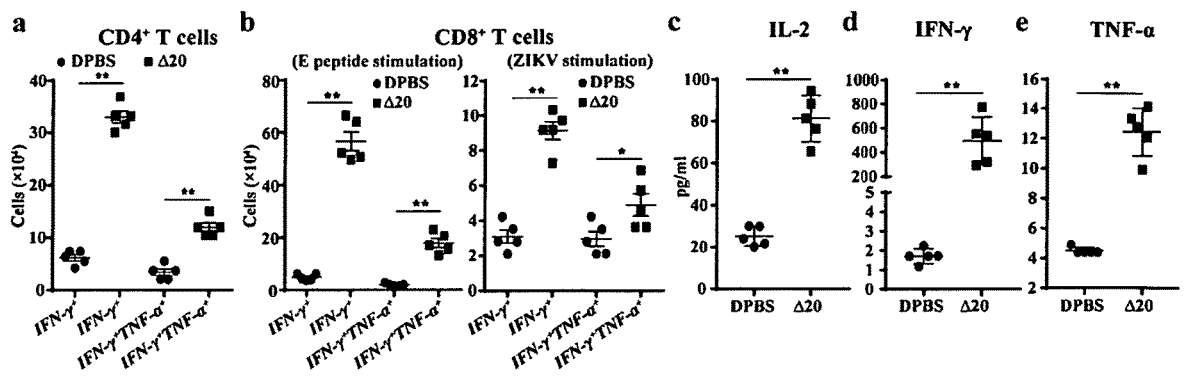
FIG. 6A-E shows T cell responses in A129 mice after pZIKV-3'UTR-Δ20 immunization. Six-week-old A129 mice were immunized with pZIKV-3'UTR-Δ20 (0.5 µg) or DPBS (sham) using TriGrid™. On day 29 post-immunization, splenocytes were harvested for T cell analysis. (A) Total numbers of $CD4^+$ T cell subsets per spleen. Splenocytes were cultured ex vivo with ZIKV for 24 h and stained for IFN-γ, TNF-α, and CD4 T cell markers. (B) Total numbers of $CD8^+$ T cell subsets. Splenocytes were cultured ex vivo with ZIKV for 24 h (right panel) or with an E peptide for 5 h (left panel) and stained for IFN-γ, TNF-α, and CD8 T cell markers. Cytokines IL-2 (C), IFN-γ(D), and TNF-α (E) in cell culture media were measured after splenocytes were stimulated by ZIKV for 2 days. An unpaired nonparametric Mann-Whitney test was performed to analyze statistical significance.
Figure 11:
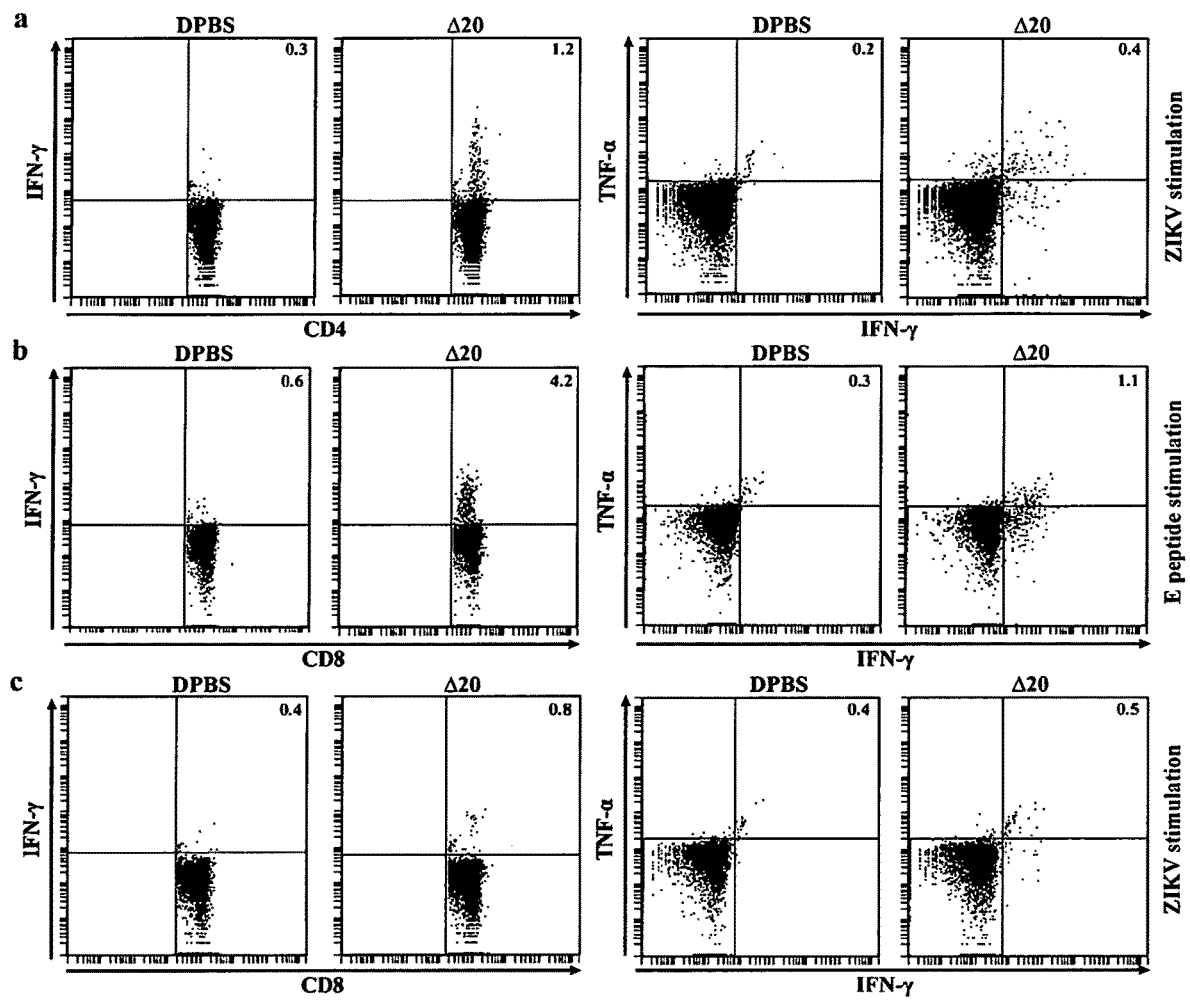
FIG. 11A-C shows T cell response on day 29 post-immunization. Splenocytes were cultured ex vivo with infectious ZIKV for 24 h or a ZIKV E peptide for 5 h, and stained for IFN-γ, TNF-α, and T cell markers. The cells were then gated on $CD4^+$ or $CD8^+$ T cell subsets. Representative flow cytometry images are shown. (A) $CD4^+$ T cell subsets after ZIKV stimulation. (B) $CD8^+$ T cell subsets after the E peptide stimulation. (C) $CD8^+$ T cell subsets after ZIKV stimulation.

T cell response after pZIKV-3'UTR-Δ20 immunization. T cell immunity plays an important role in preventing ZIKV infection [33]. We examined T cell responses in A129 mice immunized with 0.5 µg of pZIKV-3'UTR-Δ20 or DPBS. Mouse spleens were harvested on day 29 post-immunization. Splenocytes were cultured ex vivo, stimulated with a previously reported ZIKV E peptide [33] or infectious WT ZIKV, and analyzed by an intracellular cytokine staining (ICS) assay and a Bio-Plex immunoassay. The pZIKV-3'UTR-Δ20-immunized animals had significantly more ZIKV-specific IFN-γ$^+$ and IFN-γ$^+$TNF-α$^+$ CD4$^+$ (FIG. 6A and FIG. 11A) and CD8$^+$ T cells (FIG. 6B and FIG. 11B&C) than the DPBS-vaccinated animals. In addition, splenocytes from the pZIKV-3'UTR-Δ20-immunized mice produced significantly higher levels of IL-2 (FIG. 6C), IFN-γ (FIG. 6D), and TNF-α (FIG. 6E) proteins than the DPBS-immunized animals upon ex vivo re-stimulation with ZIKV. These data indicate that immunization with pZIKV-3'UTR-Δ20 elicits robust CD4$^+$ and CD8$^+$ T cell responses in mice.

Discussion

Vaccines, especially LAV, have been highly effective in controlling and even eradicating infectious diseases [40]. Enhancing vaccine performance with improved simplicity, immunity, and delivery speed is critical, particularly when responding to epidemic emergency. The goal of this study is to develop and characterize pZIKV-3'UTR-Δ20 that combines the strengths of DNA vaccines (chemical stability, no cold chain, easy production, and low cost) and LAVs (single dose, quick immunity and durable protection). Our results showed that a single-dose vaccination of ≥0.5 µg of pZIKV-3'UTR-Δ20 elicited 100% protective immunity within 14-21 days in the A129 mice. The vaccination completely prevented ZIKV infection, vertical transmission during pregnancy, and male reproductive tract infections. However, due to the detection limits of plaque and focus-forming assays used in this study, we could not exclude the possibility of low levels of viral replication after challenge. Since RT-PCR test is much more sensitive than the plaque and focus-forming assays (FIG. 12), future non-human primate studies should employ RT-PCR assay to detect viral RNA. The RT-PCR assay should also be used in preclinical safety studies to measure viral RNA levels in different organs collected at multiple time points post-vaccination. Besides antibody response, the immunized mice also developed robust T cell responses. The DNA-launched approach could serve as a universal platform to deliver LAVs for other positive-sense, single-stranded RNA viruses. Indeed, such DNA-launched LAVs have been reported for Kunjin virus [41], YFV 17D [42], JEV SA14-14-2 [43], chikungunya virus 181/clone25 strain [44], and Venezuelan equine encephalitis virus TC-83 strain [45]. Compared with previous reports, our study showed the lowest minimal plasmid dose required for 100% protection (0.5 µg) in mice. More importantly, we report, for the first time, that a DNA-launched LAV can elicit robust neutralizing antibody titers as well as robust T cell responses. These results have clearly demonstrated the strengths of the DNA-launched LAV approach.

DNA and mRNA subunit vaccines (expressing viral prM-E proteins) have been well developed for ZIKV [14-18], among which DNA subunit vaccines have already shown promising safety and immunogenicity in phase I clinical trials [20, 21]. Fifty micrograms of subunit DNA [17, 18] and 10-30 µg of subunit RNA [14-16] were used in mouse efficacy experiments. These doses are much higher than the 0.5-µg minimal dose required for 100% seroconversion we demonstrated here for pZIKV-3'UTR-Δ20. However, caution should be taken when comparing the doses used in various studies because of different experimental conditions (e.g., RNA/DNA delivery methods, different promoters used in plasmids and mouse strains). For practical purposes, lowering the minimal protective dose is desirable for a vaccine, particularly when responding to epidemic emergencies that often require the rapid production of millions of doses for vaccinating large populations. In addition, lower doses of DNA plasmid could minimize potential adverse effects in vaccinees. Thus, future studies should be performed to further improve the delivery efficiency of pZIKV-3'UTR-Δ20 by comparing different DNA delivery devices (e.g., injection/electroporation device from Inovio and needle-free injection device from ParmaJet) and through different routes of administration (e.g., intradermal versus intramuscular). Since several of these DNA delivery devices have already been used in clinical trials, these devices will greatly facilitate the advancement of DNA-launched LAVs to clinics. Due to the large size of DNA-launched LAV plasmid (about 18 kb in the case of pZIKV-3'UTR-Δ20), we think that electroporation may contribute significantly to the efficient delivery of large DNA plasmid into cells. Besides the delivery devices discussed above, nanoparticle technology could also be explored for the efficient delivery of the DNA-launched LAVs. Such nanoparticle formulations have to be co-developed with the DNA-launched LAVs in pre-clinics and clinics.

A number of important questions when answered should further enhance the development of pZIKV-3'UTR-Δ20 as a vaccine candidate. For example, the initial cell types that launch ZIKV-3'UTR-Δ20 LAV replication after plasmid electroporation may be elucidated. It is well documented that intramuscular injection with plasmid DNA results in transgene expression primarily in muscle cells. Bone marrow-derived dendritic cells are central to the induction of immune response by DNA vaccines [46]. Engineering pZIKV-3'UTR-Δ20 with a reporter gene (e.g., GFP or mCherry in-frame fused with the viral open-reading-frame) may facilitate tracking the initial production and spread of the DNA-launched LAV. The same experiment may also be used to estimate the duration of LAV production after plasmid vaccination. Additionally, how long will the protective immunity lasts after vaccination with pZIKV-3'UTR-Δ20 may be determined. In non-human primates, two immunizations with a subunit DNA vaccine resulted in short-lived immunogenicity and efficacy (reduced protection and declining neutralizing antibody titers to sub-protective levels at the end of year one) [47]. Since pZIKV-3'UTR-Δ20 launches LAV virus, the durability of protective immunity after vaccination is expected be significantly improved. As of today, the neutralizing antibody titers from the 1-µg pZIKV-3'UTR-Δ20-immunized mice remained >2×10$^3$ four months post-immunization (data not shown). Also, maternal neutralizing antibody transfer was observed from the vaccinated dams to fetuses. The transferred maternal antibodies were presumably IgGs because IgMs cannot cross the placenta. How long the maternally transferred neutralizing activity lasts in protecting the newborn mice against infection may be determined. Further, while some DNA vaccines have shown good efficacy in mice, this efficacy is not always observed in larger animals. Accordingly, while we anticipate that the expression of replicating RNA genome from the DNA-launched platform should improve this outcome, the single-dose mouse efficacy observed here will be validated in non-human primates and humans.

Based on the foregoing, we have developed a plasmid-launched ZIKV LAV that combines the advantages of DNA vaccines and LAVs. A single-dose immunization of our pZIKV-3'UTR-Δ20 induces robust immunity to prevent pregnancy transmission and testis damage in mouse models. Our results suggest that further development of the pZIKV-3'UTR-Δ20 for use in vaccine compositions is warranted, and moreover that the plasmid-launched LAV platform may be applied to other plus-sense, single-stranded RNA viruses.

Example 2

Construction of DNA-Launched YF17D and JE14-14-2 Plasmids.

Materials and Methods: To convert the YF17D and JE14-14-2 to pLAV format, we engineered the complete cDNA copy of individual LAV genome into plasmid pCC1™, resulting in pYF17D and pJE14-14-2, respectively (FIG. 13A). To ensure the clinical relevance of our plasmid constructs, we used viral RNAs, directly extracted from the commercial vaccine lots of YF17D and JE14-14-2 LAVs, as the templates for RT-PCR to create the cDNA clones. The sequence of our YF17D is the same as reported in GenBank (accession number JN628279.1) and the sequence of our JE14-14-2 is presented in FIG. 18. FIG. 19A-B outlines the cloning scheme for pYF17D and pJE14-14-2. The viral RNA was transcribed from a 5' eukaryotic SV40 promoter through cellular RNA polymerase II. We chose SV40 promoter, rather than CMV promoter, because SV40 was reported to more efficiently launch ZIKV pLAV (ZIKV-3'UTR-Δ20) [75]. Sequences representing a hepatitis delta virus ribozyme (HDVr) and a polyadenylation signal were engineered at the 3' end of YF17D or JE14-14-2 cDNA to produce the authentic 3' end of viral RNA and to terminate transcription, respectively. We chose plasmid pCC1™ as the vector because flavivirus cDNA is often unstable in medium and high copy number plasmids [58]. Single copy vector is often essential to maintain the stability of flavivirus cDNA clones. The copy number of pCC1™ plasmid can be conditionally controlled: single copy per *E. coli* during cloning and 10-20 copies per cell during production [79].

Characterization of pYF17D and pJE14-14-2 in cell culture. We examined the production of LAVs from pYF17D and pJE14-14-2 on BHK-21 and Vero cells. After transfection to Vero cells, pYF17D produced a peak viral titer of 1.8×10$^8$ PFU/ml on day 5 p.t. (FIG. 13B). After transfection to BHK-21 cells, pJE14-14-2 generated a peak titer of 3.8×10$^8$ PFU/ml on day 3 p.t. (FIG. 13C). The resulting YF17D and JE14-14-2 LAVs exhibited homogeneous plaque morphologies (FIG. 13D). The results demonstrate that pYF17D and pJE14-14-2 can efficiently launch LAVs in cell culture.

Figure 20A:
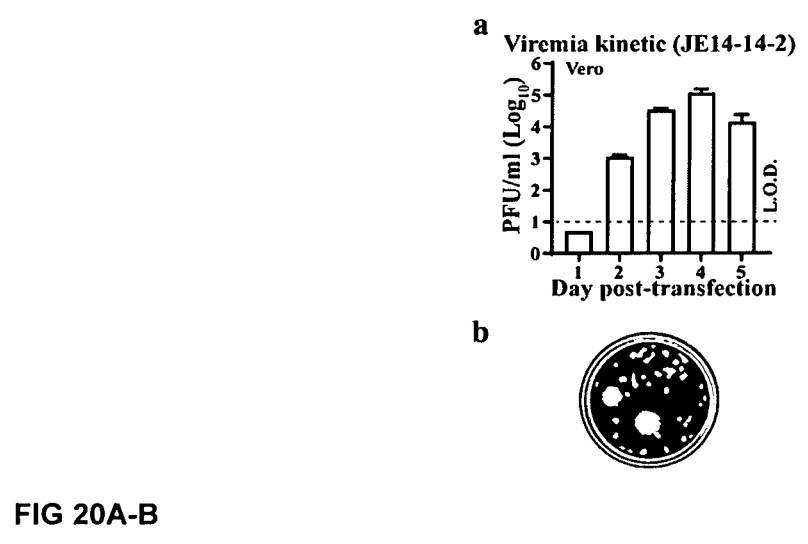

Compared to BHK-21 cells, pJE14-14-2 produced lower amounts of LAV on Vero cells, with peak titers of 1.2×10$^5$ PFU/ml (FIG. 20A). The Vero cell derived JE14-14-2 LAV developed mixed plaque sizes (FIG. 20B), suggesting a selection pressure when JE14-14-2 LAV was cultured on Vero cells.

Analysis of JE14-14-2 variants produced from Vero cells. To define the molecular details of JE14-14-2 variants produced from Vero cells, we continuously passaged the P0 virus (derived from the pJE14-14-2-transfected cells) on Vero cells for five rounds, with 3-5 days per round (FIG. 21A). Two independent selections were performed. In contrast to P0 virus, P1 to P5 viruses exhibited large plaques (FIG. 21B). Whole genome sequencing of the P5 virus from selection I revealed a nucleotide change of A to G at position 1,383, leading to a K136E amino acid mutation in the E protein; whereas the P5 virus from selection II had a nucleotide change of A to C at position 1,473, resulting in a K166Q mutation in the E protein (FIG. 21D). Sequencing of earlier passages showed that the K136E or K166Q mutation emerged at P1 (data not shown). To verify these mutations are responsible for the phenotype of large plaques, we prepared recombinant JE14-14-2 viruses containing the single E K136E or K166Q mutation. The recombinant K136E and K166Q viruses exhibited large plaques that were comparable to the P5 viruses (FIG. 21D), demonstrating that these E mutations are responsible for the emergence of viruses with large plaques on Vero cells. On the crystal structure of JEV E protein, both K136 and K166 are located on the surface of subdomain I (FIG. 21E).

Figure 22A:
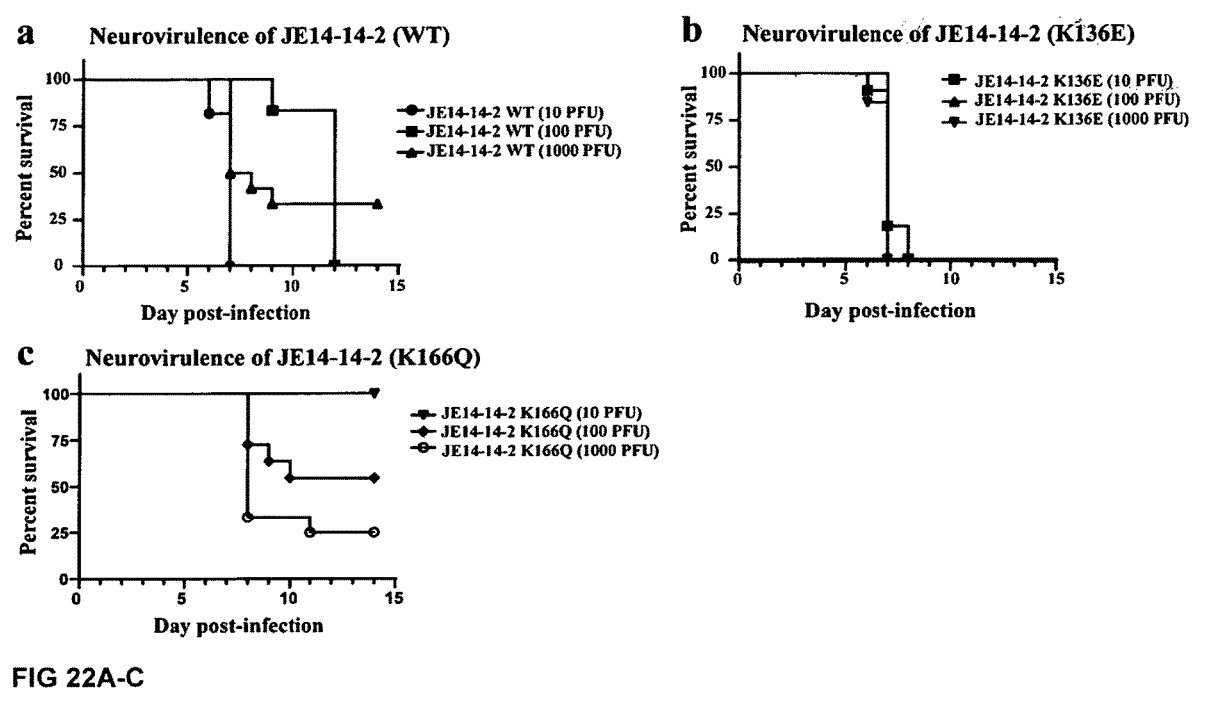

Safety studies: To examine the safety implication of E K136E and K166Q mutations, we compared the neurovirulence of the WT and recombinant mutant JE14-14-2 viruses. One-day-old outbred CD1 pups were intracranially inoculated with 10, 100, or 1,000 PFU of WT, K136E, or K166Q JE14-14-2 viruses. The survival curves showed that mutant K136E increased the neurovirulence, whereas mutant K166Q decreased the neurovirulence (FIG. 22). Collectively, the results demonstrate that, when JE14-14-2 is cultured on Vero cells, mutation K136E or K166Q in E protein could rapidly emerge, leading to increased or decreased neurovirulence, respectively.

YF17D and JE14-14-2 LAVs in A129 mice. We analyzed the morbidity, mortality, and viremia of YF17D and JE14-14-2 LAVs (produced from the pDNA-transfected cells in FIG. 13) in the type-I interferon receptor deficient (Ifnar1−/−) A129 mice (FIG. 14). Nine-week-old mice were subcutaneously infected with $10^4$ PFU of YF17D or $10^5$ PFU of JE14-14-2. Mice inoculated with PBS were included as a control. YF17D infection did not cause disease (data not shown), weight loss (FIG. 14A), or death (FIG. 14B), but developed viremia that peaked on day 2 p.i. (FIG. 14C). In contrast, JE14-14-2 infection caused diseases (including ruffled fur, hunched posture, and squinty eyes), weight loss (FIG. 14D), viremia that peaked on day 3 p.i. (FIG. 14F), and 20% death (FIG. 14E).

Immunogenicity and efficacy of pYF17D. We examined the immunogenicity and efficacy of pYF17D in the A129 mice (FIG. 15A). Nine-week-old mice were immunized with 1, 0.3, or 0.1 µg of pYF17D DNA or PBS. The plasmids were administered to the animals through a clinically used delivery device TriGrid™ [80]. TriGrid™ delivers DNA through an intramuscular injection followed by an electroporation. Since the size of our pLAV is large (~18 kb in size), it is important to include electroporation to enhance the cellular uptake of DNA. As a control, mice were also subcutaneously immunized with $10^5$ PFU of YF17D LAV. None of the pYF17D-immunized mice developed disease, weight loss (FIG. 15B), or viremia (data not shown). On day 14 p.i., 100% of the mice vaccinated with 1 or 0.3 µg of pYF17D developed neutralizing antibodies with titers of ~1/1,000, whereas 60% (3/5) of the animals from the 0.1 µg group developed neutralizing antibodies (FIG. 15C, left panel). The mice inoculated with $10^5$ PFU of YF17D LAV developed neutralizing tiers of ~1/2,000. On day 21 p.i., the mice were bled to measure neutralizing antibody titers and subcutaneously challenged with $10^5$ PFU of YF17D LAV. For the pLAV-immunized mice, the neutralizing antibody titers on day 21 were comparable to those observed on day 14 p.i., whereas the YF17D LAV-vaccinated mice developed slightly higher neutralizing titers (FIG. 15C, right panel). After challenge with YF17D, none of the 1 or 0.3 µg pLAV-immunized mice, as well as the YF17D LAV-vaccinated animals, developed viremia (FIG. 15D). In contrast, for the 0.1 µg of pLAV-immunized group, three mice with neutralizing titers were protected against challenge, whereas two mice without neutralizing titers developed viremia of $2.2 \times 10^4$ PFU/ml on day 2 post-challenge (FIG. 15). As a control, all PBS-inoculated animals developed mean viremia of $3 \times 10^4$ PFU/ml after the challenge. To examine if the challenge boosted the neutralizing antibody levels, we bled the animals on day 14 post-challenge and measured the antibody titers. Remarkably, no increase in neutralizing titers was detected after the challenge (FIG. 15E), suggesting that the initial vaccination may have elicited sterilizing immunity.

Collectively, none of the pYF17D-immunized mice developed disease or weight loss, indicating the safety of the vaccine. Mice immunized with 0.3 µg of pYF17D conferred 100% seroconversion and protection against challenge. All seroconverted animals seemed to have developed sterilizing immunity.

Immunogenicity and efficacy of pJE14-14-2. Next, we tested the immunogenicity and efficacy of pJE14-14-2 in the A129 mice (FIG. 16A). Since 0.1 µg of pYF17D did not confer 100% seroconversion or protection in the A129 mice, we chose to immunize nine-week-old mice with 1 or 0.3 µg of pJE14-14-2. Inoculations with PBS or $10^4$ PFU JE14-14-2 LAV were included as controls. None of the pYF17D-immunized or PBS-inoculated mice developed disease or weight loss (FIG. 16B). As shown in FIG. 14D and FIG. 14E, the JE14-14-2 LAV-infected animals developed disease, wright loss, and 20% death. On days 14 and 21 p.i., all mice from the 1 and 0.3 µg pJE14-14-2 groups, as well as those survived the JE14-14-2 LAV-immunization, developed comparable neutralizing antibody titers of 1/,000 to 1/3,800 (FIG. 16C); none of the PBS-inoculated animals developed neutralizing activities. After challenge with $10^4$ PFU/ml of JE-14-14-2 on day 21 p.i., no viremia was detected in the animals immunized with pLAV or JE-14-14-2 LAV (FIG. 16D), whereas the PBS-inoculated mice developed viremia of $8.3 \times 10^3$ PFU/ml on day 3 post-challenge (FIG. 16D). On day 14 post-challenge, the neutralizing titers from all groups were comparable to those before challenge (compare FIG. 16E with FIG. 16C), indicating that challenge did not boost neutralizing titers. Altogether, the results demonstrate that (i) a single dose of 0.3 µg of pJE14-14-2 is sufficient to confer 100% seroconversion (possibly sterilizing immunity) and 100% protection against JE14-14-2 challenge and (ii) immunization with pJE14-14-2 is safe without causing disease or weight loss in the A129 mice.

Stability of pYF17D and pJE14-14-2. For further development of DNA-launched vaccine platform, the pLAV plasmids should be stable when manufactured in *E. coli*. To examine the stability of pYF17D and pJE14-14-2, we continuously passaged the plasmids in *E. coli* for ten rounds. Plasmids from different passages were compared for their efficiencies to launch LAVs on Vero (for pYF17D) or BHK-21 (for pJE-14-14-2) cells (FIG. 17A). For both pYF17D and pJE14-14-2, plasmids from passage 0 (P0) and 5 (P5) produced equivalent levels of LAVs after transfection with equal amounts of pLAVs (4 µg) into cells (FIG. 17B, C). The LAVs produced from the P0 and P5 plasmids developed identical plaque morphologies (FIG. 5d). These results indicate that both pYF17D and pJE14-14-2 are stable after continuous passages in *E. coli*.

Analysis: As above described we applied our pLAV platform to two clinically licensed flavivirus vaccines: yellow fever 17D (YF17D) and Japanese encephalitis 14-14-2 (JE14-14-2). The cDNA of YF 17D or JE14-14-2 genome was engineered into a DNA plasmid, resulting in pYF17D and pJE14-14-2, respectively. The safety, immunogenicity, and efficacy of the two pLAVs were evaluated in mouse models by immunizing the animals using a clinically proven DNA delivery device TriGrid™. The stability of pYF17D and pJE14-14-2 was also examined by continuously culturing the pLAVs in *E. coli* for five rounds.

Findings: For both YF17D and JE14-14-2, a single-dose immunization with 300 ng of pLAV DNA rapidly elicited protective immunity in mouse models. All mice were seroconverted on day 14 post-immunization. Although no viremia, disease, or weight loss was observed in the pLAV-immunized mice, the immunized animals were 100% protected against viral challenge. No increase in neutralizing antibody titers was detected after viral challenge, suggesting that immunization with 300 ng of pLAV conferred sterilizing immunity. The pYF17D and pJE14-14-2 were stable in *E. coli* for potential scale-up production.

Interpretation: Our results demonstrate that the pLAV platform efficiently delivers clinically approved YF17D or JE14-14-2 vaccines in mice. The simplicity and potency of the pLAV platform may transform the conventional LAV practice by eliminating cell culture (or egg) manufacture and "cold chain" requirement.

Discussion

Our results further demonstrate that the pLAV platform efficiently delivers clinically approved YF17D or JE14-14-2 vaccines in mice. The simplicity and potency of the pLAV platform may transform the conventional LAV practice by eliminating cell culture (or egg) manufacture and "cold chain" requirement.

More generally we demonstrated feasibility of the DNA-launched LAV platform for flavivirus LAVs. Using a DNA delivery device already in human use, we showed that single dose of 300 ng pYF17D or pJE14-14-2 elicited 100% seroconversion and protection against challenge in mice. Compared with our results on a pLAV of ZIKV (i.e., pZIKV-3'UTR-Δ20) [28], the minimal dose for 100% seroconversion reduced from 500 ng to 300 ng, the lowest ever reported for all flavivirus pLAVs [60-62].

Compared with other reports, the improved minimal dose requirement in our studies could result from the enhanced efficiency of DNA delivery device and the design of our pLAVs. Lowering the protective dose offers two advantages. First, it reduces the risk of potential DNA integration, even though no DNA integration to cellular genome has ever been reported in clinics. Second, the dose-sparing quality may facilitate scale-up manufacture of millions of doses in a short timeframe, which is particularly important when responding to public health emergencies. Compared with our pLAV results, 50 μg of subunit DNA [71, 72] and 10-30 μg of subunit RNA [58-68], both expressing ZIKV prM-E proteins, were required to confer efficacy against ZIKV in mice. However, it is acknowledged that comparing minimal effective doses is not entirely predictable especially comparing studies which use different experimental conditions, such as mouse strains and RNA/DNA delivery methods.

Another distinct feature of our pLAVs is that a single-dose immunization of 300 ng DNA elicited neutralizing antibody titers that were not boosted by virus challenge, suggesting that the vaccinated mice developed a sterilizing neutralizing antibody response. The antiviral immunity is determined by the kinetics of LAV production from the pLAV DNA and the immune response to the LAVs. The immune stimulation and development upon pLAV vaccination could be very different from those upon conventional LAV immunization, such differences may account for the development of sterilizing neutralizing antibody response. Further studies are needed to track the spread of the pDNA-launched LAV to antigen-presenting cells, such as dendritic cells, which are essential for the induction of antiviral response [83]. A pLAV with a GFP reporter (engineered in the viral genome) may facilitate such tracking experiments.

Besides the advantages of potential single dose, rapid immune response, and durable protection, the pLAV platform also minimizes the stability concern of conventional LAVs during production on cells or eggs. The pYF17D and pJE14-14-2 were stable after 10 rounds of continuously culturing in *E. coli* (FIG. 17). The DNA-launched chikungunya vaccine was reported to generate fewer reversions of the attenuating mutations compared to conventional virus administration [84]. As demonstrated in this study, cell types are important for maintaining the stability of LAVs during amplification. JE14-14-2 was much less stable when cultured on Vero cells than BHK-21 cells. Two adaptive mutations in the E protein rapidly emerged in LAV after one round of passaging on BHK-21 cells, among which mutation K136E increased neurovirulence, whereas mutation K166Q decreased neurovirulence (FIG. 22). Notably, the neurovirulence-enhancing K136E is located near mutation K138E, which is known to enhance neurovirulence [85]. Both K136E and K138E are on the surface of envelope domain I (FIG. 21E) [86], suggesting that reduced charge of this region of E protein may facilitate virus attachment or cell entry. Similarly, after a DENV-4 LAV was passaged on fetal rhesus lung (FRhL) cells, the virus accumulated an E327G mutation in the E protein that increased the binding affinity for heparin sulfate; however, in that case, the increased binding to heparin sulfate reduced viral infectivity and immunogenicity in rhesus macaques [87].

Future studies should focus on three directions to further develop the DNA-launched platform. First, it is essential to demonstrate the safety and efficacy of the pLAV in non-human primates (NHPs). DNA subunit vaccines (expressing viral envelope proteins) have low immunogenicity in NHPs and humans, despite they often show good efficacy in mice. However, due to the replicative nature of pLAVs, the immunogenicity of pYF17D and pJE14-14-2 is expected to be better than the DNA subunit vaccine. However, this will be experimentally demonstrated in NHPs. Second, improvement of DNA delivery device or nano formulation is important to further reduce the immunizing dose of pLAVs. A lower immunizing dose decreases the cost and increases the safety. The most optimal delivery device will be chosen for each pLAV after comparing the performances of different devices (e.g., injection/electroporation devices such as are available from Ichor and Inovio and needle-free injection devices available from ParmaJet) and through different administration routes (e.g., intradermal versus intramuscular). Third, it is important to determine the durability of the pLAV-mediated protection. In NHPs, two shots of ZIKV DNA subunit vaccine conferred short-lived immunogenicity; the neutralizing antibody titers declined to sub-protective levels at the end of year one [88]. Our unpublished results showed that, after a single immunization with 0.5 μg of pZIKV-3'UTR-420, mice developed high neutralizing antibody titers that did not decline after a year.

Altogether, we have developed plasmid-launched YF17D and JE14-14-2 that combine the advantages of LAV and DNA vaccine. Mice immunized with a single dose of 0.3 μg pLAV developed sterilizing neutralizing titers. These promising results warrant further development of the pLAVs to NHPs and eventually to clinical trials in humans. The pYF17D and pJE14-14-2 have the potential to replace the conventional LAVs against these two important pathogens. The DNA-launched LAV technology could be applied to develop vaccines for other viruses.

One skilled in the art will readily appreciate that the present invention is adapted to carry out the objects and obtain the ends and advantages mentioned, as well as those inherent therein. The prior examples along with the methods, procedures, treatments, molecules, and specific compounds described herein are presently representative of preferred embodiments, are examples, and are not intended as limitations on the scope of the invention. Changes therein and other uses will occur to those skilled in the art which are encompassed within the spirit of the invention as defined by the scope of the claims.

In the following listing of claims, all nucleotide positions are given with reference to the full-length genome sequence of ZIKV strain FSS13025 (GenBank Accession No. KU955593.1) or in the case of YF17D (accession number JN628279.1) or in the case of JE14-14-2 the sequence in FIG. 18 (SEQ ID NO: 1) but are applicable to all homologous sequences, as would be appreciated by one of skill in the art. This includes, for example, homologous flavivirus sequences e.g. ZIKV strain PRVABC59.

The contents of the following references and all other references which are cited in this application are incorporated by reference in their entirety.

In the preceding procedures, various steps have been described. It will, however, be evident that various modifications and changes may be made thereto, and additional procedures may be implemented, without departing from the broader scope of the exemplary procedures as set forth in the claims that follow.

REFERENCES

1. Pierson, T. C. and M. S. Diamond, Flaviviruses p. 747-794. In D. M. Knipe and P. M. Howley (ed), Fields virology, 6th., vol. 1., 2013.
2. Dick, G. W., S. F. Kitchen, and A. J. Haddow, Zika virus. I. Isolations and serological specificity. Trans R Soc Trop Med Hyg, 1952. 46(5): p. 509-20.
3. Aliota, M. T., et al., Zika in the Americas, year 2: What have we learned? What gaps remain? A report from the Global Virus Network. Antiviral Res, 2017. 144: p. 223-246.
4. Ikejezie, J., et al., Zika Virus Transmission—Region of the Americas, May 15, 2015-Dec. 15, 2016. MMWR Morb Mortal Wkly Rep, 2017. 66(12): p. 329-334.
5. Weaver, S. C., et al., Zika virus: History, emergence, biology, and prospects for control. Antiviral Res, 2016. 130: p. 69-80.
6. Costello, A., et al., Defining the syndrome associated with congenital Zika virus infection. Bull World Health Organ, 2016. 94(6): p. 406-406A.
7. Hoen, B., et al., Pregnancy Outcomes after ZIKV Infection in French Territories in the Americas. N Engl J Med, 2018. 378(11): p. 985-994.
8. Dos Santos, T., et al., Zika Virus and the Guillain-Barre Syndrome—Case Series from Seven Countries. N Engl J Med, 2016. 375(16): p. 1598-1601.
9. Shan, C., X. Xie, and P. Y. Shi, Zika Virus Vaccine: Progress and Challenges. Cell Host Microbe, 2018. 24(1): p. 12-17.
10. Xie, X., et al., Small Molecules and Antibodies for Zika Therapy. J Infect Dis, 2017. 216(suppl_10): p. S945-S950.
11. Abbink, P., K. E. Stephenson, and D. H. Barouch, Zika virus vaccines. Nat Rev Microbiol, 2018.
12. Modjarrad, K., et al., Preliminary aggregate safety and immunogenicity results from three trials of a purified inactivated Zika virus vaccine candidate: phase 1, randomised, double-blind, placebo-controlled clinical trials. Lancet, 2017.
13. Abbink, P., et al., Protective efficacy of multiple vaccine platforms against Zika virus challenge in rhesus monkeys. Science, 2016. 353(6304): p. 1129-32.
14. Pardi, N., et al., Zika virus protection by a single low-dose nucleoside-modified mRNA vaccination. Nature, 2017.
15. Richner, J., et al., Vaccine mediated protection against Zika virus induced congenital disease. Cell, 2017. 170: p. 273-283.
16. Richner, J. M., et al., Modified mRNA Vaccines Protect against Zika Virus Infection. Cell, 2017.
17. Dowd, K. A., et al., Rapid development of a DNA vaccine for Zika virus. Science, 2016. 354(6309): p. 237-240.
18. Larocca, R. A., et al., Vaccine protection against Zika virus from Brazil. Nature, 2016. 536(7617): p. 474-8.
19. Chattopadhyay, A., et al., A recombinant virus vaccine that protects against both Chikungunya and Zika virus infections. Vaccine, 2018. 36(27): p. 3894-3900.
20. Gaudinski, M. R., et al., Safety, tolerability, and immunogenicity of two Zika virus DNA vaccine candidates in healthy adults: randomised, open-label, phase 1 clinical trials. Lancet, 2017.
21. Tebas, P., et al., Safety and Immunogenicity of an Anti-Zika Virus DNA
22. Shan, C., et al., A live-attenuated Zika virus vaccine candidate induces sterilizing immunity in mouse models. Nat Med, 2017.
23. Shan, C., et al., A single-dose live-attenuated vaccine prevents Zika virus pregnancy transmission and testis damage. Nat Commun, 2017. 8(1): p. 676.
24. Xie, X., et al., Understanding Zika Virus Stability and Developing a Chimeric Vaccine through Functional Analysis. MBio, 2017. 8(1).
25. Li, X. F., et al., Development of a chimeric Zika vaccine using a licensed live-attenuated flavivirus vaccine as backbone. Nat Commun, 2018. 9(1): p. 673.
26. Ghaffarifar, F., Plasmid DNA vaccines: where are we now? Drugs Today (Barc), 2018. 54(5): p. 315-333.
27. Levine, M. M., "IDEAL" vaccines for resource poor settings. Vaccine, 2011. 29 Suppl 4: p. D116-25.
28. Yang, Y., et al., A cDNA Clone-Launched Platform for High-Yield Production of Inactivated Zika Vaccine. EBioMedicine, 2017. 17: p. 145-156.
29. Shan, C., et al., An Infectious cDNA Clone of Zika Virus to Study Viral Virulence, Mosquito Transmission, and Antiviral Inhibitors. Cell Host Microbe, 2016. 19(6): p. 891-900.
30. Xie, X., et al., Zika Virus Replicons for Drug Discovery. EBioMedicine, 2016. 12: p. 156-160.
31. Dupuy, L. C., et al., A DNA vaccine for venezuelan equine encephalitis virus delivered by intramuscular electroporation elicits high levels of neutralizing antibodies in multiple animal models and provides protective immunity to mice and nonhuman primates. Clin Vaccine Immunol, 2011. 18(5): p. 707-16.
32. Rossi, S. L., et al., Characterization of a Novel Murine Model to Study Zika Virus. Am J Trop Med Hyg, 2016. 94(6): p. 1362-9.
33. Elong Ngono, A., et al., Mapping and Role of the CD8(+) T Cell Response During Primary Zika Virus Infection in Mice. Cell Host Microbe, 2017. 21(1): p. 35-46.

34. Shan, C., et al., A live-attenuated Zika virus vaccine candidate induces sterilizing immunity in mouse models. Nat Med, 2017. 23(6): p. 763-767.
35. Wild, J., Z. Hradecna, and W. Szybalski, Conditionally amplifiable BACs: switching from single-copy to high-copy vectors and genomic clones. Genome Res, 2002. 12(9): p. 1434-44.
36. Cheeseman, H. M., et al., Combined skin and muscle DNA priming provides enhanced humoral responses to an HIV-1 Glade C envelope vaccine. Hum Gene Ther, 2018.
37. Barzon, L., et al., Infection dynamics in a traveller with persistent shedding of Zika virus RNA in semen for six months after returning from Haiti to Italy, January 2016. Euro Surveill, 2016. 21(32).
38. Nicastri, E., et al., Persistent detection of Zika virus RNA in semen for six months after symptom onset in a traveller returning from Haiti to Italy, February 2016. Euro Surveill, 2016. 21(32).
39. Russell, K., et al., Male-to-Female Sexual Transmission of Zika Virus-United States, January-April 2016. Clin Infect Dis, 2017. 64(2): p. 211-213.
40. Minor, P. D., Live attenuated vaccines: Historical successes and current challenges. Virology, 2015. 479-480: p. 379-92.
41. Hall, R. A., et al., DNA vaccine coding for the full-length infectious Kunjin virus RNA protects mice against the New York strain of West Nile virus. Proc. Natl. Acad. Sci. USA, 2003. 100(18): p. 10460-4.
42. Tretyakova, I., et al., Plasmid DNA initiates replication of yellow fever vaccine in vitro and elicits virus-specific immune response in mice. Virology, 2014. 468-470: p. 28-35.
43. Nickols, B., et al., Plasmid DNA launches live-attenuated Japanese encephalitis virus and elicits virus-neutralizing antibodies in BALB/c mice. Virology, 2017. 512: p. 66-73.
44. Tretyakova, I., et al., DNA vaccine initiates replication of live attenuated chikungunya virus in vitro and elicits protective immune response in mice. J Infect Dis, 2014. 209(12): p. 1882-90.
45. Tretyakova, I., et al., Novel vaccine against Venezuelan equine encephalitis combines advantages of DNA immunization and a live attenuated vaccine. Vaccine, 2013. 31(7): p. 1019-25.
46. Dupuis, M., et al., Distribution of DNA vaccines determines their immunogenicity after intramuscular injection in mice. J Immunol, 2000. 165(5): p. 2850-8.
47. Abbink, P., et al., Durability and correlates of vaccine protection against Zika virus in rhesus monkeys. Sci Transl Med, 2017. 9(420). 48. Bhatt, S., et al., The global distribution and burden of dengue. Nature, 2013. 496 (7446): p. 504-7.
49. The, L., Yellow fever: a global reckoning. Lancet, 2016. 387(10026): p. 1348.
50. Campbell, G. L., et al., Estimated global incidence of Japanese encephalitis: a systematic review. Bull World Health Organ, 2011. 89(10): p. 766-74, 774A-74E
51. Ikejezie, J., et al., Zika Virus Transmission—Region of the Americas, May 15, 2015-Dec. 15, 2016. MMWR Morb Mortal Wkly Rep, 2017. 66(12): p. 329-334.
52. Lim, S. P., et al., Ten years of dengue drug discovery: Progress and prospects. Antiviral Res, 2013. 100(2): p. 500-19.
53. Shan, C., et al., Zika Virus: Diagnosis, Therapeutics, and Vaccine ACS Infectious Diseases, 2016. 2: p. 170-2.
54. Pierson, T. C. and M. S. Diamond, Flaviviruses p. 747-794. In D. M. Knipe and P. M. Howley (ed), Fields virology, 6th., vol. 1., 2013.
55. Rice, C. M., et al., Transcription of infectious yellow fever RNA from full-length cDNA templates produced by in vitro ligation. New Biologist, 1989. 1(3): p. 285-96.
56. Lai, C. J., et al., Infectious RNA transcribed from stably cloned full-length cDNA of dengue type 4 virus. Proceedings of the National Academy of Sciences of the United States of America, 1991. 88(12): p. 5139-43.
57. Khromykh, A. A. and E. G. Westaway, Completion of Kunjin virus RNA sequence and recovery of an infectious RNA transcribed from stably cloned full-length cDNA. Journal of Virology, 1994. 68(7): p. 4580-8.
58. Shi, P. Y., et al., Infectious cDNA clone of the epidemic West Nile virus from New York City. J. Virol., 2002. 76(12): p. 5847-56.
59. Yun, S. I., et al., Development and application of a reverse genetics system for Japanese encephalitis virus. J Virol, 2003. 77(11): p. 6450-65.
60. Shan, C., et al., An Infectious cDNA Clone of Zika Virus to Study Viral Virulence, Mosquito Transmission, and Antiviral Inhibitors. Cell Host Microbe, 2016. 19(6): p. 891-900.
61. Zou, G., et al., Development and characterization of a stable luciferase dengue virus for high-throughput screening. Antiviral Res, 2011. 91(1): p. 11-9.
62. Levine, M. M., "IDEAL" vaccines for resource poor settings. Vaccine, 2011. 29 Suppl 4: p. D116-25.
63. Maruggi, G., et al., mRNA as a Transformative Technology for Vaccine Development to Control Infectious Diseases. Mol Ther, 2019. 27(4): p. 757-772.
64. Erasmus, J. H., et al., A Nanostructured Lipid Carrier for Delivery of a Replicating Viral RNA Provides Single, Low-Dose Protection against Zika. Mol Ther, 2018. 26(10): p. 2507-2522.
65. Samsa, M. M., et al., Self-Amplifying RNA Vaccines for Venezuelan Equine Encephalitis Virus Induce Robust Protective Immunogenicity in Mice. Mol Ther, 2019. 27(4): p. 850-865.
66. Richner, J., et al., Vaccine mediated protection against Zika virus induced congenital disease. Cell, 2017. 170: p. 273-283.
67. Richner, J. M., et al., Modified mRNA Vaccines Protect against Zika Virus Infection. Cell, 2017.
68. Pardi, N., et al., Zika virus protection by a single low-dose nucleoside-modified mRNA vaccination. Nature, 2017.
69. Pushko, P., et al., DNA-launched live-attenuated vaccines for biodefense applications. Expert Rev Vaccines, 2016. 15(9): p. 1223-34.
70. Hall, R. A., et al., DNA vaccine coding for the full-length infectious Kunjin virus RNA protects mice against the New York strain of West Nile virus. Proc. Natl. Acad. Sci. USA, 2003. 100(18): p. 10460-4.
71. Tretyakova, I., et al., Plasmid DNA initiates replication of yellow fever vaccine in vitro and elicits virus-specific immune response in mice. Virology, 2014. 468-470: p. 28-35.
72. Nickols, B., et al., Plasmid DNA launches live-attenuated Japanese encephalitis virus and elicits virus-neutralizing antibodies in BALB/c mice. Virology, 2017. 512: p. 66-73.
73. Tretyakova, I., et al., DNA vaccine initiates replication of live attenuated chikungunya virus in vitro and elicits protective immune response in mice. J Infect Dis, 2014. 209(12): p. 1882-90.

74. Tretyakova, I., et al., *Novel vaccine against Venezuelan equine encephalitis combines advantages of DNA immunization and a live attenuated vaccine.* Vaccine, 2013. 31(7): p. 1019-25.
75. Zou, J., et al., *A single-dose plasmid-launched live-attenuated Zika vaccine induces protective immunity.* EBioMedicine, 2018. 36: p. 92-102.
76. Monath, T. P., *Review of the risks and benefits of yellow fever vaccination including some new analyses.* Expert Rev Vaccines, 2012. 11(4): p. 427-48.
77. Ginsburg, A. S., et al., *Use of the live attenuated Japanese Encephalitis vaccine SA 14-14-2 in children: A review of safety and tolerability studies.* Hum Vaccin Immunother, 2017. 13(10): p. 2222-2231.
78. Barrett, A. D. T., *Yellow fever live attenuated vaccine: A very successful live attenuated vaccine but still we have problems controlling the disease.* Vaccine, 2017. 35(44): p. 5951-5955.
79. Wild, J., Z. Hradecna, and W. Szybalski, *Conditionally amplifiable BACs: switching from single-copy to high-copy vectors and genomic clones.* Genome Res, 2002. 12(9): p. 1434-44.
80. Cheeseman, H. M., et al., *Combined skin and muscle DNA priming provides enhanced humoral responses to an HIV-1 clade C envelope vaccine.* Hum Gene Ther, 2018.
81. Dowd, K. A., et al., *Rapid development of a DNA vaccine for Zika virus.* Science, 2016. 354(6309): p. 237-240.
82. Larocca, R. A., et al., *Vaccine protection against Zika virus from Brazil.* Nature, 2016. 536(7617): p. 474-8.
83. Dupuis, M., et al., *Distribution of DNA vaccines determines their immunogenicity after intramuscular injection in mice.* J Immunol, 2000. 165(5): p. 2850-8.
84. Hidajat, R., et al., *Next generation sequencing of DNA-launched Chikungunya vaccine virus.* Virology, 2016. 490: p. 83-90.
85. Yun, S. I., et al., *Comparison of the live-attenuated Japanese encephalitis vaccine SA14-14-2 strain with its pre-attenuated virulent parent SA14 strain: similarities and differences in vitro and in vivo.* J Gen Virol, 2016. 97(10): p. 2575-2591.
86. Luca, V. C., et al., *Crystal structure of the Japanese encephalitis virus envelope protein.* J Virol, 2012. 86(4): p. 2337-46.
87. Anez, G., et al., *Passage of dengue virus type* 4 *vaccine candidates in fetal rhesus lung cells selects heparin-sensitive variants that result in loss of infectivity and immunogenicity in rhesus macaques*. J Virol, 2009. 83(20): p. 10384-94.

88. Abbink, P., et al., *Durability and correlates of vaccine protection against Zika virus in rhesus monkeys*. Sci Transl Med, 2017. 9(420).

The invention claimed is:

1. An immunogenic composition comprising a DNA plasmid comprising from 5' to 3' (a) a promoter segment active in a mammalian cell, (b) a cDNA of a live-attenuated Zika virus (ZIKV) genome comprising (i) a 5' untranslated region, (ii) a coding region for the live-attenuated Zika virus (ZIKV), and (iii) a 3' untranslated region, (c) a hepatitis delta virus ribzyme (HDVr) segment, and (d) a polyadenylation signal.

2. The immunogenic composition of claim 1, wherein the ZIKV has a 3'UTR deletion of the nucleotides at positions 10640 to 10659 of the full-length genomic sequence.

3. An immunogenic composition of claim 1, further comprising at least one pharmaceutically acceptable carrier or excipient and/or adjuvant.

4. The immunogenic composition of claim 3, wherein the composition is formulated for administration by injection or in vivo electroporation.

5. A method of eliciting an immune response in a subject comprising administering an effective amount of an immunogenic composition of claim 1.

6. The method of claim 5, wherein the subject is a human.

* * * * *

SEQUENCE LISTING

<160> NUMBER OF SEQ ID NOS: 1

<210> SEQ ID NO 1
<211> LENGTH: 10977
<212> TYPE: DNA
<213> ORGANISM: Artificial Sequence
<220> FEATURE:
<223> OTHER INFORMATION: Genome sequence of JE14-14-2

<400> SEQUENCE: 1
agaagtttat ctgtgtgaac ttcttggctt agtatcgtag agaagaatcg agagattagt 60
gcagtttaaa cagtttttta gaacggaaga taaccatgac taaaaaacca ggagggcccg 120
gtaaaaaccg ggctatcaat atgctgaaac gcggcctacc ccgcgtattc ccactagtgg 180
gagtgaagag ggtagtaatg agcttgttgg acggcagagg gccagtacgt ttcgtgctgg 240
ctcttatcac gttcttcaag tttacagcat tagccccgac caaggcgctt tcaggccgat 300
ggaaagcagt ggaaaagagt gtggcaatga aacatcttac tagtttcaaa cgagaacttg 360
gaacactcat tgacgccgtg aacaagcggg gcagaaagca aaacaaaaga ggaggaaatg 420
aaggctcaat catgtggctc gcgagcttgg cagttgtcat agcttgtgca ggagccatga 480
agttgtcgaa tttccagggg aagcttttga tgaccatcaa caacacggac attgcagacg 540
ttatcgtgat tcccacctca aaaggagaga acagatgctg ggtccgggca atcgacgtcg 600
gctacatgtg tgaggacact atcacgtacg aatgtcctaa gcttaccatg ggcaatgatc 660
cagaggatgt ggattgctgg tgtgacaacc aagaagtcta cgtccaatat ggacggtgca 720
cgcggaccag gcattccaag cgaagcagga gatccgtgtc ggtccaaaca catggggaga 780
gttcactagt gaataaaaaa gaggcttggc tggattcaac gaaagccaca cgatatctca 840
tgaaaactga gaactggatc ataaggaatc ctggctatgc tttcctggcg gcggtacttg 900
gctggatgct tggcagtaac aacggtcaac gcgtggtatt taccatcctc ctgctgttgg 960
tcgctccggc ttacagtttt aattgtctgg gaatgggcaa tcgtgacttc atagaaggag 1020

```
ccagtggagc cacttgggtg gacttggtgc tagaaggaga cagctgcttg acaatcatgg    1080
caaacgacaa accaacattg gacgtccgca tgattagcat cgaagctagc caacttgctg    1140
aggtcagaag ttactgctat catgcttcag tcactgacat ctcgacggtg gctcggtgcc    1200
ccacgactgg agaagcccac aacgagaagc gagctgatag tagctatgtg tgcaaacaag    1260
gcttcactga ccgtgggtgg ggcaacggat gtggattttt cgggaaggga agcattgaca    1320
catgtgcaaa attctcctgc accagtaaag cgattgggag aacaatccag ccagaaaaca    1380
tcaaatacaa agttggcatt tttgtgcatg gaaccaccac ttcggaaaac catgggaatt    1440
attcagcgca agtggggcg tcccaggcgg caaagtttac agtaacaccc aatgctcctt    1500
cggtagccct caaacttggt gactacggag aagtcacact ggactgtgag ccaaggagtg    1560
gactgaacac tgaagcgttt tacgtcatga ccgtggggtc aaagtcattt ctggtccata    1620
gggagtggtt tcatgacctc gctctcccct ggacgtcccc ttcgagcaca gcgtggagaa    1680
acagagaact cctcatggaa tttgaagggg cgcacgccac aaaacagtcc gttgttgctc    1740
ttgggtcaca ggaaggaggc ctccatcatg cgttggcagg agccatcgtg gtggagtact    1800
caagctcagt gaagttaaca tcaggccacc tgaaatgtag gctgaaaatg acaaactgg    1860
ctctgaaagg cacaacctat ggcatgtgta cagaaaaatt ctcgttcgcg aaaaatccgg    1920
tggacactgg tcacggaaca gttgtcattg aactctccta ctctgggagt gatggcccct    1980
gcaaaattcc gattgtttcc gttgcgagcc tcaatgacat gacccccgtt gggcggctgg    2040
tgacagtgaa ccccttcgtc gcgacttcca gtgccaactc aaaggtgctg gtcgagatgg    2100
aaccccccctt cggagactcc tacatcgtag ttggaagggg agacaagcag atcaaccacc    2160
attggcacaa agctggaagc acgctgggca aggcctttc aacaactttg aagggagctc    2220
aaagactggc agcgttgggc gacacagcct gggactttgg ctctattgga ggggtcttca    2280
actccatagg aagagccgtt caccaagtgt ttggtggtgc cttcagaaca ctctttgggg    2340
gaatgtcttg gatcacacaa gggctaatgg gtgccctact gctctggatg ggcgtcaacg    2400
cacgagaccg atcaattgct ttggccttct tagccacagg aggtgtgctc gtgttcttag    2460
cgaccaatgt gcatgctgac actggatgtg ccattgacat cacaagaaaa gagatgagat    2520
gtggaagtgg catcttcgtg cacaacgacg tggaagcctg ggtggatagg tataaatatt    2580
tgccagaaac gcccagatcc ctagcgaaga tcgtccacaa agcgcacaag gaaggcgtgt    2640
gcggagtcag atctgtcact agactggagc accaaatgtg ggaagccgta agggacgaat    2700
tgaacgtcct gctcaaagag aatgcagtgg acctcagtgt ggttgtgaac aagcccgtgg    2760
gaagatatcg ctcagcccct aaacgcctat ccatgacgca agagaagttt gaaatgggct    2820
ggaaagcatg ggaaaaagc atcctctttg ccccggaatt ggctaactcc acatttgtcg    2880
tagatggacc tgagacaaag gaatgccctg atgagcacag agcttggaac agcatgcaaa    2940
tcgaagactt cggctttggc atcacatcaa cccgtgtgtg gctgaaaatt agagaggaga    3000
gcactgacga gtgtgatgga gcgatcatag gcacggctgt caaggacat gtggcagtcc    3060
atagtgactt gtcgtactgg attgagagtc gctacaacga cacatggaaa cttgagaggg    3120
cagtctttgg agaggtcaaa tcttgcactt ggccagagac acacacccct tggggagatg    3180
atgttgagga aagtgaactc atcattccgc acaccatagc cggaccaaaa agcaagcaca    3240
atcggaggga agggtataag acacaaaacc agggaccttg gatgagaat ggcatagtct    3300
tggactttga ttattgccca gggacaaaag tcaccattac agaggattgt agcaagagag    3360
gcccttcggt cagaaccact actgacagtg gaaagttgat cactgactgg tgctgtcgca    3420
```

```
gttgctccct tccgccccta cgattccgga cagaaaatgg ctgctggtac ggaatggaaa    3480
tcagacctgt tatgcatgat gaaacaacac tcgtcagatc acaggttcat gctttcaaag    3540
gtgaaatggt tgacccttt cagctgggcc ttctggtgat gtttctggcc acccaggaag    3600
tccttcgcaa gaggtggacg gccagattga ccattcctgc ggttttgggg gtcctacttg    3660
tgctgatgct tgggggtatc acttacactg atttggcgag gtatgtggtg ctagtcgctg    3720
ctgctttcgc agaggccaac agtggaggag acgtcctgca ccttgctttg attgctgttt    3780
ttaagatcca accagcattt ttagtgatga acatgcttag cacgagatgg acgaaccaag    3840
aaaacgtggt tctggtccta ggggctgcct ttttccaatt ggcctcagta gatctgcaaa    3900
taggagtcca cggaatcctg aatgccgccg ctatagcatg gatgattgtc cgagcgatca    3960
ccttccccac aacctcctcc gtcaccatgc cagtcttagc gcttctaact ccggggatga    4020
gggctctata cctagacact tacagaatca tcctcctcgt catagggatt tgctccctgc    4080
tgcacgagag gaaaaagacc atggcgaaaa agaaggagc tgtactcttg gcttagcgc     4140 tcacatccac tggatggttc tcgcccacca ctatagctgc cggactaatg gtctgcaacc    4200
caaacaagaa gagagggtgg ccagctactg agtttttgtc ggcagttgga ttgatgtttg    4260
ccatcgtagg tggtttggcc gagttggata ttgaatccat gtcaataccc ttcatgctgg    4320
caggtctcat ggcagtgtcc tacgtggtgt caggaaaagc aacagatatg tggcttgaac    4380
gggccgccga catcagctgg gatatgggtg ctgcaatcac aggaagcagt cggaggctgg    4440
atgtgaaact ggatgatgac ggagattttc acttgattga tgatcccggt gttccatgga    4500
aggtctgggt cctgcgcatg tcttgcattg gcttagccgc cctcacgcct tgggccatcg    4560
ttcccgccgc tttcggttat tggctcactt taaaaacaac aaaaagaggg ggcgtgtttt    4620
gggacacgcc atccccaaaa ccttgctcaa aaggagacac cactacagga gtctaccgaa    4680
ttatggctag agggattctt ggcacttacc aggccggcgt cggagtcatg tacgagaatg    4740
ttttccacac actatggcac acaactagag gagcagccat tgtgagtgga aaggaaaat    4800 tgacgccata ctgggggtagt gtgaaagaag accgcatagc ttacggaggc ccatggaggt    4860
ttgaccgaaa atggaatgga acagatgacg tgcaagtgat cgtggtagaa ccggggaagg    4920
gcgcagtaaa catccagaca aaaccaggag tgtttcggac tcccttcggg gaggttgggg    4980
ctgttagtct ggattacccg cgaggaacat ccggctcacc cattctgat tccaatggag    5040 acattatagg cctatacggc aatggagttg agcttggcga tggctcatac gtcagcgcca    5100
tcgtgcaggg tgaccgtcag gaggaaccag tcccagaagc ttacaccccca acatgttga    5160 gaaagagaca gatgactgtg ctagatttgc accctggtc agggaaaacc aggaaaattc    5220
tgccacaaat aattaaggac gctatccagc agcgcctaag aacagctgtg ttggcaccga    5280
cgcgggtggt agcagcagaa atggcagaag ttttgagagg gctcccagta cgatatcaaa    5340
cttcagcagt gcagagagag caccaaggga atgaaatagt ggatgtgatg tgccacgcca    5400
ctctgaccca tagactgatg tcaccgaaca gagtgcccaa ctacaaccta tttgtcatgg    5460
atgaagctca ttcaccgac ccagccagta tagccgcacg aggatacatt gctaccaagg    5520
tggaattagg ggaggcagca gccatctta tgacagcgac cccgcctgga accacggatc    5580
cttttcctga ctcaaatgcc ccaatccatg atttgcaaga tgagatacca gacagggcat    5640
ggagcagtgg atacgaatgg atcacagaat atgcgggtaa aaccgtgtgg tttgtggcga    5700
gcgtaaaaat ggggaatgag attgcaatgt gcctccaaag agcggggaaa aaggtcatcc    5760
```

```
aactcaaccg caagtcctat gacacagaat acccaaaatg taagaatgga gactgggatt    5820
ttgtcattac caccgacatc tctgaaatgg gggccaactt cggtgcgagc agggtcatcg    5880
actgtagaaa gagcgtgaaa cccaccatct tagaagaggg agaaggcaga gtcatcctcg    5940
gaaacccatc tcccataacc agtgcaagcg cagctcaacg gaggggcaga gtaggcagaa    6000
accccaatca agttggagat gaataccact atggggggc taccagtgaa gatgacagta     6060
acctagccca ttggacagag gcaaagatca tgttagacaa catacacatg cccaatggac    6120
tggtggccca gctctatgga ccagagaggg aaaaggcttt cacaatggat ggcgaatacc    6180
gtctcagagg tgaagaaaag aaaaacttct tagagctgct taggacggct gacctcccgg    6240
tgtggctggc ctacaaggtg gcgtccaatg gcattcagta caccgacaga aagtggtgtt    6300
ttgatgggcc gcgtacgaat gccatactgg aggacaacac cgaggtagag atagtcaccc    6360
ggatgggtga gaggaaaatc ctcaagccga gatggcttga tgcaagagtt tatgcagatc    6420
accaggccct caagtggttc aaagactttg cagcagggaa gagatcagcc gttagcttca    6480
tagaggtgct cggtcgcatg cctgagcatt tcatgggaaa gacgcgggaa gctttagaca    6540
ccatgtactt ggttgcaacg gctgagaaag gtgggaaagc acaccgaatg gctctcgaag    6600
agctgccaga tgcactggaa accatcacac ttattgtcgc cattactgtg atgacaggag    6660
gattcttcct actaatgatg cagcgaaagg gtataggaaa gatgggtctt ggagctctag    6720
tgctcacact agctaccttc ttcctgtggg cggcagaggt tcctggaacc aaaatagcag    6780
ggaccctgct gatcgccctg ctgctgatgg tggttctcat cccagaaccg gaaaaacaga    6840
ggtcacagac agataaccaa ctggcggtgt ttctcatctg tgtcttgacc gtggttggag    6900
tggtggcagc aaacgagtac gggatgctag aaaaaaccaa agcggatctc aagagcatgt    6960
ttggcggaaa gacgcaggca tcaggactga ctggattgcc aagcatggca ctggacctgc    7020
gtccagccac agcctgggca ctgtatgggg ggagcacagt cgtgctaacc cctcttctga    7080
agcacctgat cacgtcggaa tacgtcacca tcgctagc ttcaattaac tcacaagctg      7140
gctcattatt cgtcttgcca cgaggcgtgc cttttaccga cctagacttg actgttggcc    7200
tcgtcttcct tggctgttgg ggtcaagtca ccctcacaac gtttctgaca gccatggttc    7260
tggcgacact tcactatggg tacatgctcc ctggttggca agcagaagca ctcagggctg    7320
cccagagaag gacagcggct ggaataatga agaatgccgt tgttgacgga atggtcgcca    7380
ctgatgtgcc tgaactggaa aggactactc ctctgatgca aagaaagtc ggacaggtgc     7440
tcctcatagg ggtaagcgtg gcagcgttcc tcgtcaaccc taatgtcacc actgtgagag    7500
aagcaggggt gttggtgacg gcggctacgc ttacttgtg ggacaatgga gccagtgccg     7560
tttggaattc caccacagcc acgggactct gccatgtcat gcgaggtagc tacctggctg    7620
gaggctccat tgcttggact ctcatcaaga acgctaataa gccctccttg aaaaggggaa    7680
ggcctgggg caggacgcta ggggagcagt ggaaggaaaa actaaatgcc atgagtagag     7740
aagagttttt taaataccgg agagaggcca taatcgaggt ggaccgcact gaagcacgca    7800
gggccagacg tgaaaataac atagtgggag acatccggt tcgcgaggc tcagcaaaac      7860
tccgttggct cgtggagaaa ggatttgtct cgccaatagg aaaagtcatt gatctagggt    7920
gtgggcgtgg aggatggagc tactacgcag caaccctgaa gaaggtccag gaagtcagag    7980
gatacacgaa aggtgggcg ggacatgaag aaccgatgct catgcagagc tacggctgga     8040
acctggtctc cctgaagagt ggagtggacg tgttttacaa accttcagag cccagtgata    8100
ccctgttctg tgacatagg gaatcctccc caagtccaga agtagaagaa caacgcacac     8160
```

```
tacgcgtcct agagatgaca tctgactggt tgcaccgagg acctagagag ttctgcatta   8220
aagttctctg cccttacatg cccaaggtta tagaaaaaat ggaagttctg cagcgtcgct   8280
tcggaggtgg gctagtgcgt ctccccctgt cccgaaactc caatcacgag atgtattggg   8340
ttagtggagc cgctggcaat gtggtgcacg ctgtgaacat gaccagccag gtattactgg   8400
ggcgaatgga tcgcacagtg tggagagggc caaagtatga ggaagatgtc aacctaggga   8460
gcggaacaag agccgtggga aagggagaag tccatagcaa tcaggagaaa atcaagaaga   8520
gaatccagaa gcttaaagaa gaattcgcca acgtggca caaagaccct gagcatccat    8580
accgcacttg gacataccac ggaagctatg aagtgaaggc tactggctca gccagctctc   8640
tcgtcaacgg agtggtgaag ctcatgagca accttggga cgccattgcc aacgtcacca    8700
ccatggccat gactgacacc accccttttg gacagcaaag agttttcaag gagaaagttg   8760
acacgaaggc tcctgagcca ccagctggag ccaaggaagt gctcaacgag accaccaact   8820
ggctgtgggc ctacttgtca cgggaaaaaa gaccccgctt gtgcaccaag gaagaattca   8880
ttaagaaagt taacagcaac gcggctcttg gagcagtgtt cgctgaacag aatcaatgga   8940
gcacggcgcg tgaggctgtg gatgacccgc ggttttggga gatggttgat aagagaggg    9000 aaaaccatct gcgaggagag tgtcacacat gtatctacaa catgatggga aaaagagaga   9060
gaagcctggg agagtttgga aaagctaaag gaagcagggc catttggttc atgtggcttg   9120
gagcacggta tctagagttt gaagctttgg ggttcctgaa tgaagaccat tggctgagcc   9180
gagagaattc aggaggtgga gtggaaggct caggcgtcca aaagctggga tacatcctcc   9240
gtgacatagc aggaaagcaa ggagggaaaa tgtacgctga tgataccgcc gggtgggaca   9300
ctagaattac cagaactgat ttagaaaatg aagctaaggt actggagctc ctagacggtg   9360
aacaccgcat gctcgcccga gccataattg aactgactta caggcacaaa gtggtcaagg   9420
tcatgagacc tgcagcagaa ggaaagaccg tgatggacgt gatatcaaga gaagatcaaa   9480
gggggagtgg acaggtggtc acttatgctc ttaacacttt cacgaacatc gctgtccagc   9540
tcgtcaggct gatggaggct gaggggtca ttgaccaca acacttggaa catctaccta    9600
ggaaaaacaa gatagctgtc aggacctggc tcttttgagaa tggagaggag agagtgacca   9660
ggatggcgat cagcggagac gactgtgccg tcaaaccgct ggacgacaga ttcgccacag   9720
ccctccactt cctcaacgca atgtcaaagg tcagaaaaga catccaggaa tggaagcctt   9780
cgcatggctg gcacgattgg cagcaagttc ccttctgttc taaccatttt caggagattg   9840
tgatgaaaga tggaaggagt atagttgtcc cgtgcagagg acaggatgag ctgataggca   9900
gggctcgcat ctctccagga gctggatgga atgtgaagga cacagcttgc ctggccaaag   9960
catatgcaca gatgtggcta ctcctatact tccatcgcag ggacttgcgt tcatggcaa   10020 atgcgatttg ctcagcagtg ccagtagatt gggtgcccac aggcaggaca tcctggtcaa   10080
tacactcgaa aggagagtgg atgaccacgg aagacatgct gcaggtctgg aacagagttt   10140
ggattgaaga aaatgaatgg atgatggaca agactccaat cacaagctgg acagacgttc   10200
cgtatgtggg aaagcgcgag gacatctggt gtggcagcct catcggaacg cgatccagag   10260
caacctgggc tgagaacatc tatgcggcga taaaccaggt tagagctgtc attgggaaag   10320
aaaattatgt tgactacatg acctcactca ggagatacga agacgtcttg atccaggaag   10380
acagggtcat ctagtgtgat ttaaggtaga aaagtagact atgtaaacaa tgtaaatgag   10440
aaaatgcatg catatggagt caggccagca aaagctgcca ccggatactg ggtagacggt   10500
```

-continued

```
gctgcctgcg tctcagtccc aggaggactg ggttaacaaa tctgacaaca gaaagtgaga   10560
aagccctcag aaccgtctcg gaagtaggtc cctgctcact ggaagttgaa agaccaacgt   10620
caggccacaa atttgtgcca ctccgctagg gagtgcggcc tgcgcagccc caggaggact   10680
gggttaccaa agccgttgag gcccccacgg cccaagcctc gtctaggatg caatagacga   10740
ggtgtaagga ctagaggtta gaggagaccc cgtggaaaca acaacatgcg gcccaagccc   10800
cctcgaagct gtagaggagg tggaaggact agaggttaga ggagaccccg catttgcatc   10860
aaacagcata ttgacacctg ggaatagact gggagatctt ctgctctatc tcaacatcag   10920
ctactaggca cagagcgccg aagtatgtag ctggtggtga ggaagaacac aggatct      10977
```